United States Patent
Pinto et al.

(10) Patent No.: US 9,315,519 B2
(45) Date of Patent: Apr. 19, 2016

(54) GUANIDINE SUBSTITUTED TETRAHYDROISOQUINOLINE COMPOUNDS AS FACTOR XIA INHIBITORS

(71) Applicant: BRISTOL-MYERS SQUIBB COMPANY, Princeton, NJ (US)

(72) Inventors: Donald J. P. Pinto, Churchville, PA (US); Charles G. Clark, Cherry Hill, NJ (US); Michael J. Orwat, New Hope, PA (US); Leon M. Smith, II, Somerset, NJ (US); William R. Ewing, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/434,765

(22) PCT Filed: Oct. 11, 2013

(86) PCT No.: PCT/US2013/064421
§ 371 (c)(1),
(2) Date: Apr. 10, 2015

(87) PCT Pub. No.: WO2014/059202
PCT Pub. Date: Apr. 17, 2014

(65) Prior Publication Data
US 2015/0259358 A1    Sep. 17, 2015

Related U.S. Application Data

(60) Provisional application No. 61/712,925, filed on Oct. 12, 2012.

(51) Int. Cl.
| | |
|---|---|
| *C07D 401/14* | (2006.01) |
| *C07D 495/04* | (2006.01) |
| *C07D 513/04* | (2006.01) |
| *A61K 31/4725* | (2006.01) |
| *A61K 31/4743* | (2006.01) |
| *A61K 31/4745* | (2006.01) |
| *A61K 31/496* | (2006.01) |
| *C07D 217/26* | (2006.01) |
| *C07D 401/06* | (2006.01) |

(52) U.S. Cl.
CPC ............ *C07D 513/04* (2013.01); *C07D 217/26* (2013.01); *C07D 401/06* (2013.01); *C07D 401/14* (2013.01); *C07D 495/04* (2013.01)

(58) Field of Classification Search
None
See application file for complete search history.

(56) References Cited

U.S. PATENT DOCUMENTS

| | | | |
|---|---|---|---|
| 5,624,936 A | 4/1997 | deSolms | |
| 5,869,682 A | 2/1999 | deSolms | |
| 2007/0112012 A1* | 5/2007 | Boehringer et al. | 514/255.05 |

FOREIGN PATENT DOCUMENTS

| | | |
|---|---|---|
| DE | 40 34 829 A1 | 5/1992 |
| EP | 0 525 420 B1 | 5/1999 |
| EP | 1 016 663 A1 | 7/2000 |
| EP | 1 125 925 A1 | 8/2001 |
| FR | 1525186 | 5/1968 |
| FR | 7155 | 2/1970 |
| WO | WO 93/20099 | 10/1993 |
| WO | WO 96/34010 | 10/1996 |
| WO | WO 97/36891 | 10/1997 |
| WO | WO 99/15530 | 4/1999 |
| WO | WO 99/47545 | 9/1999 |
| WO | WO 99/61444 | 12/1999 |
| WO | WO 00/18733 | 4/2000 |
| WO | WO 00/40571 | 7/2000 |
| WO | WO 00/61608 | 10/2000 |
| WO | WO 01/85695 | 11/2001 |
| WO | WO 02/18369 | 3/2002 |
| WO | WO 03/011222 | 2/2003 |
| WO | WO 03/041641 | 5/2003 |
| WO | WO 2004/080971 | 9/2004 |
| WO | WO 2004/094372 | 11/2004 |
| WO | WO 2005/014533 | 2/2005 |
| WO | WO 2005/099709 | 10/2005 |

(Continued)

OTHER PUBLICATIONS

Boger, D.L. et al., "Thermal Atropisomerism of Aglucovancomycin Derivatives: Preparation of (*M,M,M*)- and (*P,M,M*)-Aglucovancomycins", J. Am. Chem. Soc., vol. 120, No. 35, pp. 8920-8926 (1998).

(Continued)

*Primary Examiner* — Zinna Northington Davis
(74) *Attorney, Agent, or Firm* — Hong Liu

(57) ABSTRACT

The present invention provides compounds of Formula (I): or stereoisomers, pharmaceutically acceptable salts thereof, wherein all of the variables are as defined herein. These compounds are inhibitors of factor XIa and/or plasma kallikrein which may be used as medicaments.

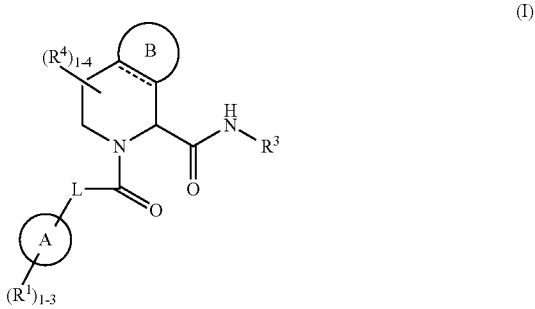

18 Claims, No Drawings

(56) References Cited

FOREIGN PATENT DOCUMENTS

| WO | WO 2005/123050 | 12/2005 |
|---|---|---|
| WO | WO 2005/123680 | 12/2005 |
| WO | WO 2006/017295 | 2/2006 |
| WO | WO 2006/076575 | 7/2006 |
| WO | WO 2006/089005 | 8/2006 |
| WO | WO 2007/054453 | 5/2007 |
| WO | WO 2007/070816 | 6/2007 |
| WO | WO 2007/070818 | 6/2007 |
| WO | WO 2007/070826 | 6/2007 |
| WO | WO 2007/076431 | 7/2007 |
| WO | WO 2008/076805 | 6/2008 |
| WO | WO 2008/079836 | 7/2008 |
| WO | WO 2008/157162 | 12/2008 |
| WO | WO 2009/114677 | 9/2009 |
| WO | WO 2010/151317 | 12/2010 |
| WO | WO 2011/002520 | 1/2011 |
| WO | WO 2011/017296 | 2/2011 |
| WO | WO 2011/100401 | 8/2011 |
| WO | WO 2011/100402 | 8/2011 |
| WO | WO 2013/009527 | 1/2013 |
| WO | WO 2013/022814 | 2/2013 |
| WO | WO 2013/022818 | 2/2013 |
| WO | WO 2013/055984 | 4/2013 |
| WO | WO 2013/056034 | 4/2013 |
| WO | WO 2013/056060 | 4/2013 |
| WO | WO 2013/093484 | 6/2013 |
| WO | WO 2013/111107 | 8/2013 |
| WO | WO 2013/111108 | 8/2013 |
| WO | WO 2013/118805 | 8/2013 |
| WO | WO 2013/167669 | 11/2013 |
| WO | WO 2013/174937 | 11/2013 |
| WO | WO 2014/014050 | 1/2014 |
| WO | WO 2014/022766 | 2/2014 |
| WO | WO 2014/022767 | 2/2014 |
| WO | WO 2014/059203 | 4/2014 |
| WO | WO 2014/059214 | 4/2014 |
| WO | WO 2014/108679 | 7/2014 |
| WO | WO 2014/108685 | 7/2014 |
| WO | WO 2014/120346 | 8/2014 |
| WO | WO 2014/160668 | 10/2014 |

OTHER PUBLICATIONS

Caballero, J. et al., "Quantitative Structure-Activity Relationship Modeling of Growth Hormone Secretagogues Agonist Activity of Some Tetrahydroisoquinoline 1-Carboxamides", Chem. Biol. Drug. Des., vol. 69, pp. 48-55 (2007).
Chan, J.C.Y. et al., "The Characterization of Mice with a Targeted Combined Deficiency of Protein C and Factor XI", American Journal of Pathology, vol. 158, No. 2, pp. 469-479 (2001).
Chen, X. et al., Chapter 32: "The use of bioisosteric groups in lead optimization", Annual Reports in Medicinal Chemistry, vol. 38, pp. 333-346, Elsevier Inc., publ. (2003).
Cho, J.E. et al., "Characterization of Binding Mode for Human Coagulation Factor XI (FXI) Inhibitors", Bull. Korean Chem. Soc., vol. 34, No. 4, pp. 1212-1220 (2013).
Crosby, J.R. et al., "Antithrombotic Effect of Antisense Factor XI Oligonucleotide Treatment in Primates", Arterioscler. Thromb. Vasc. Biol., vol. 33, pp. 1670-1678 (2013), and vol. 33, pp. e127 and e130 (errata) (2013).
Evans, D.A. et al., "Total Syntheses of Vancomycin and Eremomycin Aglycons", Angew. Chem. Int. Ed., vol. 37, No. 19, pp. 2700-2704 (1998).
Gailani, D., "Gene Targeting in Hemostasis, Factor XI", Frontiers in Bioscience, vol. 6, pp. 201-207 (2001).
Gailani, D. et al., "A murine model of factor XI deficiency", Blood Coagulation and Fibrinolysis, vol. 8, pp. 134-144 (1997).
Gruber, A. et al., "Factor XI-dependence of surface- and tissue factor-initiated thrombus propagation in primates", Blood, vol. 102, No. 3, pp. 953-955 (2003).
Hoffman, M., "A cell-based model of coagulation and the role of factor VIIa", Blood Reviews, vol. 17, pp. S1-S5 (2003).
Jiang, G. et al., "Highly Efficient Oxidation of Amines to Imines by Singlet Oxygen and Its Application in Ugi-Type Reactions", Organic Letters, vol. 11, No. 20, pp. 4568-4571 (2009).
Li, J.J. et al., "Tetrahydroisoquinoline 1-carboxamides as growth hormone secretagogues", Bioorganic & Medicinal Chemistry Letters, vol. 15, pp. 1799-1802 (2005).
Matafonov, A. et al., "Evidence for factor IX-independent roles for factor XIa in blood coagulation", Journal of Thrombosis and Haemostasis, vol. 11, pp. 2118-2127 (2013).
MayoClinic.com, "Pulmonary Embolism: Prevention", http://www.mayoclinic.com/health/pulmonary-embolism/DS00429/DSECTION=prevention, accessed May 20, 2013.
Meijers, J.C.M. et al., "High Levels of Coagulation Factor XI as a Risk Factor for Venous Thrombosis", The New England Journal of Medicine, vol. 342, pp. 696-701 (2000).
Minnema, M.C. et al., "Activation of Clotting Factors XI and IX in Patients with Acute Myocardial Infarction", Arterioscler. Thromb. Vasc. Biol., vol. 20, pp. 2489-2493 (2000).
Murakami, T. et al., "Evaluation of Factor XIa-$\alpha_1$ -Antitrypsin in Plasma, a Contact Phase-Activated Coagulation Factor-Inhibitor Complex, in Patients with Coronary Artery Disease", Arteriosclerosis, Thrombosis, and Vascular Biology, vol. 15, No. 8, pp. 1107-1113 (1995).
Ngouansavanh, T. et al., "IBX-Mediated Oxidative Ugi-Type Multicomponent Reactions: Application to the N and C1 Functionalization of Tetrahydroisoquinoline", Angew. Chem. Int. Ed., vol. 46, pp. 5775-5778 (2007).
Rosen, E.D. et al., "FXI is Essential for Thrombus Formation Following $FeCl_3$ -Induced Injury of the Carotid Artery in the Mouse", Thromb. Haemost., vol. 87, pp. 774-776 (2002).
Schumacher, W.A. et al., "Inhibition of Factor XIa as a New Approach to Anticoagulation", Arterioscler. Thromb. Vasc. Biol., vol. 30, pp. 388-392 (2010).
Schuster, I. et al., "Convenient Synthesis of 1,2,3,4-Tetrahydroisoquinoline-1-Carboxylic Acid Derivatives via Isocyanide-Based Three-Component Reactions", Synthetic Communications, vol. 40, pp. 2488-2498 (2010).
Schuster, I. et al., "Synthesis of 1,2,3,4-Tetrahydroisoquinoline-1-Carboxylic Acid Derivatives Via Ugi Reactions", Letters in Organic Chemistry, vol. 4, No. 2, pp. 102-108 (2007).
Schuster, I. et al., "Synthesis of 1,2,3,4-Tetrahydroisoquinoline-1-carboxylic Acid Derivatives via Ugi Reactions", Magyar Kémiai Folyóirat (Hungarian Journal of Chemistry), vol. 116, No. 3, pp. 126-130 (2010).
Walsh, P.N., "Platelets and Factor XI Bypass the Contact System of Blood Coagulation", Thrombosis and Haemostasis, vol. 82, No. 2, pp. 234-242 (1999).
Wang, X. et al., "Effects of factor IX or factor XI deficiency on ferric chloride-induced carotid artery occlusion in mice", Journal of Thrombosis and Haemostasis, vol. 3, pp. 695-702 (2005).
Wu, Y.-J. et al., "Discovery of (S,E)-3-(2-fluorophenyl)-N-(1-(3-(pyridin-3-yloxy)phenyl)ethyl)acrylamide as a potent and efficacious KCNQ2 (Kv7.2) opener for the treatment of neuropathic pain", Bioorganic & Medicinal Chemistry Letters, vol. 23, pp. 6188-6191 (2013).

* cited by examiner

GUANIDINE SUBSTITUTED TETRAHYDROISOQUINOLINE COMPOUNDS AS FACTOR XIA INHIBITORS

CROSS REFERENCES TO RELATED APPLICATIONS

This application is a 371 of International Application No. PCT/US2013/064421, filed on Oct. 11, 2013, which claims the benefit of U.S. Provisional Application Ser. No. 61/712,925 filed on Oct. 12, 2012 which is incorporated herein by reference.

FIELD OF THE INVENTION

The present invention provides novel substituted tetrahydroisoquinoline (THQ) compounds, and their analogues thereof, which are inhibitors of factor XIa or plasma kallikrein, compositions containing them, and methods of using them, for example, for the treatment or prophylaxis of thromboembolic disorders.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007)). The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, factor XIa plays a key role in propagating this amplification loop and is thus an attractive target for anti-thrombotic therapy.

SUMMARY OF THE INVENTION

The present invention provides novel substituted tetrahydroisoquinoline compounds, and their analogues thereof, including stereoisomers, tautomers, pharmaceutically acceptable salts, or solvates thereof, which are useful as selective inhibitors of serine protease enzymes, especially factor XIa and/or plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides compounds of Formula (I):

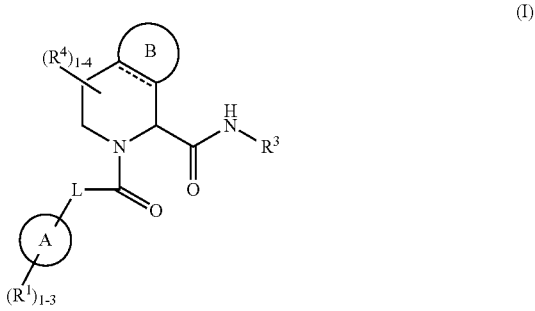

(I)

or stereoisomers, tautomers, pharmaceutically acceptable salts, or solvates thereof, wherein:

ring A is heterocycle comprising carbon atoms and 1-3 heteroatoms selected from $NR^2$, O, and $S(O)_p$;

L is selected from a bond, $-CHR^7-$, $-CHR^7CHR^7-$, $-CR^7=CR^7-$, $-C\equiv C-$, $-CHR^7NH-$, $-NHCHR^7-$, $-SCH_2-$, $-SO_2CH_2-$, $-NHCH_2-$, and $-CH_2NH-$;

ring B is phenyl or 5- to 6-membered heterocycle containing carbon atoms and 1-3 heteroatoms selected from the group consisting of N, $NR^6$, O, and $S(O)_p$, wherein said phenyl or heterocycle is substituted with 0-3 $R^5$;

---- is an optional bond;

$R^1$, at each occurrence, is selected from H, F, $=O$, $-(CH_2)_n OR^6$, $-(CH_2)_n NH_2$, $-(CH_2)_n C(=NH)NH_2$, $-(CH_2)_n C(=NOR^6)NH_2$, and $-(CH_2)_n NHC(=NH)NH_2$;

$R^2$ is selected from H, $-C(=NH)NH_2$, and $C(=NOR^6)NH_2$;

$R^3$ is selected from $C_{1-6}$ alkyl substituted with 1-3 $R^{3a}$, $C_{3-10}$ carbocycle substituted with 1-3 $R^{3a}$, and 5-10 membered heterocycle comprising carbon atoms and 1-4 heteroatoms selected from N, NR$^a$, O, and S(O)$_p$; wherein said heterocycle is substituted with 1-3 R$^{3a}$;

R$^{3a}$, at each occurrence, is selected from H, halogen, C$_{1-4}$ alkyl, —OH, C$_{1-4}$ alkoxy, —CN, —NH$_2$, —NH(C$_{1-4}$ alkyl), —CO$_2$H, —CH$_2$CO$_2$H, —CO$_2$(C$_{1-4}$ alkyl), —CO$_2$—C$_{1-4}$ alkylene-O(C$_{1-4}$ alkyl), —CO$_2$—C$_{1-4}$ alkylene-N(C$_{1-4}$ alkyl)$_2$, —CONH$_2$, —CONH(C$_{1-6}$ alkyl), —CON(C$_{1-4}$ alkyl)$_2$, —CONHCO$_2$C$_{1-4}$ alkyl, —NHCOC$_{1-4}$ alkyl, —NHCO$_2$(C$_{1-4}$ alkyl), SO$_2$R$^6$, SO$_2$NR$^6$R$^6$, SO$_2$NHC(O)R$^6$, NHSO$_2$NR$^6$, NHSO$_2$R$^6$, R$^c$, —CONHR$^c$, and —CO$_2$R$^c$;

R$^4$, at each occurrence, is selected from H, F, and C$_{1-4}$ alkyl;

R$^5$ is selected from H, halogen, C$_{1-4}$ alkyl, C$_{1-4}$alkoxy, C$_{1-4}$haloalkoxy, OH, CN, NH$_2$, —N(C$_{1-4}$ alkyl)$_2$, NO$_2$, —OCO(C$_{1-4}$ alkyl), —O—C$_{1-4}$ alkylene-O(C$_{1-4}$ alkyl), —O—C$_{1-4}$ alkylene-N(C$_{1-4}$ alkyl)$_2$, —CO$_2$H, —CO$_2$(C$_{1-4}$ alkyl), —(CH$_2$)$_n$CONH$_2$, SO$_2$R$^6$, SO$_2$NR$^6$R$^6$, SO$_2$NHC(O)R$^6$, NHSO$_2$NR$^6$, NHSO$_2$R$^6$, —(CH$_2$)$_n$—C$_{3-10}$ carbocycle and —(CH$_2$)$_n$-5- to 12-membered heterocycle comprising carbon atoms and 1-4 heteroatoms selected from N, NR$^a$, O, and S(O)$_p$; wherein said carbocycle or heterocycle is substituted with 1-3 R$^b$;

R$^6$, at each occurrence, is selected from H and C$_{1-4}$ alkyl;

R$^7$, at each occurrence, is selected from H, halo, OH, CHF$_2$, CF$_3$, C$_{1-4}$ alkoxy, CH$_2$OH, and C$_{1-4}$ alkyl;

R$^a$, at each occurrence, is selected from H, C$_{1-4}$ alkyl, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$;

R$^b$, at each occurrence, is selected from H, CN, =O, OH, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$haloalkyl), CO$_2$(C$_{1-4}$ alkyl), CONH$_2$, —CONH(C$_{1-4}$ alkyl), —CON(C$_{1-4}$ alkyl)$_2$, —NHCO$_2$(C$_{1-4}$ alkyl), SO$_2$R$^6$, SO$_2$NR$^6$R$^6$, SO$_2$NHC(O)R$^6$, NHSO$_2$NR$^6$, NHSO$_2$R$^6$, —R$^c$, COR$^c$, CO$_2$R$^c$, and CONHR$^c$; optionally, R$^b$ and R$^b$ together with the carbon atom to which they are both attached form a 5-6 membered heterocyclic ring;

R$^c$, at each occurrence, is selected from —(CH$_2$)$_n$—C$_{3-6}$ cycloalkyl, —(CH$_2$)$_n$-phenyl, and —(CH$_2$)$_n$-5- to 6-membered heterocycle comprising carbon atoms and 1-4 heteroatoms selected from N, NH, N(C$_{1-4}$ alkyl), O, and S(O)$_p$; wherein each ring moiety is substituted with 0-2 R$^d$;

R$^d$, at each occurrence, is selected from =O, F, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and heterocycle comprising carbon atoms and 1-4 heteroatoms selected from N, NH, N(C$_{1-4}$ alkyl), O, and S(O)$_p$;

n, at each occurrence, is selected from 0, 1, 2, 3, and 4; and p, at each occurrence, is selected from 0, 1, and 2.

In another aspect, the present invention provides compounds of Formula (I) or stereoisomers, tautomers, pharmaceutically acceptable salts thereof wherein:

ring A is heterocycle comprising carbon atoms and 1-3 heteroatoms selected from NR$^2$, O, and S(O)$_p$, wherein said heterocycle may be a spiro;

L is selected from a bond and —CHR$^7$—;

ring B is phenyl or 5- to 6-membered heterocycle containing carbon atoms and 1-3 heteroatoms selected from the group consisting of N, NR$^6$, O, and S(O)$_p$, wherein said phenyl or heterocycle is substituted with 0-3 R$^5$;

---- is an optional bond;

R$^1$, at each occurrence, is selected from H, F, =O, —(CH$_2$)$_n$ OR$^6$, —(CH$_2$)$_n$NH$_2$;

R$^2$ is selected from H, —C(=NH)NH$_2$, and C(=NOR$^6$)NH$_2$;

R$^3$ is selected from C$_{1-6}$ alkyl substituted with 1-3 R$^{3a}$, C$_{3-10}$ carbocycle substituted with 1-3 R$^{3a}$, and 5-10 membered heterocycle comprising carbon atoms and 1-4 heteroatoms selected from N, NR$^a$, O, and S(O)$_p$; wherein said heterocycle is substituted with 1-3 R$^{3a}$;

R$^{3a}$, at each occurrence, is selected from H, halogen, C$_{1-4}$ alkyl, —OH, C$_{1-4}$ alkoxy, —CN, —NH$_2$, —NH(C$_{1-4}$ alkyl), —CO$_2$H, —CH$_2$CO$_2$H, —CO$_2$(C$_{1-4}$ alkyl), —CO$_2$—C$_{1-4}$ alkylene-O(C$_{1-4}$ alkyl), —CO$_2$—C$_{1-4}$ alkylene-N(C$_{1-4}$ alkyl)$_2$, —CONH$_2$, —CONH(C$_{1-6}$ alkyl), —CON(C$_{1-4}$ alkyl)$_2$, —CONHCO$_2$C$_{1-4}$ alkyl, —NHCOC$_{1-4}$ alkyl, —NHCO$_2$(C$_{1-4}$ alkyl), SO$_2$R$^6$, SO$_2$NR$^6$R$^6$, SO$_2$NHC(O)R$^6$, NHSO$_2$NR$^6$, NHSO$_2$R$^6$, R$^c$, —CONHR$^c$, and —CO$_2$R$^c$;

R$^4$, at each occurrence, is selected from H, F, and C$_{1-4}$ alkyl;

R$^5$ is selected from H, halogen, C$_{1-4}$ alkyl, C$_{1-4}$alkoxy, C$_{1-4}$haloalkoxy, OH, CN, NH$_2$, —N(C$_{1-4}$ alkyl)$_2$, NO$_2$, —OCO(C$_{1-4}$ alkyl), —O—C$_{1-4}$ alkylene-O(C$_{1-4}$ alkyl), —O—C$_{1-4}$ alkylene-N(C$_{1-4}$ alkyl)$_2$, —CO$_2$H, —CO$_2$(C$_{1-4}$ alkyl), —(CH$_2$)$_n$CONH$_2$, SO$_2$R$^6$, SO$_2$NR$^6$R$^6$, SO$_2$NHC(O)R$^6$, NHSO$_2$NR$^6$, NHSO$_2$R$^6$, —(CH$_2$)$_n$—C$_{3-10}$ carbocycle and —(CH$_2$)$_n$-5- to 12-membered heterocycle comprising carbon atoms and 1-4 heteroatoms selected from N, NR$^a$, O, and S(O)$_p$; wherein said carbocycle or heterocycle is substituted with 1-3 R$^b$;

R$^6$, at each occurrence, is selected from H and C$_{1-4}$ alkyl;

R$^7$, at each occurrence, is selected from H, halo, OH, and C$_{1-4}$ alkyl;

R$^a$, at each occurrence, is selected from H, C$_{1-4}$ alkyl, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$;

R$^b$, at each occurrence, is selected from H, CN, =O, OH, halogen, C$_{1-4}$ alkyl, C$_{1-4}$ alkoxy, OCF$_3$, NH$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —NHCO$_2$(C$_{1-4}$ alkyl), SO$_2$(C$_{1-4}$ alkyl), SO$_2$NH(C$_{1-4}$ alkyl), NHSO$_2$NR$^6$, NHSO$_2$(C$_{1-4}$ alkyl), —R$^c$, COR$^c$, CO$_2$R$^c$, and CONHR$^c$; optionally, R$^b$ and R$^b$ together with the carbon atom to which they are both attached form a 5-6 membered heterocyclic ring;

R$^c$, at each occurrence, is selected from —(CH$_2$)$_n$—C$_{3-6}$ cycloalkyl, —(CH$_2$)$_n$-phenyl, and —(CH$_2$)$_n$-5- to 6-membered heterocycle comprising carbon atoms and 1-4 heteroatoms selected from N, NH, N(C$_{1-4}$ alkyl), O, and S(O)$_p$; wherein each ring moiety is substituted with 0-2 R$^d$;

R$^d$, at each occurrence, is selected from =O, F, —OH, C$_{1-4}$ alkyl, NH$_2$, NH(C$_{1-4}$ alkyl), N(C$_{1-4}$ alkyl)$_2$, and C$_{1-4}$ alkoxy;

n, at each occurrence, is selected from 0, 1, 2, 3, and 4; and p, at each occurrence, is selected from 0, 1, and 2.

In another aspect, the present invention includes compounds of Formula (II):

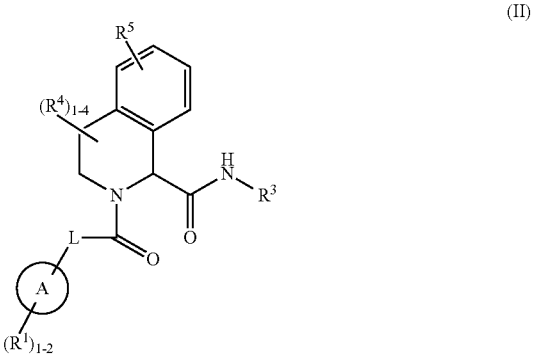

or stereoisomers, tautomers, pharmaceutically acceptable salts, or solvates thereof wherein:

ring A is 4- to 12-membered monocyclic, bicyclic heterocycle comprising carbon atoms and 1-3 heteroatoms selected from N, $NR^2$, and O and $S(O)_p$, wherein said heterocycle may be a spiro;

L is selected from a bond and —$CHR^7$—;

$R^1$, at each occurrence, is selected from H, F, =O, —$(CH_2)_n$ $OR^6$, and —$(CH_2)_n NH_2$;

$R^2$ is selected from H, —C(=NH)$NH_2$, and C(=$NOR^6$)$NH_2$;

$R^3$ is selected from $C_{3-10}$ carbocycle substituted with 1-3 $R^{3a}$, and 5-10 membered heterocycle comprising carbon atoms and 1-4 heteroatoms selected from N, $NR^a$, O, and $S(O)_p$; wherein said heterocycle is substituted with 1-3 $R^{3a}$;

$R^{3a}$, at each occurrence, is selected from H, halogen, $C_{1-4}$ alkyl, —OH, $C_{1-4}$ alkoxy, —CN, —$NH_2$, —NH($C_{1-4}$ alkyl), —$CO_2H$, $CO_2(C_{1-4}$ alkyl), and —$NHCO_2(C_{1-4}$ alkyl);

$R^4$, at each occurrence, is selected from H, F, and $C_{1-4}$ alkyl;

$R^5$ is selected from H, halogen, $C_{1-4}$alkoxy, $C_{1-4}$haloalkoxy, —$(CH_2)_n$—$C_{3-10}$ carbocycle and —$(CH_2)_n$-5- to 10-membered heterocycle comprising carbon atoms and 1-4 heteroatoms selected from N, $NR^a$, 0, and $S(O)_p$; wherein said carbocycle or heterocycle is substituted with 1-3 $R^b$;

$R^6$, at each occurrence, is selected from H and $C_{1-4}$ alkyl;

$R^7$, at each occurrence, is selected from H and $C_{1-4}$ alkyl;

$R^a$ is selected from H, $C_{1-4}$ alkyl, CO($C_{1-4}$ alkyl), $COCF_3$, $CO_2(C_{1-4}$ alkyl), and —$CONH_2$;

$R^b$ is selected from H, =O, OH, halogen, CN, $C_{1-4}$ alkyl, $C_{1-4}$ alkoxy, $OCF_3$, $NH_2$, N($C_{1-4}$ alkyl)$_2$, CO($C_{1-4}$ alkyl), CO($C_{1-4}$ haloalkyl), $CO_2(C_{1-4}$ alkyl), $CONH_2$, —CONH($C_{1-4}$ alkyl), and —CON($C_{1-4}$ alkyl)$_2$, $SO_2(C_{1-4}$ alkyl), $SO_2NH(C_{1-4}$ alkyl), $NHSO_2NR^6$, $NHSO_2(C_{1-4}$ alkyl), and $R_c$; optionally, $R^b$ and $R^b$ together with the carbon atom to which they are both attached form a 4-6 membered heterocyclic ring.

In another aspect, the present invention includes compounds of Formula (II), or stereoisomers, tautomers, pharmaceutically acceptable salts, or solvates thereof wherein:

$R^5$ is selected from H, halogen, phenyl, and —$(CH_2)_n$-5- to 10-membered heterocycle or heteroaryl comprising carbon atoms and 1-4 heteroatoms selected from N, $NR^a$, O, and $S(O)_p$; wherein said phenyl or heterocycle is substituted with 1-3 $R^b$; and other variables are as defined in Formula (II) above.

In another aspect, the present invention includes compounds of Formula (II): or stereoisomers, tautomers, pharmaceutically acceptable salts, or solvates thereof, wherein:

$R^5$ is selected from H, F,

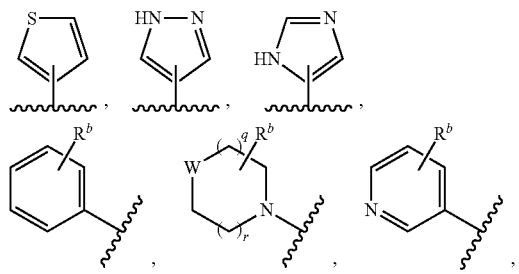

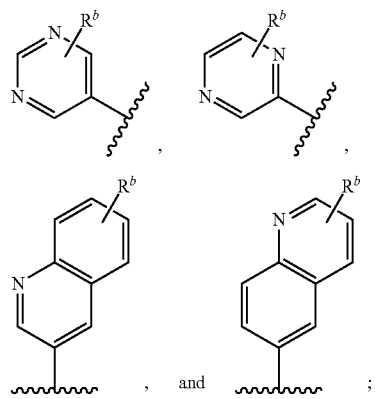

W is selected from $CR^b R^b$, O, $S(O)_p$, and $NR^a$;

$R^a$ is selected from H, $C_{1-4}$ alkyl, CO($C_{1-4}$ alkyl), and $COCF_3$;

$R^b$ is selected from H, =O, OH, halogen, $C_{1-4}$ alkyl, $C_{1-4}$ alkoxy, $OCF_3$, $NH_2$, N($C_{1-4}$ alkyl)$_2$, CO($C_{1-4}$ alkyl), CO($C_{1-4}$ haloalkyl), $CO_2(C_{1-4}$ alkyl), $CONH_2$, —CONH($C_{1-4}$ alkyl), —CON($C_{1-4}$ alkyl)$_2$, phenyl, pyridyl; optionally, $R^b$ and $R^b$ together with the carbon atom to which they are both attached form a 4-6 membered heterocyclic ring;

q, at each occurrence, is selected from 0, 1, and 2;

r, at each occurrence, is selected from 0, 1, and 2; and other variables are as defined in Formula (II) above.

In another aspect, the present invention includes compounds of Formula (II) or stereoisomers, tautomers, pharmaceutically acceptable salts, or solvates thereof wherein:

$R^5$ is

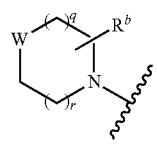

selected from

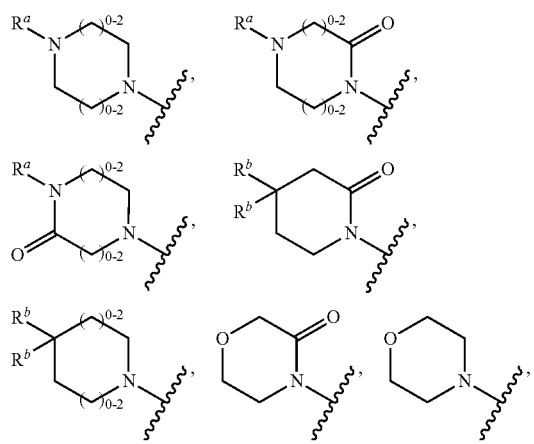

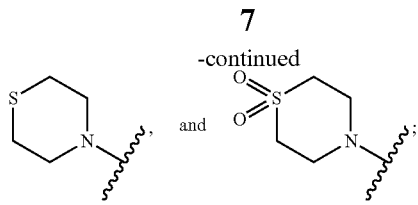 and 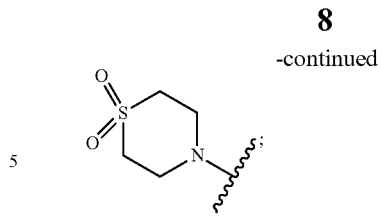

and
other variables are as defined in Formula (II) above.

In another aspect, the present invention includes compounds of Formula (II) or stereoisomers, tautomers, pharmaceutically acceptable salts thereof, wherein:

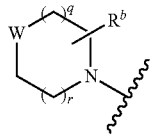

is selected from

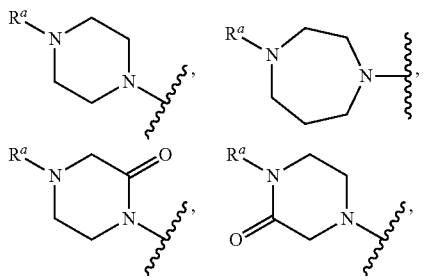

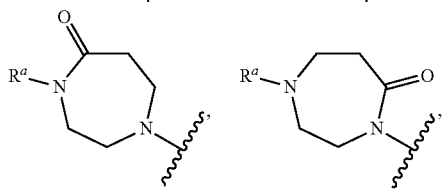

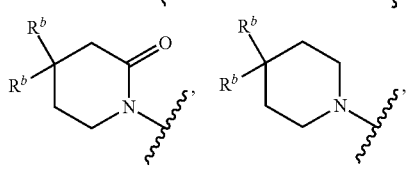

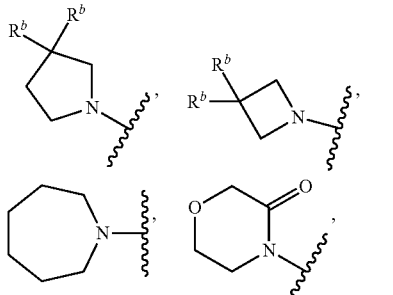

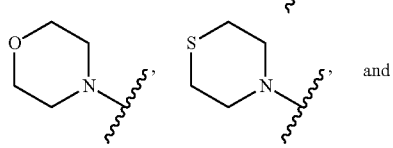 and and
other variables are as defined in Formula (II) above.

In another aspect, the present invention includes compounds of Formula (II), or stereoisomers, tautomers, pharmaceutically acceptable salts, or solvates thereof, wherein:
ring A is selected from

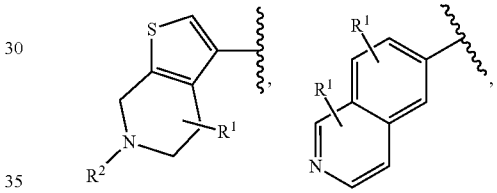

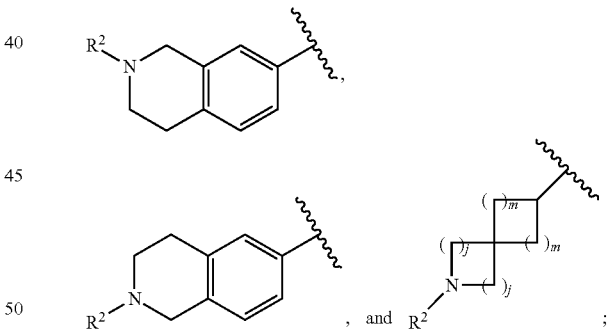

$R^1$, at each occurrence, is selected from H, F, =O, —(CH$_2$)$_n$OR$^6$, and —(CH$_2$)$_n$NH$_2$;
$R^2$ is selected from H, —C(=NH)NH$_2$, and C(=NOR$^6$)NH$_2$;
$R^3$ is selected from phenyl substituted with 1-2 R$^{3a}$, C$_{3-6}$ cycloalkyl substituted with 1-2 R$^{3a}$, heterocycle substituted with 1-2 R$^{3a}$; wherein said heterocycle is selected from piperidinyl, pyridyl, indolyl, and indazolyl;
$R^6$, at each occurrence, is selected from H and C$_{1-4}$ alkyl;
m, at each occurrence, is selected from 1 and 2;
j, at each occurrence, is selected from 1 and 2; and
other variables are as defined in Formula (II) above.

In another aspect, the present invention provides compounds of Formula (II): or stereoisomers, tautomers, pharmaceutically acceptable salts, or solvates thereof, wherein:

ring A is selected from

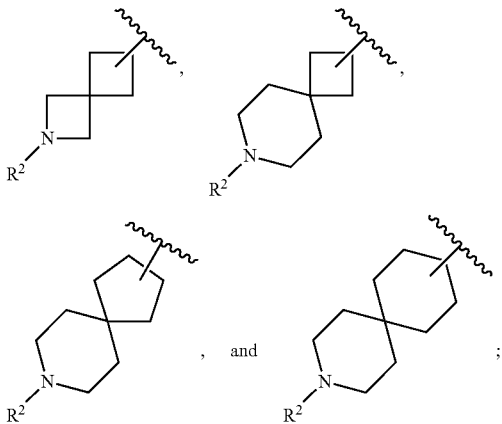

and other variables are as defined in Formula (II) above.

In another aspect, the present invention provides compounds of Formula (III):

(III)

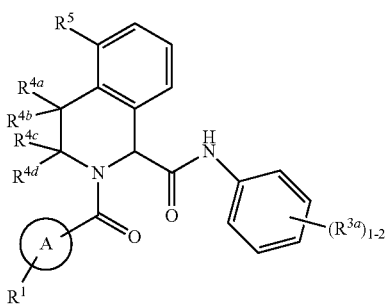

or stereoisomers, tautomers, pharmaceutically acceptable salts, or solvates thereof, wherein:

ring A is selected from

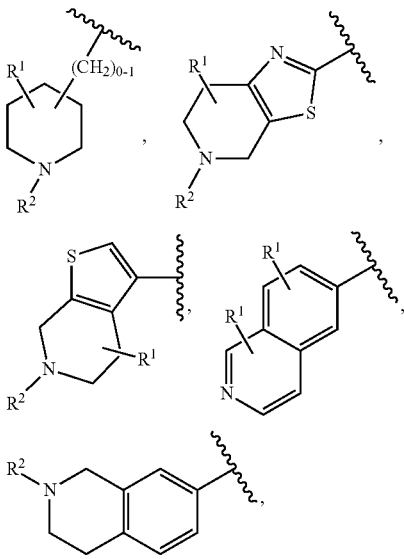

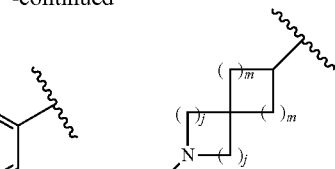

$R^1$, at each occurrence, is selected from H, F, =O, —(CH$_2$)$_n$OR$^6$, and —(CH$_2$)$_n$NH$_2$;

$R^2$ is selected from H, —C(=NH)NH$_2$, and C(=NOR$^6$)NH$_2$;

$R^{3a}$, at each occurrence, is selected from H, halogen, C$_{1-4}$ alkyl, —OH, C$_{1-4}$ alkoxy, —CN, —NH$_2$, —NH(C$_{1-4}$ alkyl), —N(C$_{1-4}$ alkyl)$_2$, —CO$_2$H, CO$_2$(C$_{1-4}$ alkyl), and —NHCO$_2$(C$_{1-4}$ alkyl);

$R^{4a}$, $R^{4b}$, $R^{4c}$, and $R^{4d}$ are independently selected from H, F, and C$_{1-4}$ alkyl;

$R^5$, at each occurrence, is selected from H, F,

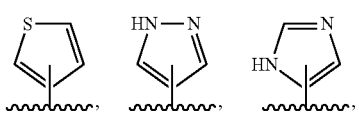

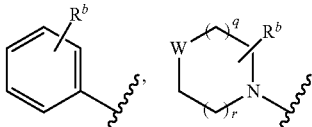

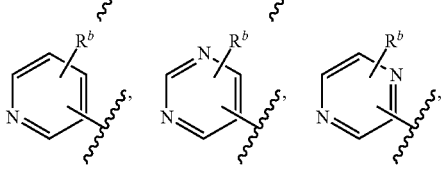

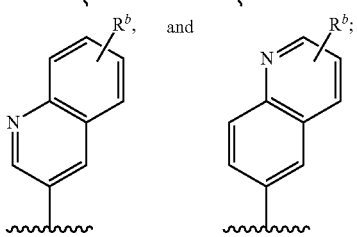

$R^6$, at each occurrence, is selected from H and C$_{1-4}$ alkyl;

W is selected from CR$^b$R$^b$, O, S(O)$_p$, and NR$^a$;

$R^a$ is selected from H and C$_{1-4}$ alkyl; and $R^b$ is selected from H, =O, OH, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), and —CON(C$_{1-4}$ alkyl)$_2$.

In another aspect, the present invention provides compounds of Formula (IV):

(IV)

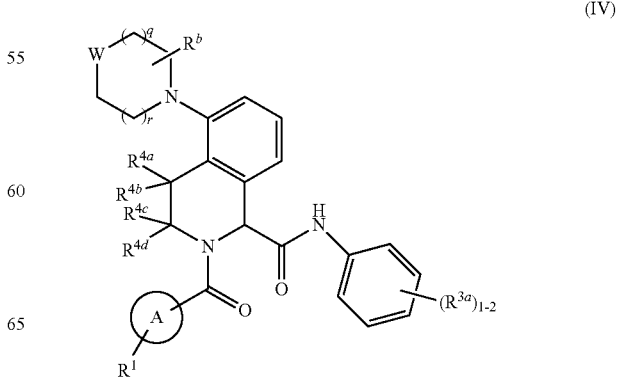

or stereoisomers, tautomers, pharmaceutically acceptable salts thereof, wherein:

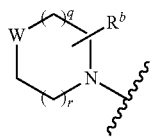

is selected from

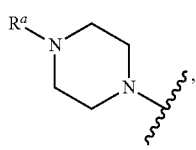 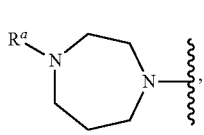

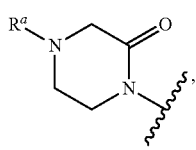 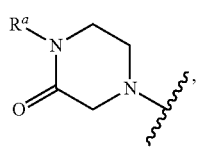

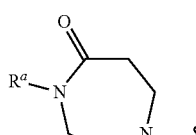 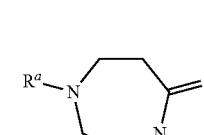

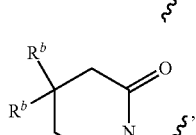 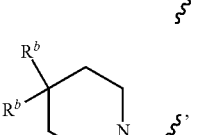

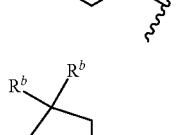 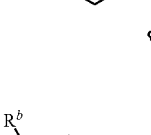

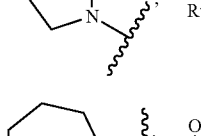 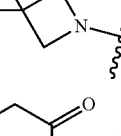

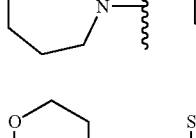 and

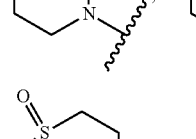

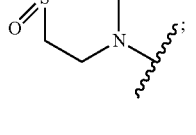

other variables are as defined in Formula (III) above.

In another aspect, the present invention provides compounds of Formula (V):

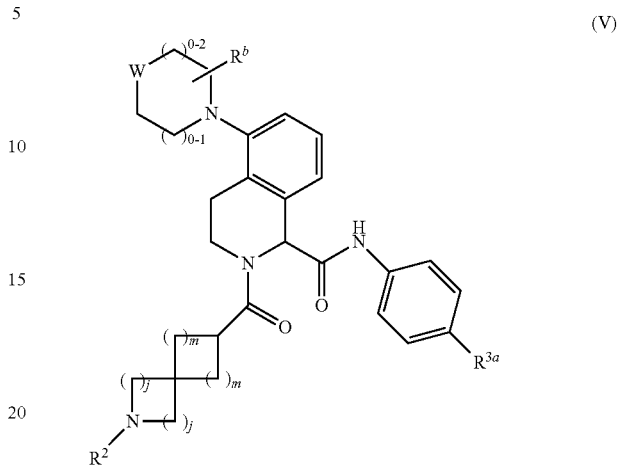

(V)

or stereoisomers, tautomers, pharmaceutically acceptable salts thereof, wherein:

$R^2$ is selected from H and —C(=NH)NH$_2$;

$R^{3a}$ is selected from $CO_2H$, $CO_2(C_{1-4}$ alkyl), and $NHCO_2(C_{1-4}$ alkyl);

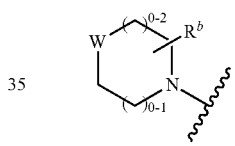

is selected from

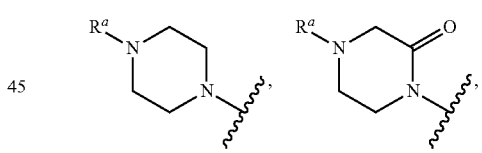

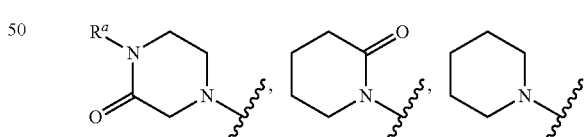

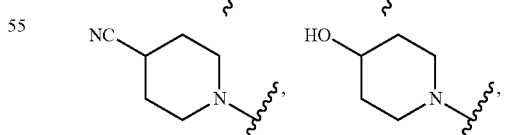

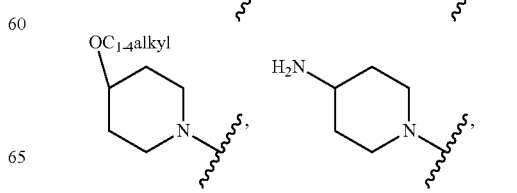

-continued

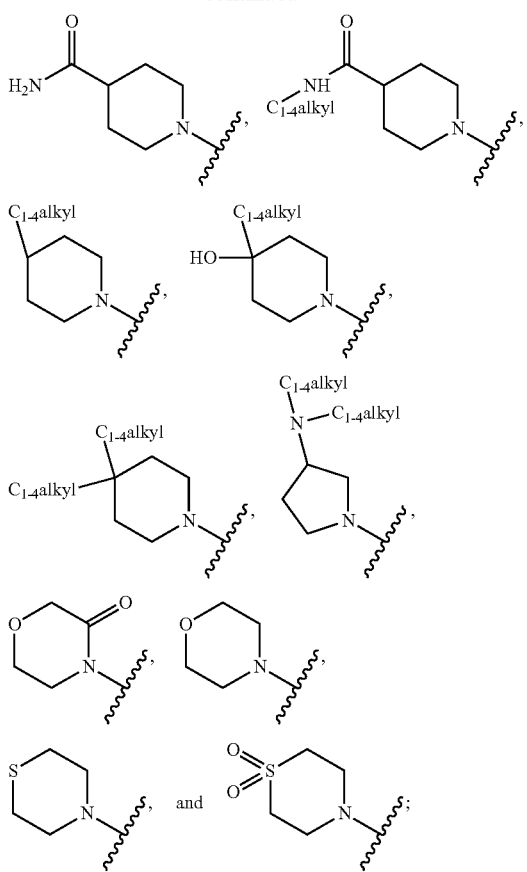

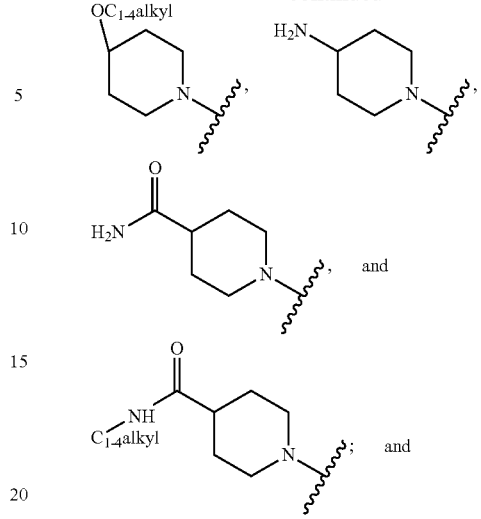

other variables are as defined in Formula (III) above.

In another aspect, the present invention provides compounds of Formula (VI):

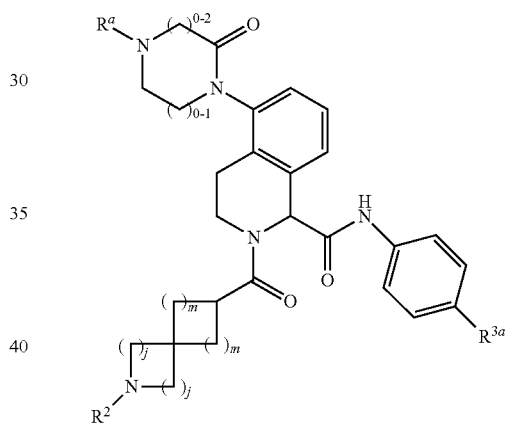

or a stereoisomer, tautomer, pharmaceutically acceptable salt thereof, wherein:
$R^2$ is selected from H and —C(=NH)NH$_2$;
$R^{3a}$ is selected from —CO$_2$H, —CO$_2$Me, and —NHCO$_2$Me;
$R^a$ is selected from H and C$_{1-4}$ alkyl;
j is 1 or 2; and
m is for 2.

In another aspect, the present invention provides a compound selected from the exemplified embodiments or a stereoisomer, a tautomer, a pharmaceutically acceptable salt, or a solvate thereof In another aspect, the present invention provides a compound selected from any subset list of compounds within the exemplified embodiments.

In another aspect, the present invention provides a compound of Formula (I), (II), (III), (IV), (V), or (VI), or a stereoisomer, a tautomer, a pharmaceutically acceptable salt, a solvate, or a prodrug thereof wherein ring A is a 5- to 6-membered monocyclic heterocycle comprising carbon atoms and 1-3 heteroatoms selected from NR$^2$, O, and S(O)$_p$, wherein R$^1$ is selected from H, F, =O, —(CH$_2$)$_n$OR$^6$, and —(CH$_2$)$_n$NH$_2$; R$^2$ is selected from H, —C(=NH)NH$_2$, and C(=NOR$^6$)NH$_2$;

m, at each occurrence, is selected from 1 and 2;
j, at each occurrence, is selected from 1 and 2; and
other variables are as defined in Formula (III) above.

In another aspect, the present invention provides compounds of Formula (V) or a stereoisomer, tautomer, pharmaceutically acceptable salt thereof, wherein:

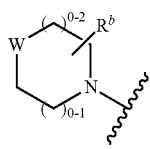

is selected from

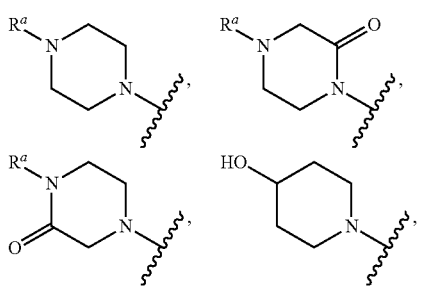

In another embodiment, ring A is

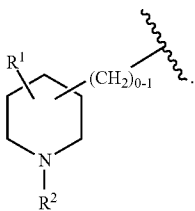

In another embodiment, ring A is a bicyclic heterocycle comprising carbon atoms and 1-3 heteroatoms selected from $NR^2$, O, and $S(O)_p$, wherein $R^1$ is selected from H, F, =O, —$(CH_2)_nOR^6$, and —$(CH_2)_nNH_2$; $R^2$ is selected from H, —C(=NH)$NH_2$, and C(=$NOR^6$)$NH_2$;

In one embodiment, ring A is selected from

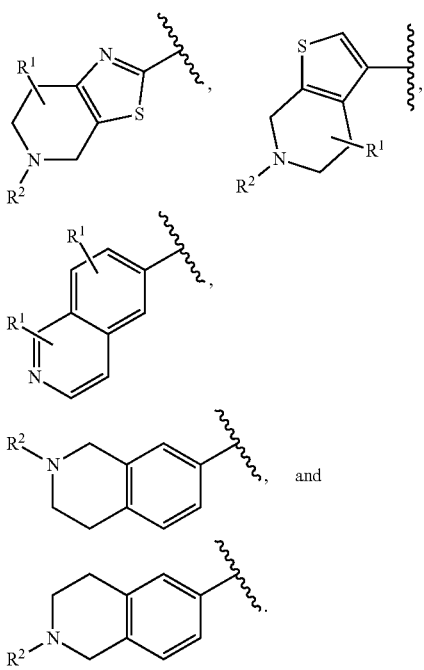

In another embodiment, ring A is a spiro heterocycle comprising carbon atoms and 1-3 heteroatoms selected from $NR^2$, O, and $S(O)_p$, wherein $R^1$ is selected from H, F, =O, —$(CH_2)_n$ $OR^6$, and —$(CH_2)_nNH_2$; $R^2$ is selected from H, —C(=NH)$NH_2$, and C(=$NOR^6$)$NH_2$;

In one embodiment, ring A is

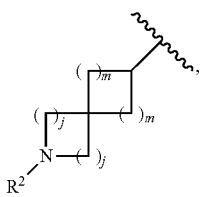

wherein m, at each occurrence, is selected from 1 and 2; and j, at each occurrence, is selected from 1 and 2.

In another embodiment, m is 1, j is 1.
In another embodiment, m is 2, j is 2.
In another embodiment, m is 1, j is 2.
In another embodiment, m is 2, j is 1.
In another embodiment, ring A is selected from

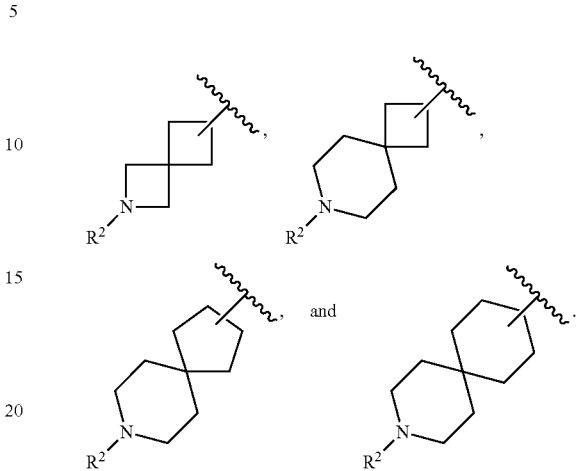

In another aspect, the present invention includes a compound of Formula (I), (II), (III), (IV), (V), or (VI), a stereoisomer, a tautomer, a pharmaceutically acceptable salt, a solvate, or a prodrug thereof, within the scope of any of the above aspects, wherein $R^5$ is selected from H, halogen, $C_{1-4}$ alkyl, $C_{1-4}$alkoxy, $C_{1-4}$haloalkoxy, OH, CN, $NH_2$, —N($C_{1-4}$ alkyl)$_2$, $NO_2$, —OCO($C_{1-4}$ alkyl), —O—$C_{1-4}$ alkylene-O($C_{1-4}$ alkyl), —O—$C_{1-4}$ alkylene-N($C_{1-4}$ alkyl)$_2$, —$CO_2H$, —$CO_2$($C_{1-4}$ alkyl), —$(CH_2)_pCONH_2$, —$(CH_2)_n$—$C_{3-10}$ carbocycle and —$(CH_2)_n$-5- to 12-membered heterocycle comprising carbon atoms and 1-4 heteroatoms selected from N, $NR^a$, O, and $S(O)_p$; wherein said carbocycle or heterocycle is substituted with 1-3 $R^b$; $R^b$, at each occurrence, is selected from H, CN, =O, OH, halogen, $C_{1-4}$ alkyl, $C_{1-4}$ alkoxy, $OCF_3$, $NH_2$, N($C_{1-4}$ alkyl)$_2$, CO($C_{1-4}$ alkyl), CO($C_{1-4}$ haloalkyl), $CO_2$ ($C_{1-4}$ alkyl), $CONH_2$, —CONH($C_{1-4}$ alkyl), —CON($C_{1-4}$ alkyl)$_2$, —$NHCO_2$($C_{1-4}$ alkyl), $SO_2$($C_{1-4}$ alkyl), $SO_2NH$($C_{1-4}$ alkyl), $NHSO_2NR^6$, $NHSO_2$($C_{1-4}$ alkyl), —$R^c$, $COR^c$, $CO_2R^c$, and $CONHR^c$; optionally, $R^b$ and $R^b$ together with the carbon atom to which they are both attached form a 5-6 membered heterocyclic ring.

In another embodiment, $R^5$ is selected from H, F,

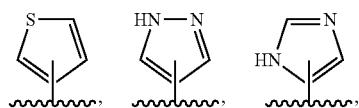

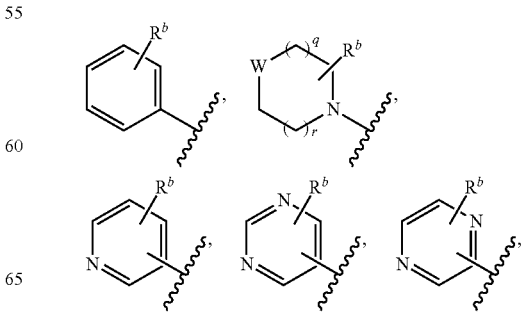

-continued
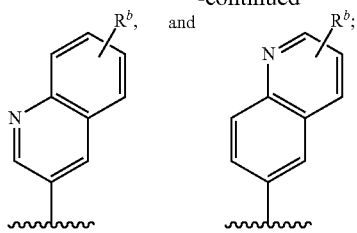
In another embodiment, R⁵ is
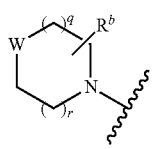
selected from
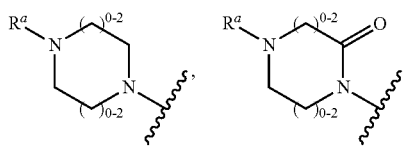
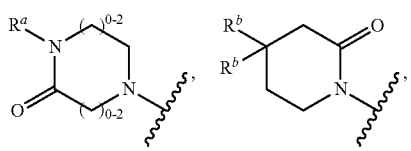
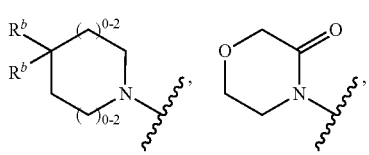
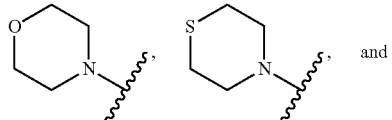
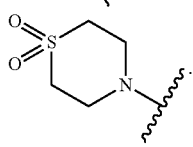
In another embodiment, R⁵ is
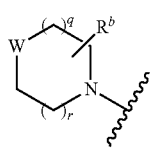
selected from
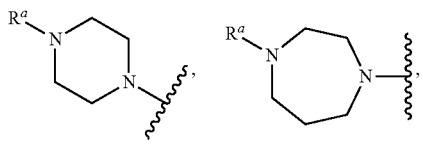
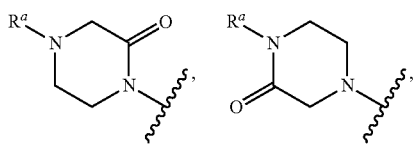
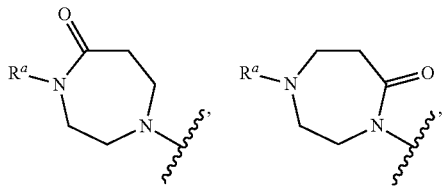
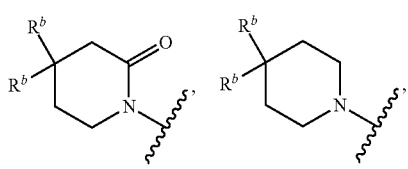
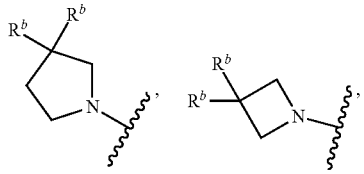
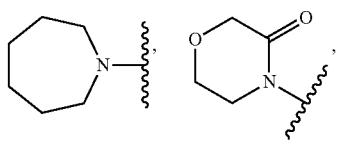
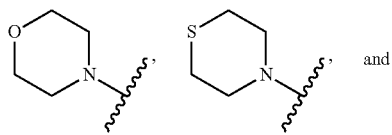
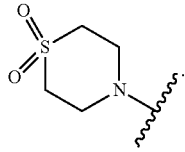
In another embodiment, R⁵ is
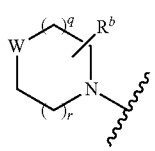

selected from

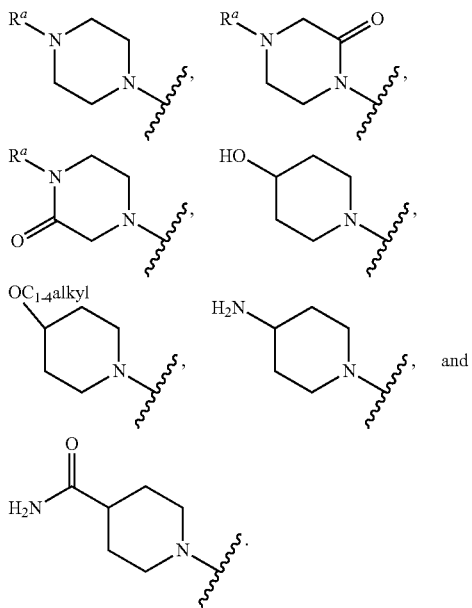

In another embodiment, $R^5$ is

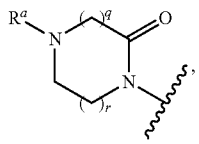

wherein $R^a$ is methyl or ethyl; q and r are independently selected from 0, 1, and 2.

In another embodiment, $R^5$ is

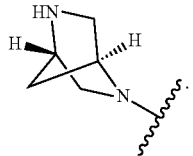

In another embodiment, $R^5$ is substituted pyrazole.

In another embodiment, L is selected from a bond, —$CHR^7CHR^7$—, —$CR^7$=$CR^7$—, —C≡C—, —$OCH_2$—, —$CHR^7NH$—, —$CH_2O$—, —$SCH_2$—, —$SO_2CH_2$—, and —$CH_2NH$—;

In another embodiment, L is independently selected from a bond, —$CH_2CH_2$—, —CH=CH—, —C(Me)=CH—, —C≡C—, and —$CH_2NH$—.

In another embodiment, L is independently selected from a bond, —$CH_2CH_2$—, —CH=CH—, and —C(Me)=CH.

In another embodiment, L is independently selected from a bond, —$CH_2CH_2$— and —CH=CH—.

In another embodiment, L is a bond.

In another embodiment, L is —$CH_2CH_2$—.

In another embodiment, $R^1$, at each occurrence, is selected from H, F, =O, —$(CH_2)_nOR^6$, and —$(CH_2)_nNH_2$;

In another embodiment, $R^1$, at each occurrence, is selected from H, F, =O, —$(CH_2)_nOR^6$, and —$(CH_2)_nNH_2$, wherein $R^6$ is H or $C_{1-4}$alkyl.

In another embodiment, $R^2$ is selected from H, —C(=NH)$NH_2$, and C(=$NOR^6$)$NH_2$, wherein $R^6$ is H or $C_{1-4}$alkyl.

In another embodiment, $R^3$ is selected from $C_{1-6}$ alkyl substituted with 1-3 $R^{3a}$, $C_{3-10}$ carbocycle substituted with 1-3 $R^{3a}$, and 5-10 membered heterocycle comprising carbon atoms and 1-4 heteroatoms selected from N, $NR^a$, O, and $S(O)_p$; wherein said heterocycle is substituted with 1-3 $R^{3a}$; $R^{3a}$, at each occurrence, is selected from H, halogen, $C_{1-4}$ alkyl, —OH, $C_{1-4}$ alkoxy, —CN, —$NH_2$, —NH($C_{1-4}$ alkyl), —$CO_2H$, —$CH_2CO_2H$, —$CO_2(C_{1-4}$ alkyl), —$CO_2$—$C_{1-4}$ alkylene-O($C_{1-4}$ alkyl), —$CO_2$—$C_{1-4}$ alkylene-N($C_{1-4}$ alkyl)$_2$, —$CONH_2$, —CONH($C_{1-6}$ alkyl), —CON($C_{1-4}$ alkyl)$_2$, —$CONHCO_2C_{1-4}$ alkyl, —$NHCOC_{1-4}$ alkyl, —$NHCO_2(C_{1-4}$ alkyl), $R^c$, —$CONHR^c$, and —$CO_2R^c$.

In another embodiment, $R^3$ is selected from $C_{3-10}$ carbocycle substituted with 1-3 $R^{3a}$, and 5-10 membered heterocycle comprising carbon atoms and 1-4 heteroatoms selected from N, $NR^a$, O, and $S(O)_p$; wherein said heterocycle is substituted with 1-3 $R^{3a}$; $R^{3a}$, at each occurrence, is selected from H, halogen, $C_{1-4}$ alkyl, —OH, $C_{1-4}$ alkoxy, —CN, —$NH_2$, —NH($C_{1-4}$ alkyl), —$CO_2H$, $CO_2(C_{1-4}$ alkyl), and —$NHCO_2(C_{1-4}$ alkyl).

In another embodiment, $R^3$ is selected from phenyl substituted with 1-2 $R^{3a}$, $C_{3-6}$ cycloalkyl substituted with 1-2 $R^{3a}$, heterocycle substituted with 1-2 $R^{3a}$; wherein said heterocycle is selected from piperidinyl, pyridyl, indolyl, and indazolyl.

In another embodiment, $R^3$ is phenyl; $R^{3a}$, at each occurrence, is selected from halogen, $CO_2H$, $CO_2(C_{1-4}$ alkyl), $NH_2$, $NHCO_2(C_{1-4}$ alkyl), and —$CH_2NHCO_2(C_{1-4}$ alkyl).

In another embodiment, $R^{3a}$ is $CO_2H$.

In another embodiment, $R^3$ is $C_{1-4}$ alkyl substituted with $R^{3a}$.

In another embodiment, $R^3$ is phenyl substituted with $R^{3a}$.

In another embodiment, $R^3$ is cyclohexyl substituted with $R^{3a}$.

In another embodiment, $R^7$ is selected from halogen, OH, $CHF_2$, $CF_3$, $C_{1-4}$ alkoxy, and $CH_2OH$.

In another embodiment, $R^7$ is selected from halogen, and $C_{1-4}$ alkyl.

In another embodiment, the compounds of the present invention have Factor XIa Ki values ≤10 μM.

In another embodiment, the compounds of the present invention have Factor XIa Ki values ≤1 μM.

In another embodiment, the compounds of the present invention have Factor XIa Ki values ≤0.5 μM.

In another embodiment, the compounds of the present invention have Factor XIa Ki values ≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a second factor XIa inhibitor, an anti-coagulant agent, an anti-platelet agent, a thrombin inhibiting agent, a thrombolytic agent, and a fibrinolytic agent. Preferably, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, desulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R," and "S" are used as described herein for indicating atom configuration(s) relative to a core molecule and are intended to be used as defined in the literature (IUPAC Recommendations 1996, Pure and Applied Chemistry, 68, 2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0] bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in *Hawley's Condensed Chemical Dictionary* (13th Ed.), Lewis, R. J., ed., J. Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, Bundgaard, H., ed., Elsevier (1985), and *Methods in Enzymology*, 112:309-396, Widder, K. et al., eds., Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, *Medicinal Chemistry: Principles and Practice*, King, F. D., ed. The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); *The Practice of Medicinal Chemistry*, Wermuth, C. G., ed., Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl
Ph Phenyl
Bn Benzyl
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOC or Boc tert-butoxycarbonyl
BOP reagent benzotriazol-1-yloxytris(dimethylamino)phosphonium hexafluorophosphate
Burgess reagent 1-methoxy-N-triethylammoniosulfonyl-methanimidate
CBz Carbobenzyloxy
$CH_3CN$ or ACN Acetonitrile
$CDCl_3$ deutero-chloroform
$CHCl_3$ Chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM or $CH_2Cl_2$ Dichloromethane
DEA Diethylamine
Dess-Martin 1,1,1-tris(acetyloxy)-1,1-dihydro-1,2-beniziodoxol-3-(1H)-one
DIC or DIPCDI Diisopropylcarbodiimide
DIEA, DIPEA diisopropylethylamine (Hunig's base)
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(SS)-EtDuPhosRh(I) (+)-1,2-bis((2S,5S)-2,5-diethylphospholano)benzene(1,5-cyclooctadiene)rhodium(I) trifluoromethanesulfonate
$Et_3N$ or TEA Triethylamine
EtOAc ethyl acetate Et$_2$O diethyl ether
EtOH Ethanol
GMF glass microfiber filter
Grubbs (II) (1,3-bis(2,4,6-trimethylphenyl)-2-imidazolidinylidene)dichloro(phenylmethylene) (triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
H$_2$SO$_4$ sulfuric acid
K$_2$CO$_3$ potassium carbonate
KOAc potassium acetate
K$_3$PO$_4$ potassium phosphate
LAH lithium aluminum hydride
LG leaving group
LiOH lithium hydroxide
MeOH methanol
MgSO$_4$ magnesium sulfate
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ ammonia
NH$_4$Cl ammonium chloride
NH$_4$OH ammonium hydroxide
OTf triflate or trifluoromethanesulfonate
Pd$_2$(dba)$_3$ tris(dibenzylideneacetone)dipalladium(0)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group
POCl$_3$ phosphorus oxychloride
i-PrOH or IPA isopropanol
PS polystyrene
SEM-Cl 2-(trimethysilyl)ethoxymethyl chloride
SiO$_2$ silica oxide
SnCl$_2$ tin(II) chloride
TBAI tetra-n-butylammonium iodide
TEA triethylamine
TFA trifluoroacetic acid
THF tetrahydrofuran
TMSCHN$_2$ trimethylsilyldiazomethane
T3P propane phosphonic acid anhydride
TRIS tris(hydroxymethyl)aminomethane The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis,* 3rd Ed., Wiley-Interscience (1999)).

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders which include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis, for example, alterations of the vessel wall, changes in the flow of blood, and alterations in the composition of the vascular compartment. These risk factors are collectively known as Virchow's triad. (*Hemostasis and Thrombosis, Basic Principles and Clinical Practice,* 5th Ed., p. 853, Colman, R. W. et al., eds., Lippincott Williams & Wilkins (2006))

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy) are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood*, 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood*, 108:192-199 (2006)). Contact activation is a surface mediated process responsible in part for the regulation of thrombosis and inflammation, and is mediated, at least in part, by fibrinolytic, complement, kininogen/kinin, and other humoral and cellular pathways (for review, Coleman, R., "Contact Activation Pathway", *Hemostasis and Thrombosis, pp.* 103-122, Lippincott Williams & Wilkins (2001); Schmaier, A. H., "Contact Activation", *Thrombosis and Hemorrhage*, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., *J. Exp. Med.*, 202:271-281 (2005); Kleinschmitz et al., *J. Exp. Med.*, 203:513-518 (2006)). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-1370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D., *Trends Cardiovasc. Med.*, 10:198-204 (2000))

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.*, 101:329-354 (2001)). Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al., *Thromb. Haemost.*, 87:774-777 (2002); Wang et al., *J. Thromb. Haemost.*, 3:695-702 (2005)). Also, factor XI deficiency rescues the perinatal lethal phenotype of complete protein C deficiency (Chan et al., *Amer. J. Pathology*, 158:469-479 (2001)). Furthermore, baboon cross-reactive, function blocking antibodies to human factor XI protect against baboon arterial-venous shunt thrombosis (Gruber et al., *Blood*, 102:953-955 (2003)). Evidence for an antithrombotic effect of small molecule inhibitors of factor XIa is also disclosed in published U.S. Patent Application No. 2004/0180855A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience*, 6:201-207 (2001); Gailani, D. et al., *Blood Coagulation and Fibrinolysis*, 8:134-144 (1997).) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either Cl inhibitor or alpha 1 antitrypsin.

In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al., *Arterioscler. Thromb. Vasc. Biol.*, 20:2489-2493 (2000)). A second study establishes a positive correlation between the extent of coronary arteriosclerosis and factor XIa in complex with alpha 1 antitrypsin (Murakami, T. et al., *Arterioscler. Thromb. Vasc. Biol.*, 15:1107-1113 (1995)). In another study, Factor XI levels above the 90th percentile in patients were associated with a 2.2-fold increased risk for venous thrombosis (Meijers, J. C. M. et al., *N Engl. J. Med.*, 342:696-701 (2000)).

Plasma kallikrein is a zymogen of a trypsin-like serine protease and is present in plasma at 35 to 50 µg/mL. The gene structure is similar to that of factor XI. Overall, the amino acid sequence of plasma kallikrein has 58% homology to factor XI. Proteolytic activation by factor XIIa at an internal I389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", *Hemostasis and Thrombosis*, pp. 103-122, Lippincott Williams & Wilkins (2001); Schmaier A. H., "Contact Activation", *Thrombosis and Hemorrhage*, pp. 105-128 (1998)).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H. et al., "Screening Tests of Hemostasis", *Disorders of Thrombosis and Hemostasis: A Clinical Guide*, 2nd Ed., pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility, (i) factors that are ideal for use as a parenteral agent such as solubility profile and pharmocokinetics.

Pre-clinical studies demonstrated significant antithrombotic effects of small molecule factor XIa inhibitors in rabbit and rat model of arterial thrombosis, at doses that preserved hemostasis. (Wong P. C. et al., *American Heart Association Scientific Sessions*, Abstract No. 6118, Nov. 12-15, 2006; Schumacher, W. et al., *Journal of Thrombosis and Haemostasis*, Vol. 3 (Suppl. 1):P1228 (2005); Schumacher, W. A. et al., *European Journal of Pharmacology*, pp. 167-174 (2007)).

Furthermore, it was observed that in vitro prolongation of the aPTT by specific XIa inhibitors is a good predictor of efficacy in our thrombosis models. Thus, the in vitro aPTT test can be used as a surrogate for efficacy in vivo.

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *British Journal of Surgery*, 88:913-930 (2001).)

A. In Vitro Assays

The effectiveness of compounds of the present invention as inhibitors of the coagulation factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; CHROMOGENIX® or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 1-5 nM, recombinant soluble tissue factor at a concentration of 10-40 nM and the synthetic substrate H-D-Ile-Pro-Arg-pNA (S-2288; CHROMOGENIX® or BMPM-2; AnaSpec) at a concentration of 0.001-0.0075 M.

Factor IXa determinations were made in 0.005 M calcium chloride, 0.1 M sodium chloride, 0.0001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu(gamma-OMe, 50%)-Gly-Arg-pNA; CHROMOGENIX®) at a concentration of 0.0002-0.00035 M.

Factor XIIa determinations were made in 50 mM HEPES buffer at pH 7.4 containing 145 mM NaCl, 5 mM KCl, and 0.1% PEG 8000. Determinations were made using purified human Factor XIIa at a final concentration of 4 nM (American Diagnostica) and the synthetic substrate SPECTROZYME® #312 (pyroGlu-Pro-Arg-pNA; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; CHROMOGENIX®) at a concentration of 0.00008-0.0004 M. The $K_m$ value used for calculation of $K_i$ was 0.00005 to 0.00007 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; CHROMOGENIX®) at a concentration of 0.0002-0.00026 M.

The Michaelis constant, $K_m$, for substrate hydrolysis by each protease, was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$$(v_o - v_s)/v_s = I/(K_i(1 + S/K_m)) \text{ for a competitive inhibitor with one binding site; or}$$

$$v_s/v_o = A + ((B-A)/1 + ((IC_{50}/(I)_n))); \text{ and}$$

$$K_i = IC_{50}/(1 + S/K_m) \text{ for a competitive inhibitor}$$

where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective. Compounds with selectivity ratios >100 are preferred, and compounds with selectivity ratios >500 are more preferred.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 50 or 100 percent, respectively. The IC1.5× or IC2× is found by linear interpolation from relative clotting time versus inhibitor concentration plots using inhibitor concentration that spans the IC1.5× or IC2×.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Illinois). Similarly, clotting times can be determined from laboratory animal species or humans dosed with compounds of the invention.

Activated Partial Thromboplastin Time (aPTT) is determined using ALEXIN® (Trinity Biotech, Ireland) or ACTIN® (Dade-Behring, Illinois) following the directions in the package insert. Plasma (0.05 mL) is warmed to 37° C. for 1 minute. ALEXIN® or ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus, Dade-Behring, Illinois) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

The exemplified Examples disclosed below were tested in the Factor XIa assay described above and found having Factor XIa inhibitory activity. Table 1 below lists Factor XIa Ki values measured for the following examples.

TABLE 1

| Example No. | Factor XIa Ki (nM) |
|---|---|
| 1 | 90.64 |
| 5 | <5.00 |
| 12 | 190.00 |
| 18 | <5.00 |
| 19 | 382.30 |
| 24 | 5.68 |

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-Induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arterio-Venous (AV) Shunt Thrombosis Model

The rabbit AV shunt model, described by Wong et al. (Wong, P. C. et al., *J. Pharmacol. Exp. Ther.* 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm) The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Ed. (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 100 milligrams per dosage unit, and the second anti-coagulant in an amount of about 1 to about 50 milligrams per dosage unit.

Where the compounds of the present invention are administered in combination with an anti-platelet agent, by way of general guidance, typically a daily dosage may be about 0.01 to about 25 milligrams of the compound of the present invention and about 50 to about 150 milligrams of the anti-platelet agent, preferably about 0.1 to about 1 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 1 milligrams of the compound of the present invention, per kilogram of patient body weight and, in the case of the thrombolytic agents, the usual dosage of the thrombolytic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof In another embodiment, the present invention provides a pharmaceutical composition further comprising additional therapeutic agent(s) selected from an antiarrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (alliskerin) and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX®), synthetic pentasaccharide, direct acting thrombin inhibitors including hirudin and argatroban, as well as other factor VIIa inhibitors, factor IXa inhibitors, factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDs) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof Other examples of suitable anti-platelet agents for use in combination with the compounds of the present invention, with or without aspirin, are ADP (adenosine diphosphate) receptor antagonists, preferably antagonists of the purinergic receptors $P2Y_1$ and $P2Y_{12}$, with $P2Y_{12}$ being even more preferred. Preferred $P2Y_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastrointestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPARgamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXR beta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 μM against the target protease and greater than or equal to 0.1 μM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages.

The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., Heterocycles, 16(1): 35-7 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Scheme 1 illustrates a few approaches to the synthesis of compounds of Formula (I). Amide 1c can be prepared by amide coupling of commercially available or readily accessible acid 1a and readily accessible aniline 1b using methods commonly used in the literature, such as T3P/base, HOAt/EDC/base and/or POCl$_3$, pyridine. Deprotection of the protecting group PG$_1$ using appropriate conditions known to those in the art of organic synthesis, followed by coupling with acid 1e can yield compounds of formula 1g. Alternatively, coupling of amine 1d with acid 1e followed by deprotection can give acid 1f. The coupling of acid 1f with amine 1b under standard peptide coupling procedures can yield compounds of formula 1g. Appropriate functionalization of intermediates used in this invention to prepare compounds of formula 1g can be achieved through the Suzuki, Buchwald, Ullman or Mitsunobu reactions or simple reactions known to those in the art.

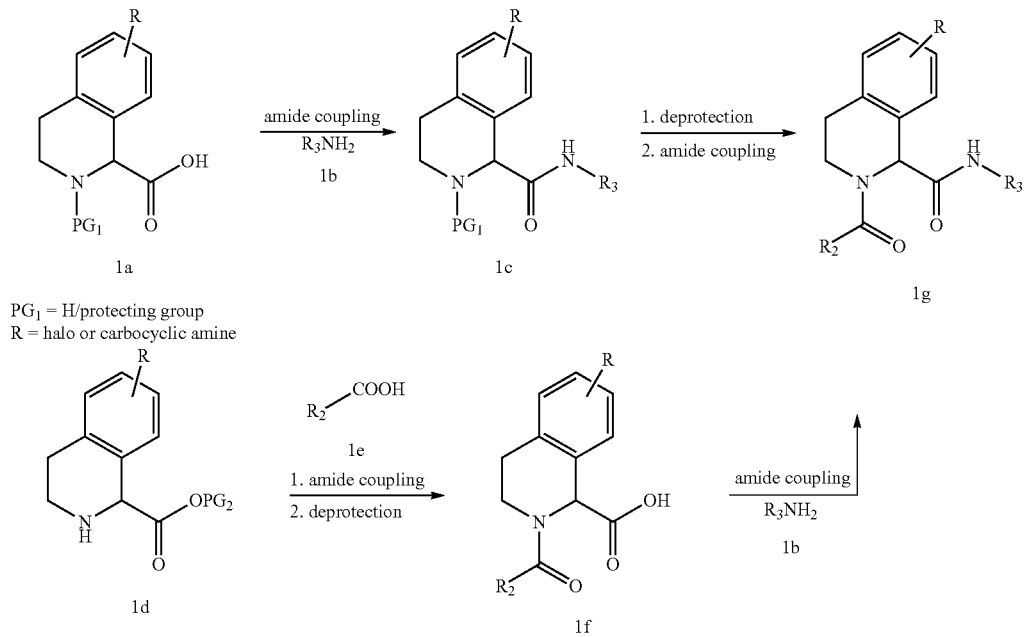

Scheme 2 describes an alternative method to access compounds of this invention. Reaction of acid 1e, isocyanide 2a, and imine 2b can give Ugi product 2d (Schuster, I. et al., Letters in Organic Chemistry, 4(2):102-108 (2007)). Selective oxidation of tetrahydroisoquinoline 2c using known methods such as MnO$_2$ (Aoyama, T. et al., Synlett, 1:35-36 (1998)) can yield imine 2b, which can then be used via the three component Ugi coupling procedures described above. The Ugi coupling procedures can be used extensively with other imino derived intermediates contained in this invention. Further manipulations of the Ugi derived products can afford compounds of this invention.

Scheme 2:

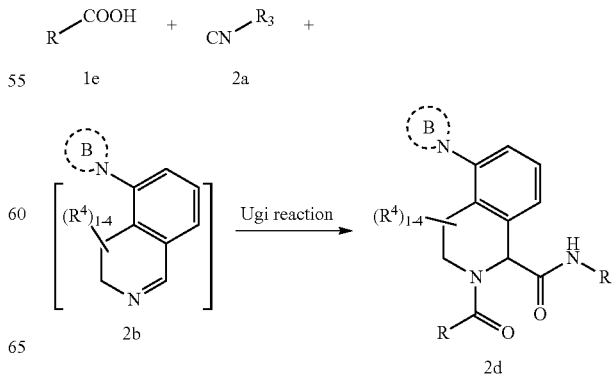

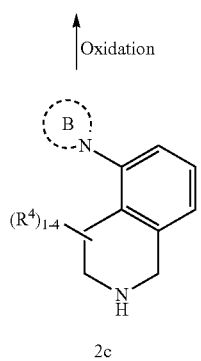

Scheme 3 describes methods for preparing the tetrahydroisoquinoline intermediate 3c and 3e. Method A uses Bischler-Napieralski cyclization to access compounds such as intermediate 3c (Al-Hiari, Y. M. et al., Journal of Heterocyclic Chemistry, 42(4): 647-659 (2005)) or 3e (Zalan, Z. et al., Tetrahedron, 62(12): 2883-2891 (2006)). Method B uses the Friedel-Crafts alkylation reaction to access compounds such as intermediate 3c (Topsom, R. D. et al., Journal of the Chemical Society [Section] D: Chemical Communications, 15:799 (1971)). Alternatively, as described in Method C, cyclization of intermediate 3h and 3-aminopropanol (3i) can afford 3j. Reduction with NaBH$_4$, followed by PCC oxidation gave β-amino aldehyde, which can be converted to 3c under basic conditions (Umetsu, K.; Asao, N., Tetrahedron Letters, 49(17): 2722-2725 (2008)). In Method D, lactam 3l can be synthesized from ketone 3k by the Beckmann rearrangement. Reduction of 3l can afford intermediates such as 3c (Vernier, J. et al., WO 2008024398 (2008)). In Method E, the dihydroisoquinoline carbaldehyde (3m) was converted to 3c under basic conditions (Martin, S. et al., WO 2006134143 (2006)). In Method F, dihydroisoquinolinethione was converted to 3c treating the thione 3o with bromopropene followed by treatment with perchloric acid and sodium borohydride (Mohinder, B, et al., Indian Journal of Chemistry, Section B: Organic Chemistry Including Medicinal Chemistry, 18B (4); 312-15 (1979)).

Scheme 3:

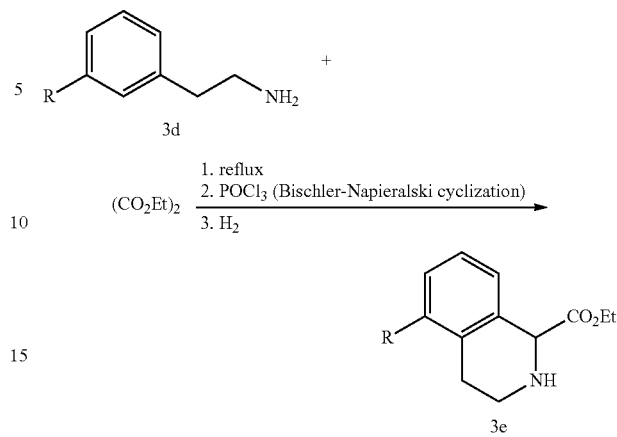

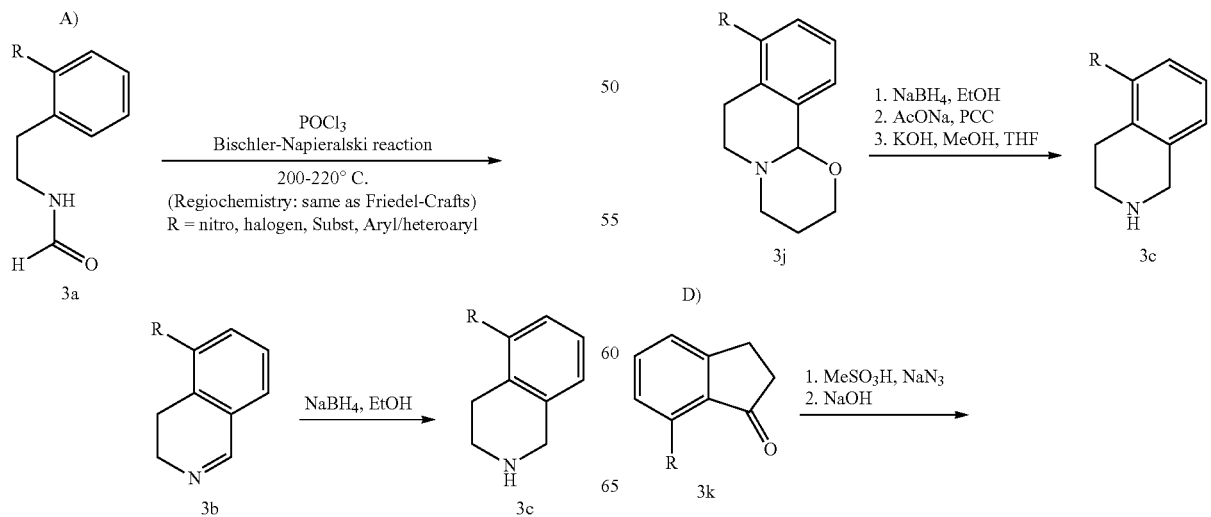

Scheme 4:

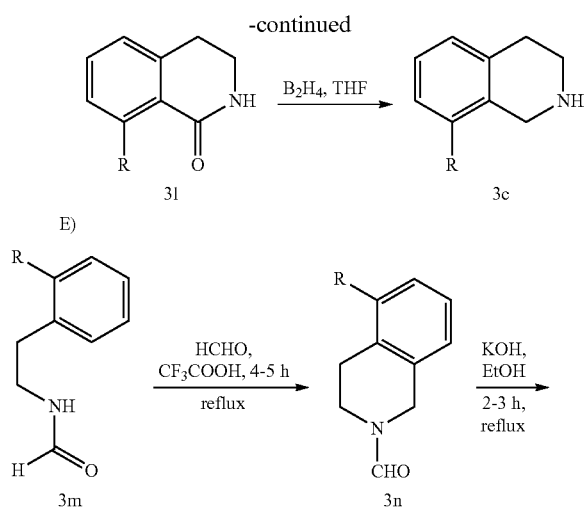
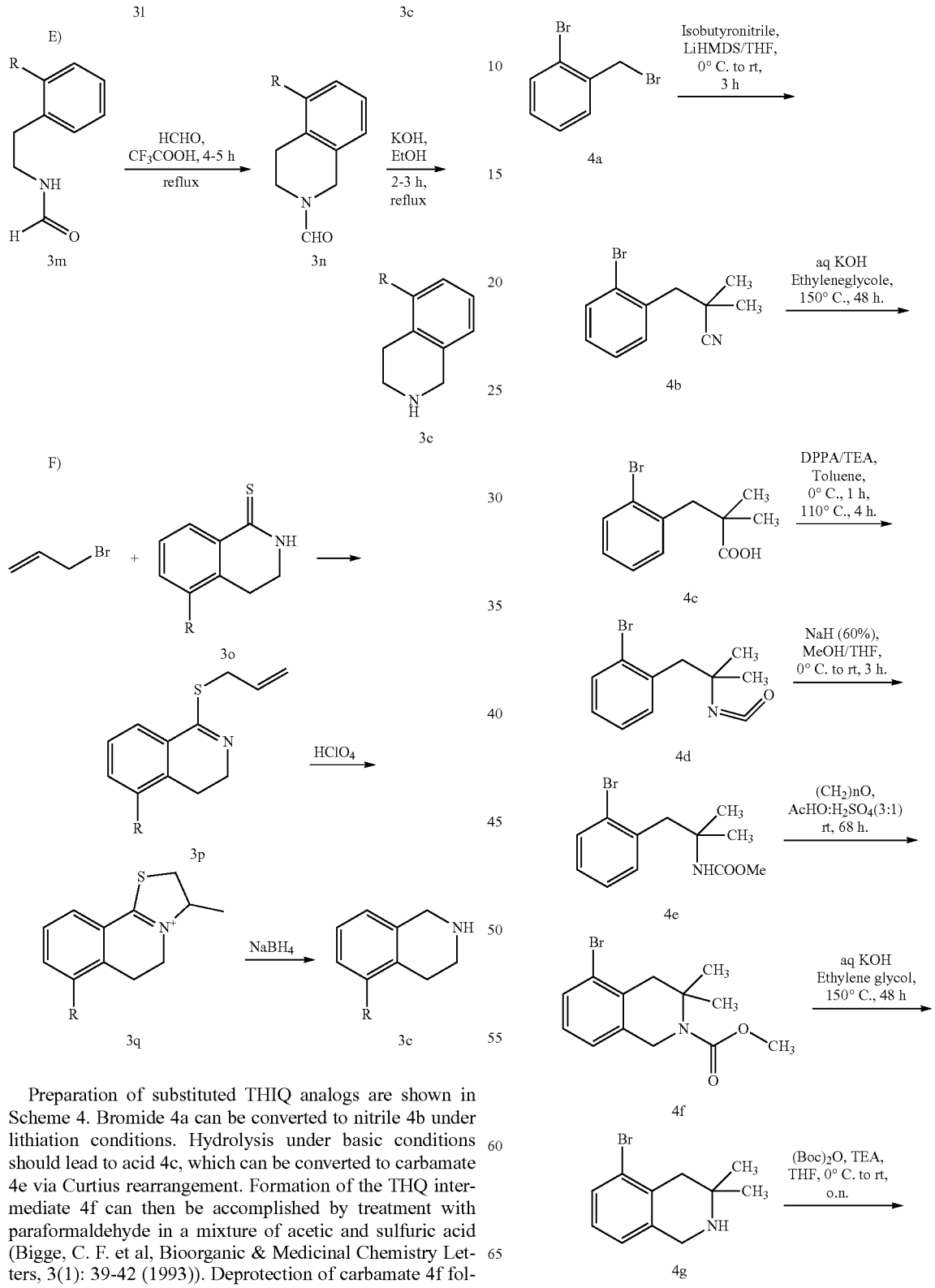

4h, which can be subjected to the Suzuki cross coupling reaction with an appropriate boronate or boronic acid or the Stille coupling procedures known to those in the art.

Preparation of substituted THIQ analogs are shown in Scheme 4. Bromide 4a can be converted to nitrile 4b under lithiation conditions. Hydrolysis under basic conditions should lead to acid 4c, which can be converted to carbamate 4e via Curtius rearrangement. Formation of the THQ intermediate 4f can then be accomplished by treatment with paraformaldehyde in a mixture of acetic and sulfuric acid (Bigge, C. F. et al, Bioorganic & Medicinal Chemistry Letters, 3(1): 39-42 (1993)). Deprotection of carbamate 4f followed by protection with Boc₂O should afford intermediate

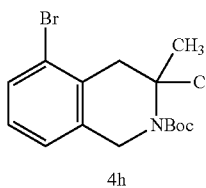

4h

Various heterocyclic THIQ intermediates can be easily obtained from their corresponding isoquinoline or isoquinolone analogs as shown in scheme 5.

Scheme 5:

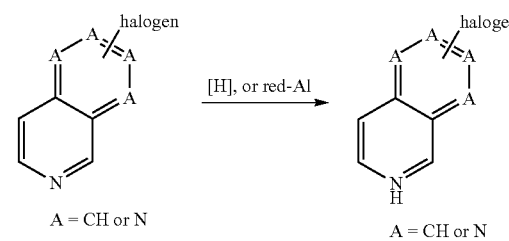

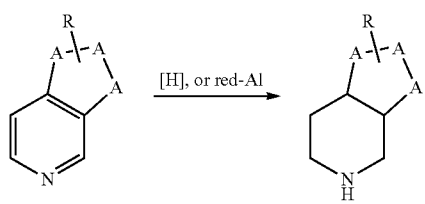

R = H or various substituents
A = CH or N or N-substituted

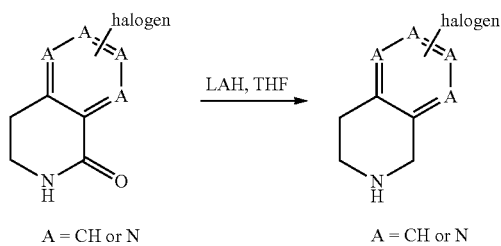

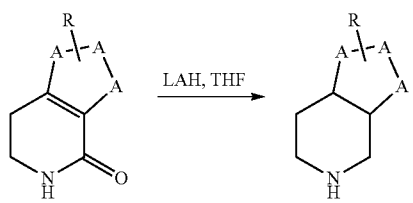

R = H or various substituents
A = CH or N or N-substituted

These in turn can be converted to compounds of this invention. All carboxylic acids used in this invention are obtained commercially or can be obtained by methods known by those in the art of synthetic organic chemistry.

Guanidines of this invention can be prepared by the methods shown in scheme 6.

Scheme 6:

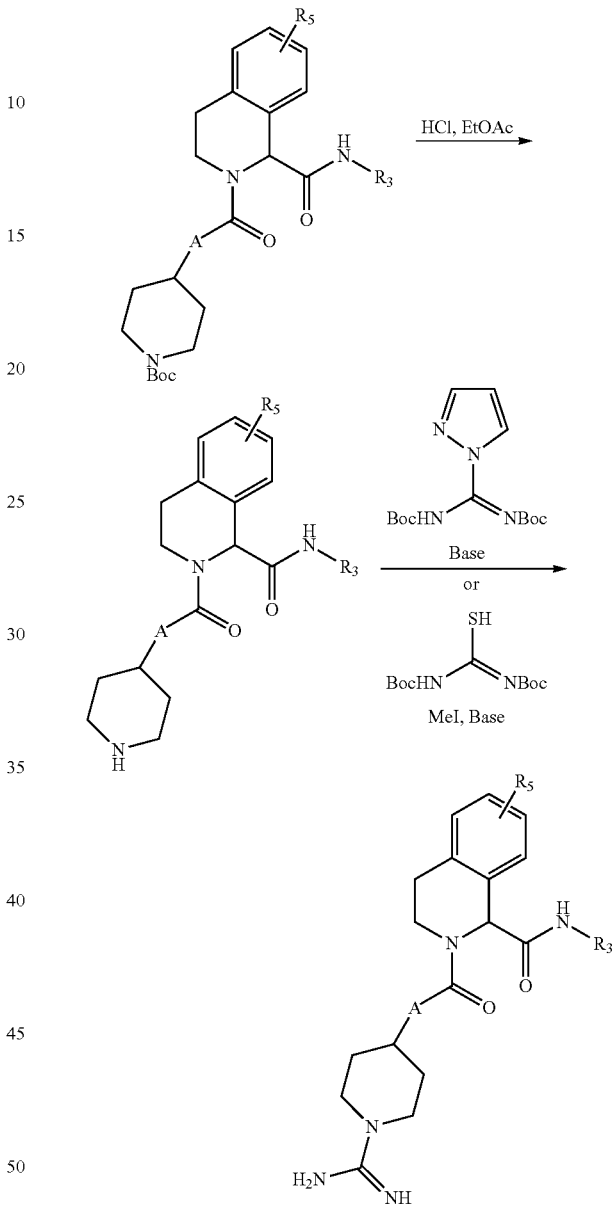

Purification of intermediates and final products was carried out via either normal or reverse phase chromatography. Normal phase chromatography was carried out using prepacked SiO$_2$ cartridges eluting with either gradients of hexanes and EtOAc or DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% ACN, 0.1% TFA) and Solvent B (10% water, 90% ACN, 0.1% TFA, UV 220 nm) or with gradients of Solvent A (98% water, 2% ACN, 0.05% TFA) and Solvent B (98% ACN, 2% water, 0.05% TFA, UV 220 nm).

Unless otherwise stated, analysis of final products was carried out by reverse phase analytical HPLC.

Method A: A majority of analytical HPLC runs were: Sun-Fire (4.6×150 mm) (15 min gradient-95:5 H$_2$O/ACN-to 95:5ACN/H$_2$O-0.05% TFA).

Method B: A minority of analytical HPLC runs were: Zorbax (4.6×75 mm) (8 min gradient-10:90 MeOH/H$_2$O to 90:10 MeOH/H$_2$O, 0.2% H$_3$PO$_4$)

A majority of mass spectra runs were run using Phenomenex Luna C18 (2×30 mm) (2 min gradient 90% H$_2$O/10% MeOH/0.1% TFA to 90% MeOH/10% H$_2$O/0.1% TFA)

Intermediate 1: tert-Butyl 4-isocyanobenzoate

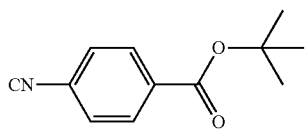

Intermediate 1A: tert-Butyl 4-formamidobenzoate: Combined tert-butyl 4-aminobenzoate (15.3 g, 79 mmol), DMAP (1.935 g, 15.84 mmol), N-methylmorpholine (15.67 mL, 143 mmol) in DCM (120 mL) and, after cooling to 0° C., slowly added formic acid (9.11 mL, 238 mmol). After stirring for 18 h, the reaction was concentrated and then partitioned with 1N HCl (100 mL) and EtOAc (200 mL). The aqueous layer was extracted with EtOAc (100 mL). The combined organic layers were washed with brine (50 mL) and dried (MgSO$_4$). The desired product was collected as yellow syrup (16 g).

Intermediate 1: To Intermediate 1A in THF (300 mL) was added TEA (33 mL, 238 mmol) and, after cooling to 0° C., POCl$_3$ (7.3 mL, 79 mmol) was slowly added and the reaction was stirred at room temperature. After 24 h, the reaction was partitioned between EtOAc (200 mL) and aqueous NaHCO$_3$ (100 mL). The aqueous layer was extracted with EtOAc (100 mL). The combined organic layers were washed with brine (50 mL) and dried (MgSO$_4$). Purification by normal phase chromatography afforded 10.4 g (64.6%) of Intermediate 1 as a green solid. $^1$H NMR (400 MHz, CDCl$_3$) δ 8.02 (d, J=8.59 Hz, 2H), 7.41 (d, J=8.34 Hz, 2H), 1.60 (s, 9H) ppm.

Intermediate 2: 3,4-dihydroisoquinoline

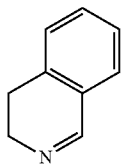

Intermediate 2: To 1,2,3,4-tetrahydroisoquinoline (1.175 ml, 9.39 mmol) in DCM (100 mL) was added manganese dioxide (13.05 g, 150 mmol). After 18 h, the reaction was filtered through Celite®, and the filter pad was washed with DCM and MeOH. The filtrate was concentrated to afford 0.98 g (80%) of Intermediate 1 as an amber oil. $^1$H NMR (400 MHz, CHLOROFORM-d) δ 8.34 (1H, s), 7.22-7.39 (3H, m), 7.07-7.20 (1H, m), 3.72-3.84 (2H, m), 2.67-2.82 (2H, m) ppm. MS (ESI) m/z: 132.0 (M+H)$^+$.

Intermediate 3: 5-(4-methoxypiperidin-1-yl)-3,4-dihydroisoquinoline

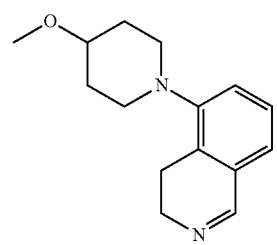 [SMILES: COC1CCN(c2cccc3c2CCN=C3)CC1]

Intermediate 3A: 5-(4-methoxypiperidin-1-yl)isoquinoline: To 5-bromoisoquinoline (10.40 g, 50 mmol), 4-methoxypiperidine (4.92 mL, 50.0 mmol), Pd$_2$(dba)$_3$ (0.458 g, 0.500 mmol), BINAP (0.934 g, 1.500 mmol), and t-BuONa (6.73 g, 70.0 mmol) was added degassed toluene (60 mL) and the reaction was heated under N$_2$ to 85° C. for 24 h and then to 105° C. for 3 h. The reaction mixture was cooled to ambient temperature and water was added. The phases were separated and the aqueous layer extracted three times with ethyl acetate. The combined organics were washed with brine, dried (Na$_2$SO$_4$), filtered and purified by silica gel chromatography to afford 6.34 g (52.4%) of Intermediate 3A as a pale yellow solid. MS (ESI) m/z: 243.2 (M+H)$^+$.

Intermediate 3B: 5-(4-methoxypiperidin-1-yl)-1,2,3,4-tetrahydroisoquinoline: Intermediate 3A (6.344 g, 26.2 mmol) in EtOH (100 mL) was hydrogenated at 55 psi in the presence of platinum(IV) oxide (0.595 g, 2.62 mmol) for 74 h. The reaction mixture was filtered through Celite® and the filtrate was evaporated to 6.37 g (94%) of a dark residue for Intermediate 3B. MS (ESI) m/z: 247.2 (M+H)$^+$.

Intermediate 3: Intermediate 3B was oxidized as described for Intermediate 2 to afford 6.32 g (100%) of Intermediate 3 as a yellow viscous oil. MS (ESI) m/z: 245.2 (M+H)$^+$.

Intermediate 4: 5-bromo-2-(tert-butoxycarbonyl)-1,2,3,4-tetrahydroisoquinoline-1-carboxylic acid

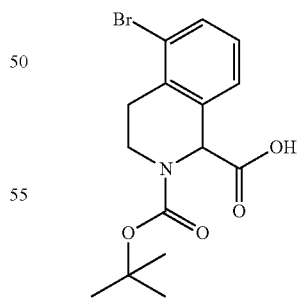

Intermediate 4A: methyl 5-bromo-1,2,3,4-tetrahydroisoquinoline-1-carboxylate: 5-Bromo-2-(ethoxycarbonyl)-1,2,3,4-tetrahydroisoquinoline-1-carboxylic acid (1 g, 3.05 mmol) (Ortwine, et al., J. Med. Chem, 1992, 35, 1345), in two batches, was heated in a microwave to 150° C. in 1,4-dioxane (4 mL)/EtOH (2 mL)/2N NaOH (5 mL) for a total of 3 h. The combined reaction mixtures were concentrated, dissolved in MeOH (30 mL) and thionyl chloride (0.222 mL, 3.05 mmol) was slowly added. After 18 h, the solvent was removed and the residue was partitioned with EtOAc (50 mL)/saturated NaHCO₃ (30 mL), phases separated and aqueous layer was extracted with EtOAc (2×25 mL). The combined organic layers were washed with brine (25 mL) and dried (MgSO₄) to afford 0.56 g (80%) of Intermediate 4A as a yellow oil. MS (ESI) m/z: 270-272 (M+H)$^+$.

Intermediate 4B: 2-tert-butyl 1-methyl 5-bromo-3,4-dihydroisoquinoline-1,2(1H)-dicarboxylate: To crude Intermediate 4A (0.65 g, 2.406 mmol) in DCM (10 mL) and NaHCO₃ (0.404 g, 4.81 mmol) was added di-tert-butyl dicarbonate (0.670 mL, 2.89 mmol). After 24 h, the reaction was quenched with water (20 mL) and extracted with DCM (3×30 mL). The combined organic layers were washed with brine (15 mL) and dried (MgSO₄). Purification by silica gel chromatography afforded 0.63 g (70.7%) of Intermediate 4B as a clear oil. MS (ESI) m/z: 391.9 (M+Na)$^+$.

Intermediate 4: To a solution of Intermediate 4B (5.0 g, 13.50 mmol) in THF (60 mL)/MeOH (60 mL) was added 1N NaOH (40.5 ml, 40.5 mmol). After 24 h, the reaction mixture was concentrated and the remaining aqueous layer cooled to 0° C. and the pH was adjusted to 5 using 1.0N HCl solution. The solution was extracted with EtOAc (3×75 mL). The combined organic extracts were washed with brine, dried (MgSO₄), filtered, and concentrated to give 4.75 g (99%) of Intermediate 4 as a white solid. $^1$H NMR (500 MHz, DMSO-d6) δ 7.55 (dd, J=17.2, 7.8 Hz, 2H), 7.20 (t, J=7.8 Hz, 1H), 5.49-5.32 (m, 1H), 3.86-3.73 (m, 1H), 3.59-3.48 (m, 1H), 2.92-2.74 (m, 2H), 1.42 (d, J=12.9 Hz, 9H) ppm. MS (ESI) m/z: 255.9 (M+H-tBoc)$^+$.

Intermediate 5: 1-(3,4-dihydroisoquinolin-5-yl)-4-methylpiperazin-2-one

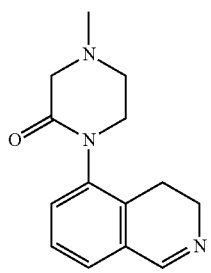 [SMILES: CN1CCN(c2cccc3c2CCN=C3)C(=O)C1]

5A: 1-(isoquinolin-5-yl)-4-methylpiperazin-2-one: To 5-bromoisoquinoline (1.657 g, 7.96 mmol) and 4-methylpiperazin-2-one (1, 8.76 mmol) was added DMSO (7 mL), 1,10-phenanthroline (0.144 g, 0.796 mmol), potassium carbonate (3.30 g, 23.89 mmol) and the mixture was degassed with Ar for 30 min. Copper(I)iodide (1.213 g, 6.37 mmol) was added and the reaction was heated in oil bath at 130° C. overnight. The reaction was cooled to room temperature and quenched with NH₄OH (10 mL) and water (20 mL) and diluted with EtOAc. The aqueous layer was extracted EtOAc (2×50 mL) and then, nBuOH (1×30 mL). Combined organic layers were washed with brine and dried (MgSO₄). Purification by silica gel chromatography afforded 1.5 g (78%) yellow solid. MS (ESI) m/z: 242.0 (M+H)$^+$.

Intermediate 5 was prepared from 5A (1.5 g, 6.22 mmol) in a similar manner as Intermediate 3 to afford 1.34 g (89%) of a dark oil. MS (ESI) m/z: 244.1 (M+H)$^+$.

Example 1

4-(5-bromo-2-(5-carbamimidoyl-4,5,6,7-tetrahydrothiazolo[5,4-c]pyridine-2-carbonyl)-1,2,3,4-tetrahydroisoquinoline-1-carboxamido)benzoic acid, TFA Salt

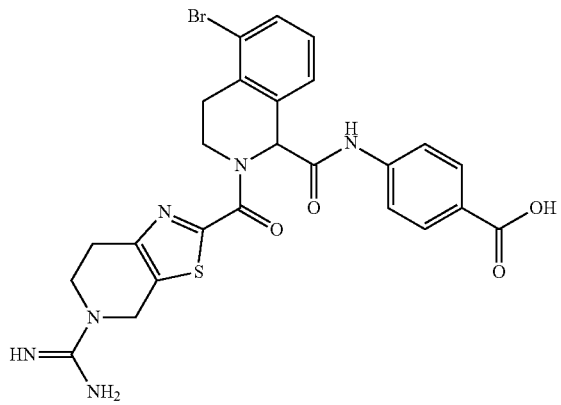 [SMILES: N=C(N)N1CCc2nc(C(=O)N3CCc4c(Br)cccc4C3C(=O)Nc3ccc(C(=O)O)cc3)sc2C1]

1A. tert-Butyl 5-bromo-1-((4-(tert-butoxycarbonyl)phenyl)carbamoyl)-3,4-dihydroisoquinoline-2(1H)-carboxylate: Phosphorus oxychloride (1.89 g, 12.35 mmol) was added to Intermediate 4 (4.0 g, 11.23 mmol) and tert-butyl 4-aminobenzoate (2.17 g, 11.23 mmol) in pyridine (44.9 ml) at 0° C. After 2 h, the reaction was quenched with saturated NH₄Cl (50 mL). The solution was extracted with EtOAc (3×100 mL). The combined organic layer was washed several times with 1.0N HCl solution, water, brine, dried over sodium sulfate, filtered, and concentrated to give 1A as a tan solid. MS (ESI) m/z: 531/533 (Br isotope) (M+H)$^+$.

1B. tert-Butyl 4-(5-bromo-1,2,3,4-tetrahydroisoquinoline-1-carboxamido)benzoate hydrochloride: 1A (1.0 g, 1.88 mmol) dissolved in THF (10 mL) was treated with HCl (4.0M in dioxane) (3.29 ml, 13.17 mmol). After stirring for 12 h, the precipitate was collected by filtration and washed with Et₂O. 1B was recovered as a white solid (0.514 g, 1.099 mmol, 58.4% yield). MS (ESI) m/z: 431/433 (Br isotope) (M+H)$^+$.

1C. (Z)-Ethyl 5-(N,N'-bis(tert-butoxycarbonyl)carbamimidoyl)-4,5,6,7-tetrahydrothiazolo[5,4-c]pyridine-2-carboxylate: 5-tert-Butyl 2-ethyl 6,7-dihydrothiazolo[5,4-c]pyridine-2,5(4H)-dicarboxylate (0.500 g, 1.601 mmol) was treated with HCl (4.0M in dioxane) (20.01 ml, 80 mmol) at room temperature. After 1 h, the precipitate was filtered, washed with Et₂O, and dried in vacuo. The amine hydrochloride salt was dissolved in DMF (10 mL) and treated with DIPEA (1.677 ml, 9.60 mmol) and (E)-tert-butyl(((tert-butoxycarbonyl)amino)(1H-pyrazol-1-yl)methylene)carbamate (0.497 g, 1.601 mmol). After 14 h, the reaction mixture was taken up in EtOAc (50 mL) and washed with water. The water layer was extracted with additional EtOAc. The combined organic layers were washed with 1.0M HCl solution, water, brine, dried over sodium sulfate, filtered, and concentrated. The crude material was purified by column chromatography to give 1C (0.282 g, 38.8% yield) as a white solid. MS (ESI) m/z: 455 (M+H)$^+$.

1D. (Z)-5-(N,N'-bis(tert-butoxycarbonyl)carbamimidoyl)-4,5,6,7-tetrahydrothiazolo[5,4-c]pyridine-2-carboxylic acid: Lithium hydroxide monohydrate (0.076 g, 1.82 mmol) was added to a solution of 1C (0.275 g, 0.605 mmol) in THF/MeOH/H$_2$O (1/1/1; 15 mL). The mixture stirred at 50° C. for 14 h. The organics were removed and the remaining aqueous layer made acidic with 1.0N HCl solution. This solution was extracted with EtOAc, washed with water, brine, dried over sodium sulfate, filtered, and concentrated to give 1D (139 mg, 53.9% yield) as a white solid. MS (ESI) m/z: 427 (M+H)$^+$.

Example 1

4-(5-Bromo-2-(5-carbamimidoyl-4,5,6,7-tetrahydrothiazolo[5,4-c]pyridine-2-carbonyl)-1,2,3,4-tetrahydroisoquinoline-1-carboxamido)benzoic acid DIPEA (0.017 ml, 0.096 mmol) was added to a solution of 1B (0.015 g, 0.032 mmol), 1D (0.014 g, 0.032 mmol), EDC (9.22 mg, 0.048 mmol), and 1-hydroxybenzotriazole hydrate (7.37 mg, 0.048 mmol) in DMF (1 mL) and stirred for 20 h. The reaction mixture was partitioned between water and EtOAc. The organic layer was washed with 1.0M HCl solution, water, brine, dried over sodium sulfate, filtered, and concentrated. The residue was treated with 50% TFA/DCM for 1 h, concentrated, and purified by reverse phase prep HPLC and freeze-dried to afford 3.2 mg (11.2%) of Example 1 as a white solid. $^1$H NMR: (500 MHz, METHANOL-d$_4$) δ: 7.90-7.86 (m, 2H), 7.61-7.55 (m, 2H), 7.50 (d, J=8.0 Hz, 1H), 7.45 (d, J=7.7 Hz, 1H), 7.15-7.07 (m, 1H), 5.85 (s, 1H), 4.64-4.59 (m, 1H), 4.12-3.91 (m, 1H), 3.84-3.72 (m, 2H), 3.18-2.96 (m, 4H) ppm. MS (ESI) m/z: 583/585 (Br isotope) (M+H)$^+$. Analytical HPLC: RT=6.63 min.

Example 2

4-(5-bromo-2-(2-carbamimidoyl-1,2,3,4-tetrahydroisoquinoline-6-carbonyl)-1,2,3,4-tetrahydroisoquinoline-1-carboxamido)benzoic acid, TFA salt

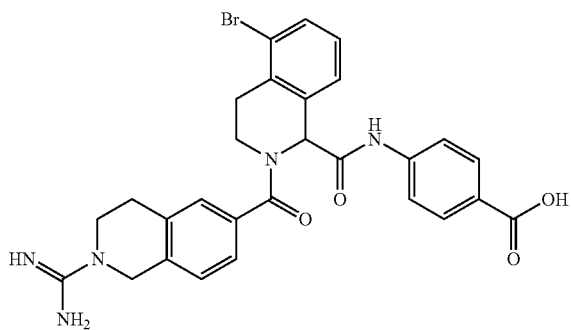 [SMILES: N=C(N)N1CCc2cc(C(=O)N3CCc4c(Br)cccc4C3C(=O)Nc3ccc(C(=O)O)cc3)ccc2C1]

Example 2. DIPEA (0.112 ml, 0.641 mmol) was added to a solution of Example 1B (0.100 g, 0.214 mmol), 2-(tert-butoxycarbonyl)-1,2,3,4-tetrahydroisoquinoline-6-carboxylic acid (0.059 g, 0.214 mmol), EDC (0.061 g, 0.321 mmol), and 1-hydroxybenzotriazole hydrate (0.049 g, 0.321 mmol) in DMF (3 mL). After 14 h, the reaction mixture was partitioned between water and EtOAc. The water layer was extracted with additional EtOAc. The combined organic layer was washed with brine, dried over sodium sulfate, filtered and concentrated. The residue was treated with HCl (4.0M in dioxane) (0.267 ml, 1.069 mmol) at room temperature. After 4 h, the reaction mixture was concentrated and the salt was combined with (Z)-tert-butyl(((tert-butoxycarbonyl)amino)(1H-pyrazol-1-yl)methylene)carbamate (0.080 g, 0.257 mmol) and DIPEA (0.224 ml, 1.283 mmol) in DMF (3 mL) and stirred for 18 h. The reaction mixture was partitioned between water and EtOAc. The organic layer was washed with 1.0M HCl solution, water, brine, dried over sodium sulfate, filtered, and concentrated. The residue was treated with 50% TFA/DCM for 1 h, concentrated, and purified by reverse phase preparative HPLC to give Example 2 as a white solid (15 mg, 8.2%). $^1$H NMR: (500 MHz, METHANOL-d$_4$) δ: 8.01 (d, J=8.8 Hz, 2H), 7.72 (d, J=8.3 Hz, 2H), 7.64-7.56 (m, 2H), 7.45 (br. s., 2H), 7.37 (d, J=8.3 Hz, 1H), 7.24 (t, J=7.8 Hz, 1H), 5.99 (s, 1H), 4.69 (s, 2H), 4.06 (d, J=4.7 Hz, 1H), 3.85-3.77 (m, 1H), 3.74-3.61 (m, 2H), 3.25-3.16 (m, 1H), 3.13-3.01 (m, 3H) ppm. MS (ESI) m/z: 576/578 (Br isotope) (M+H)$^+$. Analytical HPLC: RT=6.52 min.

Example 3

4-(5-bromo-2-(2-carbamimidoyl-1,2,3,4-tetrahydroisoquinoline-7-carbonyl)-1,2,3,4-tetrahydroisoquinoline-1-carboxamido)benzoic acid, TFA Salt

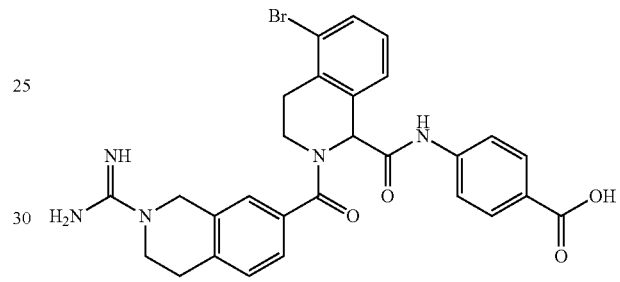

Example 3 was made in the same way as Example 2 by using 2-(tert-butoxycarbonyl)-1,2,3,4-tetrahydroisoquinoline-7-carboxylic acid instead of 2-(tert-butoxycarbonyl)-1,2,3,4-tetrahydroisoquinoline-6-carboxylic acid. $^1$H NMR: (500 MHz, METHANOL-d$_4$) δ: 8.01 (d, J=8.8 Hz, 2H), 7.73 (d, J=8.5 Hz, 2H), 7.65-7.56 (m, 2H), 7.50-7.46 (m, 1H), 7.45-7.38 (m, 2H), 7.25 (t, J=7.7 Hz, 1H), 5.98 (s, 1H), 4.75-4.62 (m, 2H), 4.12-4.02 (m, 1H), 3.85-3.78 (m, 1H), 3.71 (t, J=5.5 Hz, 2H), 3.25-3.16 (m, 1H), 3.12-3.01 (m, 3H) ppm. MS (ESI) m/z: 576/578 (Br isotope) (M+H)$^+$. Analytical HPLC: RT=5.09 min.

Example 4

4-(5-bromo-2-(6-carbamimidoyl-4,5,6,7-tetrahydrothieno[2,3-c]pyridine-3-carbonyl)-1,2,3,4-tetrahydroisoquinoline-1-carboxamido)benzoic acid, TFA salt

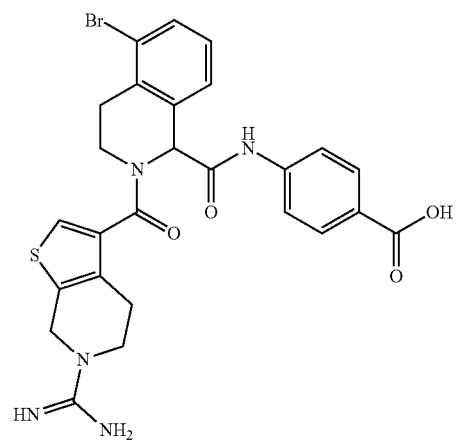 [SMILES: N=C(N)N1CCc2c(C(=O)N3CCc4c(Br)cccc4C3C(=O)Nc3ccc(C(=O)O)cc3)csc2C1]

Example 4 was made in the same way as Example 2 by using 6-(tert-butoxycarbonyl)-4,5,6,7-tetrahydrothieno[2,3-c]pyridine-3-carboxylic acid instead of 2-(tert-butoxycarbonyl)-1,2,3,4-tetrahydroisoquinoline-6-carboxylic acid. $^1$H NMR: (500 MHz, METHANOL-d$_4$) δ: 8.02-7.98 (m, 2H), 7.71 (m, 3H), 7.63-7.57 (m, 2H), 7.24 (t, J=7.7 Hz, 1H), 5.96 (br. s., 1H), 4.81-4.71 (m, 2H), 4.14-4.10 (m, 1H), 3.83-3.78 (m, 2H), 3.77-3.71 (m, 1H), 3.24-3.20 (m, 1H), 3.14-3.06 (m, 1H), 2.97-2.90 (m, 1H), 2.85-2.76 (m, 1H) ppm. MS (ESI) m/z: 582/584 (Br isotope) (M+H)$^+$. Analytical HPLC: RT=6.53 min.

Example 5

4-(2-(5-carbamimidoyl-4,5,6,7-tetrahydrothiazolo[5,4-c]pyridine-2-carbonyl)-5-(4-methoxypiperidin-1-yl)-1,2,3,4-tetrahydroisoquinoline-1-carboxamido) benzoic acid, TFA salt

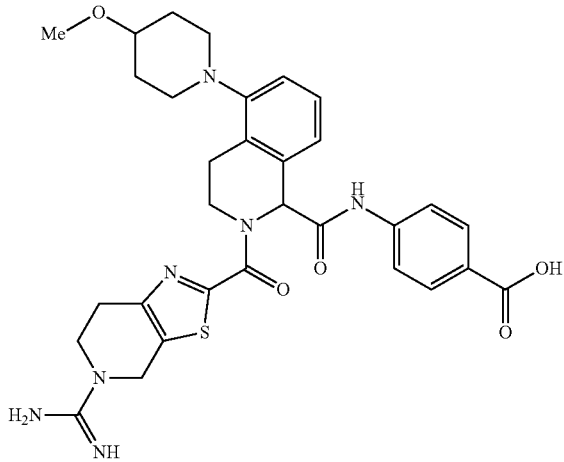 [SMILES: COC1CCN(c2cccc3c2CCN(C(=O)c2nc4c(s2)CN(C(=N)N)CC4)C3C(=O)Nc2ccc(C(=O)O)cc2)CC1]

Example 5. 1D (0.087 g, 0.205 mmol), Intermediate 3 (0.050 g, 0.205 mmol), and Intermediate 1 (0.042 g, 0.205 mmol) were added to MeOH (0.409 ml) and heated at 50° C. overnight. The reaction mixture was partitioned between water and EtOAc. The aqueous layer was extracted with additional EtOAc (2×). The combined organic layer was washed with brine, dried over sodium sulfate, filtered, and concentrated. The residue was treated with 50% TFA/DCM for 2 h, concentrated and purified by reverse phase preparative HPLC to give Example 5 (0.038 gram, 17.4%) as a light yellow solid. $^1$H NMR: (400 MHz, DMSO-d$_6$) δ: 10.80 (s, 1H), 7.84-7.78 (m, 2H), 7.66-7.51 (m, 5H), 7.30 (d, J=7.7 Hz, 1H), 7.19-7.12 (m, 1H), 6.94 (d, J=8.2 Hz, 1H), 5.75 (s, 1H), 4.89-4.81 (m, 1H), 4.78-4.68 (m, 2H), 3.97 (d, J=3.8 Hz, 1H), 3.79-3.74 (m, 1H), 3.31-3.16 (m, 4H), 3.04-2.86 (m, 6H), 2.71-2.51 (m, 3H), 1.95-1.86 (m, 2H), 1.54 (d, J=7.7 Hz, 2H) ppm. MS (ESI) m/z: 618 (M+H)$^+$. Analytical HPLC: RT=5.23 min (method B).

Example 6

(S)-4-(2-(2-carbamimidoyl-2-azaspiro[3.3]heptane-6-carbonyl)-1,2,3,4-tetrahydroisoquinoline-1-carboxamido)benzoic acid, bis-TFA Salt

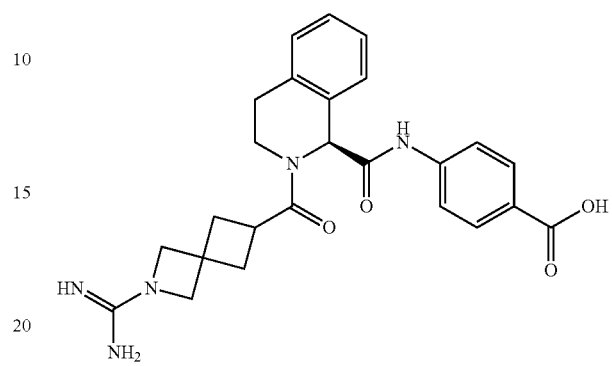

6A: (S)-(9H-fluoren-9-yl)methyl 1-((4-(tert-butoxycarbonyl)phenyl)carbamoyl)-3,4-dihydroisoquinoline-2(1H)-carboxylate: To (S)-2-(((9H-fluoren-9-yl)methoxy)carbonyl)-1,2,3,4-tetrahydroisoquinoline-1-carboxylic acid (0.46 g, 1.152 mmol) and tert-butyl 4-aminobenzoate (0.267 g, 1.382 mmol) in DCM (8 mL), cooled in ice bath, was added pyridine (0.466 ml, 5.76 mmol) and POCl$_3$ (0.107 ml, 1.152 mmol). After 3h, the reaction was diluted with EtOAc (30 mL), quenched with 0.5 N HCl (10 mL) and extracted with EtOAc (30 mL). The combined organic layers were washed with saturated NaHCO$_3$(10 mL), brine (10 mL) and dried (MgSO$_4$). Purification by silica gel column chromatography afforded 0.5 g (80%) of 6A as a clear film. MS (ESI) m/z: 575.2 (M+H)$^+$.

6B: (S)-tert-Butyl 4-(1,2,3,4-tetrahydroisoquinoline-1-carboxamido)benzoate, TFA: To 6A in 1 mL DMF, at 0° C., was added 1 mL 30% piperidine in DMF. After 40 min, the reaction was quenched with water (10 mL) and extracted with ethyl acetate (3×10 mL). The combined organic layers were washed with brine (10 mL) and dried (MgSO$_4$). Purification by reverse phase HPLC and freeze-dying afforded 0.25 g (61%) of 6B as a white solid. MS (ESI) m/z: 353.1 (M+H)$^+$.

6C: (S)-tert-Butyl 6-(1-((4-(tert-butoxycarbonyl)phenyl)carbamoyl)-1,2,3,4-tetrahydroisoquinoline-2-carbonyl)-2-azaspiro[3.3]heptane-2-carboxylate: 6B (27 mg, 0.058 mmol), 2-(tert-butoxycarbonyl)-2-azaspiro[3.3]heptane-6-carboxylic acid (13.97 mg, 0.058 mmol), EDC (11.10 mg, 0.058 mmol), and HOBT (8.86 mg, 0.058 mmol) were combined in DMF (0.8 mL) and Hunig's base (0.061 mL, 0.347 mmol) was added. After 24 h, the reaction was partitioned with water (10 mL) and ethyl acetate (10 mL). The aqueous layer was extracted with ethyl acetate (1×5 mL). The combined organic layers were washed with brine (10 mL) and dried (MgSO$_4$) and the crude material was carried onto the next step. MS (ESI) m/z: 576.2 (M+H)$^+$.

Example 6

6C was deprotected in 50% TFA/DCM (3 mL) for 2h. MS (ESI) m/z: 420.0 (M+H)$^+$. The solvents were removed and the TFA salt was combined with Hunig's Base (0.061 mL, 0.347 mmol) and 1H-pyrazole-1-carboximidamide, HCl (8.48 mg, 0.058 mmol) in DMF (0.8 mL). After 24 h, the reaction mixture was acidified with TFA, filtered, purified by reverse phase HPLC and freeze-dried to afford 18 mgs (42%) of Example 6 as a white solid. ¹H NMR (400 MHz, METHANOL-d4) δ: 8.07-7.91 (m, 2H), 7.73-7.62 (m, 2H), 7.62-7.50 (m, 1H), 7.40-7.18 (m, 3H), 5.76 (s, 1H), 4.19 (s, 2H), 4.11-3.94 (m, 3H), 3.63-3.44 (m, 2H), 3.29-3.20 (m, 1H), 2.97-2.82 (m, 1H), 2.72-2.42 (m, 4H) ppm. MS (ESI) m/z: 462.0 (M+H)⁺. Analytical HPLC: RT=4.71 min.

Example 7

(S)-4-(2-(3-azaspiro[5.5]undecane-9-carbonyl)-1,2,3,4-tetrahydroisoquinoline-1-carboxamido)benzoic acid, TFA

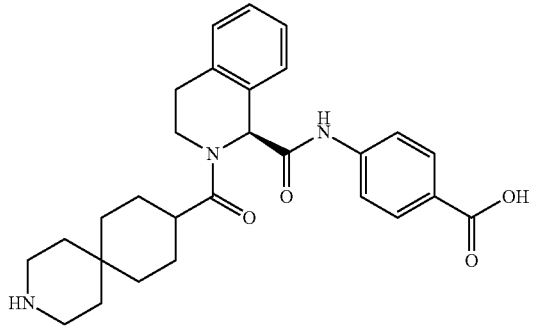 [SMILES: O=C(O)c1ccc(NC(=O)[C@@H]2c3ccccc3CCN2C(=O)C2CCC3(CCNCC3)CC2)cc1]

Example 7

3-(tert-butoxycarbonyl)-3-azaspiro[5.5]undecane-9-carboxylic acid (16.58 mg, 0.056 mmol), 6B (26 mg, 0.056 mmol), EDC-HCl (10.69 mg, 0.056 mmol), HOBT (8.54 mg, 0.056 mmol), were combined in DMF (0.8 mL) and Hunig's Base (0.058 mL, 0.334 mmol) was added. After 24 h, MS indicated (ESI) m/z: 576.2 (M+H-tButyl)⁺, and the reaction was partitioned with water (10 mL) and ethyl acetate (10 mL). The aqueous layer was extracted with ethyl acetate (1×5 mL). The combined organic layers were washed with brine (10 mL) and dried (MgSO₄). To the crude residue was added 50% TFA/DCM (3 mL). After 2 h, the reaction was concentrated and to the residue was added 0.8 mL DMF, approximately 0.5 mL of this mixture was carried onto Example 8 and 0.25 mL was purified by reverse phase HPLC and freeze-dried to afford 5.8 mgs (43%) of Example 7 as a white solid. ¹H NMR (400 MHz, METHANOL-d4) δ: 8.03-7.91 (m, 2H), 7.66 (dd, J=8.8, 1.5 Hz, 2H), 7.54 (dd, J=5.2, 2.7 Hz, 1H), 7.38-7.20 (m, 3H), 5.78 (s, 1H), 4.30-4.15 (m, 1H), 3.81-3.63 (m, 1H), 3.31-3.24 (m, 1H), 3.17 (dt, J=11.4, 5.8 Hz, 4H), 3.00-2.78 (m, 2H), 1.94-1.75 (m, 5H), 1.75-1.57 (m, 5H), 1.46-1.30 (m, 2H) ppm. MS (ESI) m/z: 476.1 (M+H)⁺. Analytical HPLC: RT=5.4 min.

Example 8

(S)-4-(2-(3-carbamimidoyl-3-azaspiro[5.5]undecane-9-carbonyl)-1,2,3,4-tetrahydroisoquinoline-1-carboxamido)benzoic acid, bis-TFA Salt

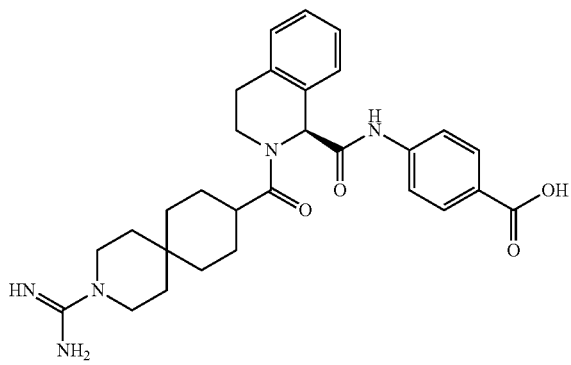 [SMILES: N=C(N)N1CCC2(CCC(C(=O)N3CCc4ccccc4[C@H]3C(=O)Nc3ccc(C(=O)O)cc3)CC2)CC1]

Example 8

To a solution of Example 7 in DMF (0.55 mL) was added 1H-pyrazole-1-carboximidamide, HCl (4.62 mg, 0.032 mmol) and Hunig's Base (33.1 μl, 0.189 mmol). After 24 h, the reaction mixture was acidified with TFA, filtered and after purification by reverse phase HPLC and freeze-drying afforded 6.8 mgs (27.5%) of Example 8 as a white solid. ¹H NMR (400 MHz, METHANOL-d4) δ: 8.07-7.90 (m, 2H), 7.66 (dd, J=8.6, 1.5 Hz, 2H), 7.54 (dd, J=5.3, 2.5 Hz, 1H), 7.37-7.15 (m, 3H), 5.78 (s, 1H), 4.29-4.11 (m, 1H), 3.74 (ddd, J=12.3, 8.7, 4.0 Hz, 1H), 3.56-3.39 (m, 4H), 3.30-3.25 (m, 1H), 3.01-2.75 (m, 2H), 1.91-1.60 (m, 8H), 1.54-1.44 (m, 2H), 1.41-1.21 (m, 2H) ppm. MS (ESI) m/z: 518.1 (M+H)⁺. Analytical HPLC: RT=6.21 min.

Example 9

4-(2-(7-carbamimidoyl-7-azaspiro[3.5]nonane-2-carbonyl)-1,2,3,4-tetrahydroisoquinoline-1-carboxamido)benzoic acid, bis TFA Salt

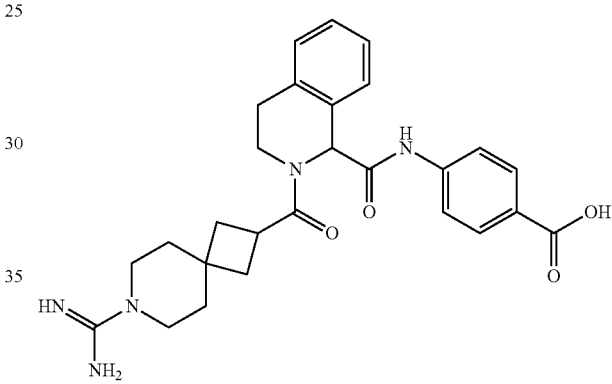

9A. tert-Butyl 2-(1-((4-(tert-butoxycarbonyl)phenyl)carbamoyl)-1,2,3,4-tetrahydroisoquinoline-2-carbonyl)-7-azaspiro[3.5]nonane-7-carboxylate: In a vial, 7-(tert-butoxycarbonyl)-7-azaspiro[3.5]nonane-2-carboxylic acid (49.3 mg, 0.183 mmol), Intermediate 2 (24 mg, 0.183 mmol), and MeOH (457 μl), were combined and, after stirring for 10 min, Intermediate 1 (37.2 mg, 0.183 mmol) was added and the reaction was heated to 50° C. After 24 h, the reaction was concentrated and carried directly onto the next step. MS (ESI) m/z: 548.3 (M+H-tbutyl)⁺.

Example 9

9A was deprotected by treatment with 50% TFA/DCM (2 mL) for 1 h. MS (ESI) m/z: 448.2 (M+H)⁺. The resultant TFA salt was dissolved in DMF (0.5 mL), then added Hunig's Base (192 μl, 1.098 mmol), and 1H-pyrazole-1-carboximidamide, HCl (26.8 mg, 0.183 mmol) and this procedure was repeated using excess Hunig's Base (1 mL), followed by purification by reverse phase HPLC and freeze-drying to afford 31 mgs (22.6%) of Example 9 as a white solid. ¹H NMR (400 MHz, METHANOL-d4) δ: 8.07-7.93 (m, 2H), 7.76-7.62 (m, 2H), 7.61-7.47 (m, 1H), 7.39-7.14 (m, 3H), 5.78 (s, 1H), 4.12-3.97 (m, 1H), 3.66-3.51 (m, 2H), 3.53-3.44 (m, 1H), 3.37 (d, J=5.3 Hz, 2H), 3.30-3.20 (m, 1H), 2.94-2.84 (m, 1H), 2.41-2.09 (m, 4H), 1.87-1.72 (m, 2H), 1.70-1.55 (m, 2H) ppm. MS (ESI) m/z: 490.1 (M+H)⁺. Analytical HPLC: RT=5.63 min.

Example 10
(S)-4-(2-(7-carbamimidoyl-7-azaspiro[3.5]nonane-2-carbonyl)-1,2,3,4-tetrahydroisoquinoline-1-carboxamido)benzoic acid, TFA salt

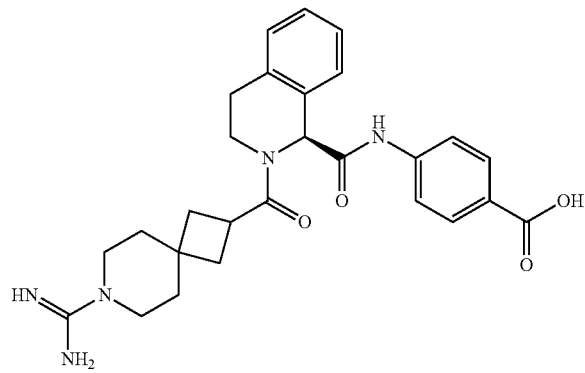 [SMILES: N=C(N)N1CCC2(CC1)CC(C(=O)N1CCc3ccccc3[C@H]1C(=O)Nc1ccc(C(=O)O)cc1)C2]

10A. tert-Butyl 4-(2-(7-azaspiro[3.5]nonane-2-carbonyl)-1,2,3,4-tetrahydroisoquinoline-1-carboxamido)benzoate, HCl. 9A (0.38 g, 1.10 mmol) was dissolved in THF (6 mL) and treated with HCl (2.86 ml, 11.44 mmol). After stirring for a total of 6 h, the reaction mixture was concentrated and carried forward as is. MS (ESI) m/z: 504.1 (M+H)$^+$.

10B. (S,E)-tert-Butyl 4-(2-(7-(N,N'-bis(tert-butoxycarbonyl)carbamimidoyl)-7-azaspiro[3.5]nonane-2-carbonyl)-1,2,3,4-tetrahydroisoquinoline-1-carboxamido)benzoate: 10A (0.6 g, 0.77 mmol) was treated as described in Example 9 using (Z)-tert-butyl(((tert-butoxycarbonyl)amino)(1H-pyrazol-1-yl)methylene)carbamate to afford 0.17 g of 10B (30.9%) as a solid. This procedure was repeated to afford a total of 0.4 g of 10B. MS (ESI) m/z: 746.3 (M+H)$^+$.

Example 10

The racemate 10B (0.4 g, 0.536 mmol) was subjected to chiral SFC separation using a Chiralcel OJ-H column (30× 250 mm ID, 5 mM) and a mixture of 15% i-PrOH and 85% CO$_2$ with a flow rate of 80 mL/min and 100 bar at 40° C. Each separated enantiomer was concentrated separately and the resulting solid placed under vacuum overnight. The early eluting enantiomer (0.117 g, 0.157 mmol) was treated with 50% TFA/DCM. After 2 h, the reaction mixture was concentrated and the crude material purified by reverse phase preparative HPLC to give Example 10 (0.041 g, 43.6%) as a white solid. $^1$H NMR (500 MHz, METHANOL-d$_4$) δ: 8.02-7.97 (m, 2H), 7.72-7.68 (m, 2H), 7.58-7.54 (m, 1H), 7.32-7.27 (m, 3H), 5.79 (s, 1H), 4.05 (ddd, J=12.0, 6.1, 4.7 Hz, 1H), 3.63-3.56 (m, 2H), 3.52-3.47 (m, 2H), 3.42-3.37 (m, 2H), 3.32-3.24 (m, 1H), 2.95-2.89 (m, 1H), 2.30 (ddd, J=11.6, 9.4, 2.2 Hz, 1H), 2.24-2.16 (m, 3H), 1.86-1.82 (m, 2H), 1.68-1.63 (m, 2H) ppm. MS (ESI) m/z: 490 (M+H)$^+$. Analytical HPLC: RT=5.96 min.

Example 11
(R)-4-(2-(7-carbamimidoyl-7-azaspiro[3.5]nonane-2-carbonyl)-1,2,3,4-tetrahydroisoquinoline-1-carboxamido)benzoic acid, TFA salt

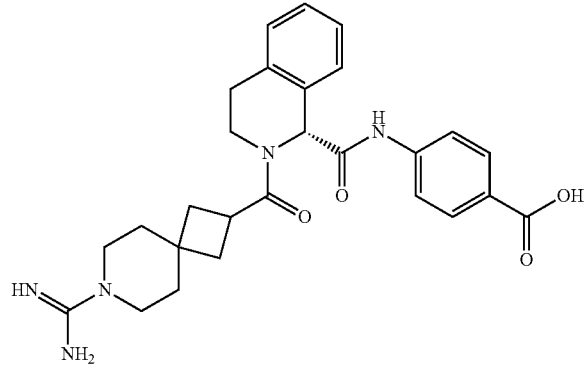 [SMILES: N=C(N)N1CCC2(CC1)CC(C(=O)N1CCc3ccccc3[C@@H]1C(=O)Nc1ccc(C(=O)O)cc1)C2]

Example 11

The second eluting enantiomer described in Example 10 (0.081 gram, 0.109 mmol) was treated with 50% TFA/DCM. After 2 h, the reaction mixture was concentrated and the crude material purified by reverse phase preparative HPLC to give Example 11 (0.041 g, 49.1%) as a white solid. $^1$H NMR (500 MHz, METHANOL-d$_4$) δ: 8.01-7.97 (m, 2H), 7.72-7.68 (m, 2H), 7.58-7.55 (m, 1H), 7.32-7.26 (m, 3H), 5.79 (s, 1H), 4.05 (ddd, J=12.1, 6.1, 4.7 Hz, 1H), 3.63-3.57 (m, 2H), 3.52-3.47 (m, 2H), 3.41-3.37 (m, 2H), 3.30-3.24 (m, 1H), 2.96-2.89 (m, 1H), 2.34-2.28 (m, 1H), 2.25-2.17 (m, 3H), 1.91-1.81 (m, 2H), 1.74-1.64 (m, 2H) ppm. MS (ESI) m/z: 490 (M+H)$^+$. Analytical HPLC: RT=5.94 min.

Example 12
4-(5-(4-methoxypiperidin-1-yl)-2-(7-azaspiro[3.5]nonane-2-carbonyl)-1,2,3,4-tetrahydroisoquinoline-1-carboxamido)benzoic acid, bis TFA Salt

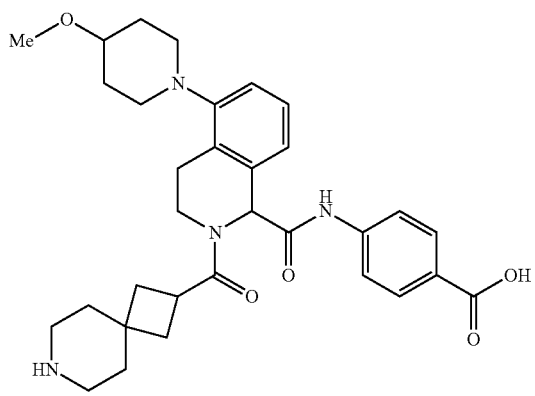 [SMILES: COC1CCN(c2cccc3c2CCN(C(=O)C2CC4(CCNCC4)C2)C3C(=O)Nc2ccc(C(=O)O)cc2)CC1]

Example 12 was made by an Ugi reaction as described in Example 9 substituting Intermediate 3 for Intermediate 2 followed by TFA deprotection and purification by reverse phase HPLC to afford approximately 20 mgs (5%) of a white solid. $^1$H NMR (400 MHz, MeOD) δ: 8.06-7.90 (m, 3H), 7.76-7.60 (m, 2H), 7.45-7.35 (m, 1H), 7.35-7.27 (m, 1H), 7.21 (d, J=7.8 Hz, 1H), 5.73 (s, 1H), 4.04 (d, J=12.1 Hz, 1H), 3.66-3.55 (m, 1H), 3.48 (br. s., 1H), 3.38 (br. s., 4H), 3.25-3.11 (m, 4H), 3.10-2.98 (m, 6H), 2.38-2.27 (m, 1H), 2.27-2.04 (m, 5H), 1.95 (d, J=4.3 Hz, 2H), 1.78 (d, J=4.3 Hz, 4H) ppm. MS (ESI) m/z: 561.3 (M+H)$^+$. Analytical HPLC: RT=4.30 min.

Example 13
4-(2-(7-carbamimidoyl-7-azaspiro[3.5]nonane-2-carbonyl)-5-(4-methoxypiperidin-1-yl)-1,2,3,4-tetrahydroisoquinoline-1-carboxamido)benzoic acid, bis-TFA Salt

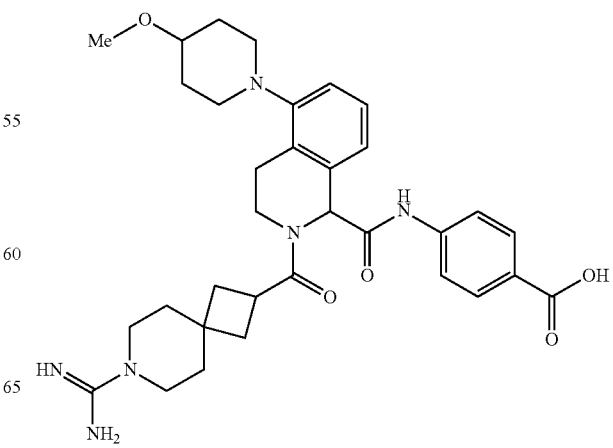

Example 13

Example 12 (15 mg, 0.019 mmol) was guanilated as described in Example 9, followed by reverse phase HPLC to afford a total of 9.8 mgs (54.5%) of Example 13 as a white solid. $^1$H NMR (400 MHz, METHANOL-d4) δ: 8.02-7.93 (m, 2H), 7.72-7.61 (m, 2H), 7.39-7.23 (m, 2H), 7.12 (d, J=7.8 Hz, 1H), 5.69 (s, 1H), 4.02 (dt, J=12.0, 4.6 Hz, 1H), 3.64-3.52 (m, 2H), 3.51-3.42 (m, 3H), 3.44-3.40 (m, 3H), 3.38 (dd, J=3.8, 1.8 Hz, 2H), 3.21 (dd, J=11.6, 4.5 Hz, 1H), 3.18-3.07 (m, 3H), 2.93 (t, J=9.2 Hz, 1H), 2.76 (t, J=9.2 Hz, 1H), 2.37-2.26 (m, 1H), 2.26-2.13 (m, 3H), 2.09 (d, J=13.1 Hz, 2H), 1.91-1.69 (m, 4H), 1.69-1.60 (m, 2H) ppm. MS (ESI) m/z: 603.3 (M+H)$^+$. Analytical HPLC: RT=5.04 min.

Example 14

(S)-4-(2-(7-carbamimidoyl-7-azaspiro[3.5]nonane-2-carbonyl)-5-(4-methoxypiperidin-1-yl)-1,2,3,4-tetrahydroisoquinoline-1-carboxamido)benzoic acid, Bis-HCl Salt

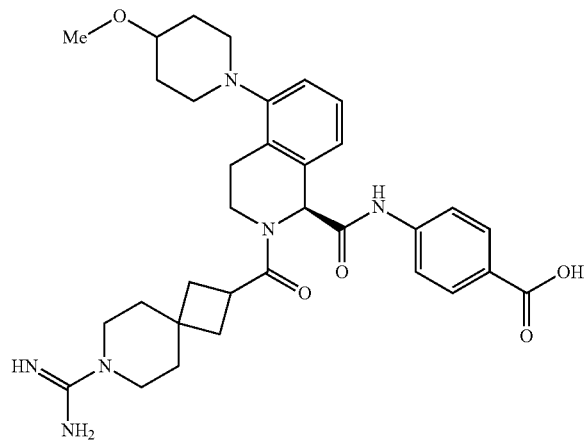 [SMILES: COC1CCN(c2cccc3c2CCN(C(=O)C2CC4(CCN(C(=N)N)CC4)C2)[C@@H]3C(=O)Nc2ccc(C(=O)O)cc2)CC1]

14A: tert-Butyl 4-(5-(4-methoxypiperidin-1-yl)-2-(2,2,2-trifluoroacetyl)-1,2,3,4-tetrahydroisoquinoline-1-carboxamido)benzoate was prepared by an Ugi reaction as described in Example 9 using trifluoroacetic acid instead of 7-(tert-butoxycarbonyl)-7-azaspiro[3.5]nonane-2-carboxylic acid to afford 704.3 mg (53.2%) of 14A. MS (ESI) m/z: 562.0 (M+H)+.

14B: tert-Butyl 4-(5-(4-methoxypiperidin-1-yl)-1,2,3,4-tetrahydroisoquinoline-1-carboxamido)benzoate: To a solution of 14A (697.7 mg, 1.242 mmol) in MeOH (6 mL) was added NaBH$_4$ (235 mg, 6.21 mmol). After 2 h, the reaction mixture was quenched into NaHCO$_3$ and extracted three times with ethyl acetate. The combined organics were washed with brine, dried (Na$_2$SO$_4$), filtered and purified by silica gel chromatography to afford 509.3 mg (88%) of 14B as a colorless solid. MS (ESI) m/z: 466.1 (M+H)$^+$.

14C and 14D: (R)-tert-Butyl 4-(5-(4-methoxypiperidin-1-yl)-1,2,3,4-tetrahydroisoquinoline-1-carboxamido)benzoate and (S)-tert-Butyl 4-(5-(4-methoxypiperidin-1-yl)-1,2,3,4-tetrahydroisoquinoline-1-carboxamido)benzoate: Racemic 14B was purified by preparative SFC chromatography (column: Chiralcel OD-H, 21×250 mm ID, 5 μm; flow rate: 45 mL/min, 100 bar BP, 40° C.; mobile phase: 20% Methanol/80% CO$_2$). The first eluting enantiomer, 14C (184.7 mg) was isolated as a colorless solid (≥99.0% ee). The second eluting enantiomer, 14D (186.0 mg) was isolated as a colorless solid (≥99.0% ee). $^1$H NMR of 14C: (400 MHz, METHANOL-d4) δ: 7.96-7.88 (m, 2H), 7.75-7.67 (m, 2H), 7.19-7.07 (m, 2H), 7.03-6.97 (m, 1H), 4.76 (s, 1H), 3.41 (s, 3H), 3.19-3.10 (m, 1H), 3.07-2.99 (m, 1H), 2.98-2.89 (m, 2H), 2.83 (br. s., 2H), 2.69-2.59 (m, 1H), 2.13-2.00 (m, 2H), 1.80-1.64 (m, 2H), 1.63-1.55 (s, 9H) ppm. $^1$H NMR of 14D: (400 MHz, METHANOL-d4) δ: 7.96-7.88 (m, 2H), 7.76-7.66 (m, 2H), 7.18-7.08 (m, 2H), 7.03-6.98 (m, 1H), 4.76 (s, 1H), 3.40 (s, 3H), 3.18-3.11 (m, 1H), 3.07-2.99 (m, 1H), 2.97-2.88 (m, 2H), 2.83 (br. s., 2H), 2.68-2.59 (m, 1H), 2.13-1.99 (m, 2H), 1.79-1.64 (m, 2H), 1.60 (s, 9H) ppm.

14E: (S)-tert-butyl 2-(1-((4-(tert-butoxycarbonyl)phenyl)carbamoyl)-5-(4-methoxypiperidin-1-yl)-1,2,3,4-tetrahydroisoquinoline-2-carbonyl)-7-azaspiro[3.5]nonane-7-carboxylate: To a solution of 7-(tert-butoxycarbonyl)-7-azaspiro[3.5]nonane-2-carboxylic acid (105 mg, 0.389 mmol) and 14D (181.3 mg, 0.389 mmol) in ethyl acetate, cooled to 0° C., was added pyridine (63.0 μl, 0.779 mmol) followed by dropwise addition of 1-propylphosphonic acid cyclic anhydride (50% wt solution in EtOAc) (348 μl, 0.584 mmol). The reaction was stirred for 30 min at 0° C., then allowed to warm to ambient temperature where it was stirred overnight. The reaction mixture was diluted with water and the phases separated. The aqueous later was extracted twice more with EtOAc and the combined organics washed with brine, dried (Na$_2$SO$_4$). Purification by silica gel chromatography afforded 257 mg (92%) of 14E as a faint yellow solid. $^1$H NMR (400 MHz, METHANOL-d$_4$) δ: 7.91-7.86 (m, 2H), 7.66-7.61 (m, 2H), 7.27-7.19 (m, 2H), 7.04 (dd, J=7.2, 1.9 Hz, 1H), 5.67 (s, 1H), 4.05-3.97 (m, 1H), 3.54 (s, 1H), 3.40 (s, 3H), 3.12 (s, 3H), 2.88-2.80 (m, 1H), 2.70-2.61 (m, 1H), 2.25-2.04 (m, 6H), 1.81-1.65 (m, 4H), 1.59 (s, 9H), 1.53-1.48 (m, 1H), 1.47-1.45 (m, 9H). MS (ESI) m/z: 717.1 (M+H)$^+$.

Example 14

Following procedures similar to Example 10, 14E was deprotected, coupled with (Z)-tert-butyl(((tert-butoxycarbonyl)amino)(1H-pyrazol-1-yl)methylene)carbamate and purified by preparative HPLC and preparative SFC chromatography (column: Chiralcel OD-H, 21×250 mm ID, 5 μm; flow rate: 45 mL/min, 100 bar BP, 40° C.; mobile phase: 30% Methanol/70% CO$_2$). The protected enantiomer was fully deprotected with TFA and purified by preparative HPLC (HCl buffer) to afford Example 14 (39.0 mg, 74.4% yield) as a solid. $^1$H NMR (METHANOL-d$_4$) δ: 10.51 (s, 1H), 7.96 (d, 2H), 7.69-7.75 (m, 1H), 7.63-7.68 (m, 2H), 7.49-7.56 (m, 1H), 5.85 (s, 1H), 4.09-4.17 (m, 1H), 3.48 (d, 11H), 3.44 (s, 3H), 3.36-3.40 (m, 2H), 2.20 (br. s., 6H), 1.80-1.86 (m, 1H), 1.65 (br. s., 1H) ppm. MS (ESI) m/z: 603.0 (M+H)$^+$. Analytical HPLC: RT=4.97 min.

Example 15

(R)-4-(2-(7-carbamimidoyl-7-azaspiro[3.5]nonane-2-carbonyl)-5-(4-methoxypiperidin-1-yl)-1,2,3,4-tetrahydroisoquinoline-1-carboxamido)benzoic acid, bis-HCl Salt

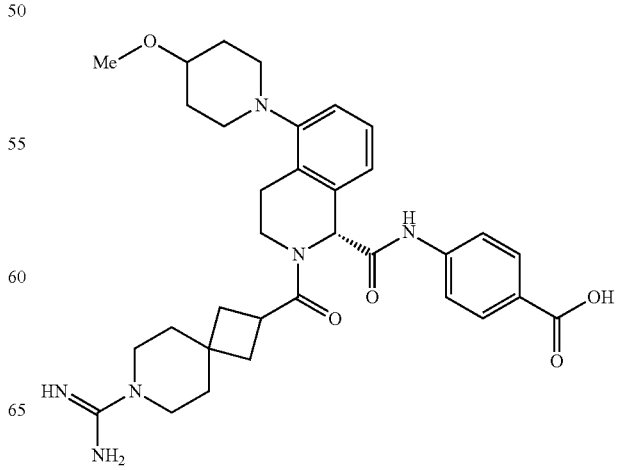

Example 15 was prepared as in Example 14 using Intermediate 14C to give after purification Example 15 (44.2 mg, 82% yield) as a solid. $^1$H NMR (METHANOL-d$_4$) δ: 10.49-10.52 (m, 1H), 7.94-7.99 (m, 2H), 7.57-7.71 (m, 3H), 7.51 (d, 1H), 5.83 (s, 1H), 4.12 (d, 1H), 3.45-3.81 (m, 11H), 3.44 (s, 3H), 3.38 (br. s., 2H), 3.17-3.27 (m, 1H), 2.07-2.36 (m, 6H), 1.81-1.86 (m, 1H), 1.62-1.68 (m, 1H) ppm. MS (ESI) m/z: 603.0 (M+H)$^+$. Analytical HPLC: RT=4.97 min.

Example 16

4-(2-(7-carbamimidoyl-7-azaspiro[3.5]nonane-2-carbonyl)-5-(4-methyl-2-oxopiperazin-1-yl)-1,2,3,4-tetrahydroisoquinoline-1-carboxamido)benzoic acid, bis-TFA Salt

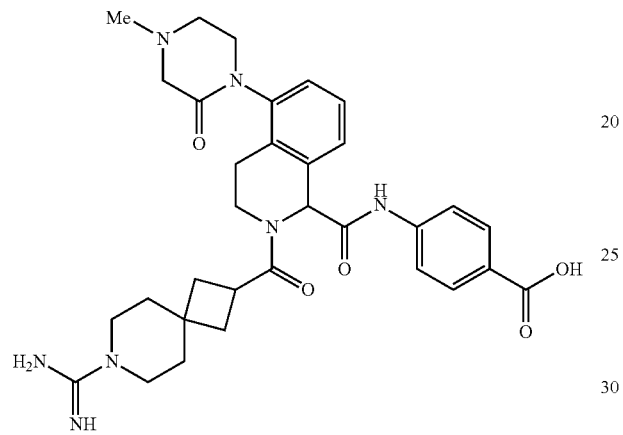

Example 16 was made in a similar manner as Example 9 substituting Intermediate 5 for Intermediate 2 to afford 27.5 mgs (19%) of Example 16 as a yellow solid. $^1$H NMR (400 MHz, METHANOL-d4) δ: 8.06-7.93 (m, 2H), 7.76-7.59 (m, 3H), 7.49-7.39 (m, 1H), 7.36-7.25 (m, 1H), 5.96-5.80 (m, 1H), 4.31-4.08 (m, 2H), 4.07-3.96 (m, 2H), 3.95-3.85 (m, 1H), 3.85-3.75 (m, 2H), 3.68-3.51 (m, 2H), 3.50-3.43 (m, 2H), 3.37 (d, J=5.3 Hz, 2H), 3.16-3.09 (m, 3H), 3.09-3.00 (m, 1H), 2.90-2.74 (m, 1H), 2.39-2.06 (m, 4H), 1.93-1.75 (m, 2H), 1.64 (d, J=3.8 Hz, 2H) ppm. MS (ESI) m/z: 602.3 (M+H)$^+$. Analytical HPLC: RT=3.36 min.

Example 17

(R)-4-(2-(7-carbamimidoyl-7-azaspiro[3.5]nonane-2-carbonyl)-5-(4-methyl-2-oxopiperazin-1-yl)-1,2,3,4-tetrahydroisoquinoline-1-carboxamido)benzoic acid, bis HCl Salt

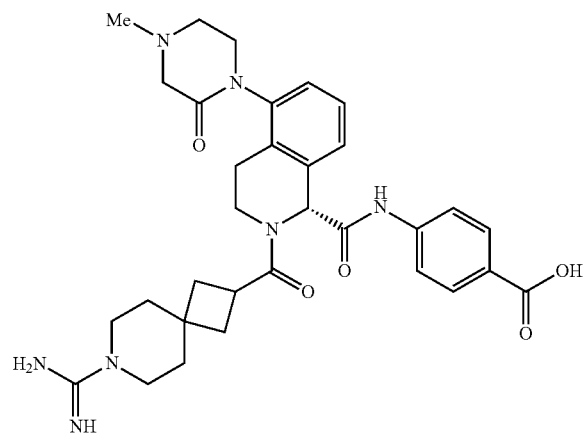 [SMILES: CN1CCN(c2cccc3c2CCN(C(=O)C2CC4(CCN(C(=N)N)CC4)C2)[C@H]3C(=O)Nc2ccc(C(=O)O)cc2)C(=O)C1]

Example 17 was prepared from a similar method as was used for Example 10 using Intermediate 5 instead of Intermediate 2 and was isolated as the first eluting peak after chiral SFC HPLC separation using Chiralcel OD-H, 30×250 mm ID, 5 nm, using 75/25 CO$_2$/MeOH at 85 mL/min, 150 bar BP, 40° C. followed by deprotection with TFA/DCM and HPLC purification (HCl buffer) to afford 38 mgs (70%) of Example 17 as a white solid. $^1$H NMR (400 MHz, METHANOL-d4) δ: 8.03-7.91 (m, 2H), 7.76-7.60 (m, 3H), 7.44 (t, J=8.0 Hz, 1H), 7.31 (d, J=7.6 Hz, 1H), 7.14 (br. s., 1H), 5.91-5.79 (m, 1H), 4.13 (d, J=6.3 Hz, 2H), 4.02 (br. s., 2H), 3.88 (br. s., 1H), 3.77 (br. s., 2H), 3.66-3.51 (m, 2H), 3.51-3.42 (m, 2H), 3.19-3.00 (m, 5H), 2.80 (d, J=14.4 Hz, 1H), 2.35-2.11 (m, 4H), 1.82 (br. s., 2H), 1.65 (br. s., 2H) ppm. MS (ESI) m/z: 602.1 (M+H)$^+$. Analytical HPLC: RT=2.35 min.

Example 18

(S)-4-(2-(7-carbamimidoyl-7-azaspiro[3.5]nonane-2-carbonyl)-5-(4-methyl-2-oxopiperazin-1-yl)-1,2,3,4-tetrahydroisoquinoline-1-carboxamido)benzoic acid, bis HCl Salt

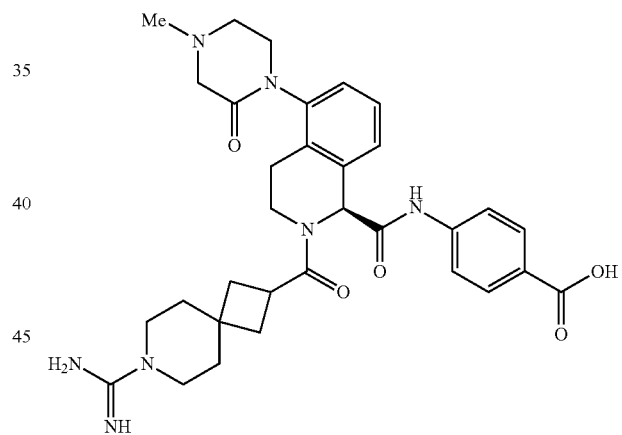

Example 18 was isolated as the second eluting peak from Example 17, after chiral SFC HPLC separation using Chiralcel OD-H, 30×250 mm ID, 5 nm, using 75/25 CO$_2$/MeOH at 85 mL/min, 150 bar BP, 40° C. followed by deprotection with TFA/DCM and HPLC purification (HCl buffer) to afford 40 mgs (74%) of a Example 18 as a white solid. $^1$H NMR (400 MHz, METHANOL-d4) δ: 8.09-7.93 (m, 2H), 7.79-7.60 (m, 3H), 7.44 (t, J=7.8 Hz, 1H), 7.31 (d, J=7.3 Hz, 1H), 7.14 (br. s., 1H), 5.91-5.82 (m, 1H), 4.19 (br. s., 2H), 4.01 (br. s., 2H), 3.82 (br. s., 3H), 3.68-3.53 (m, 2H), 3.35-3.25 (m, 3H) 3.22-3.01 (m, 4H), 2.83 (d, J=4.5 Hz, 1H), 2.35-2.10 (m, 4H), 1.82 (br. s., 2H), 1.65 (br. s., 2H) ppm. MS (ESI) m/z: 602.1 (M+H)$^+$. Analytical HPLC: RT=2.5 min.

Example 19

(R)-4-(2-(2-(1-carbamimidoylpiperidin-4-yl)acetyl)-5-(4-methyl-2-oxopiperazin-1-yl)-1,2,3,4-tetrahydroisoquinoline-1-carboxamido)benzoic acid, bis-HCl Salt

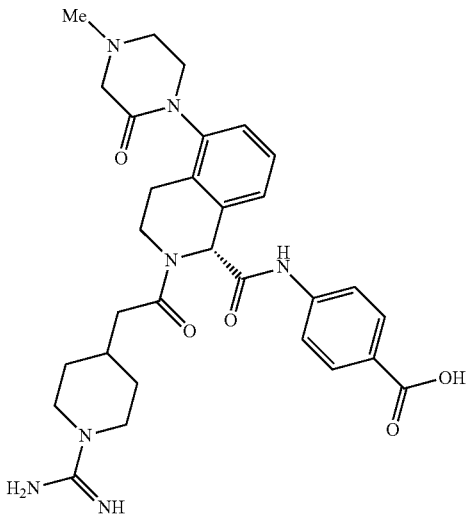 [SMILES: CN1CCN(c2cccc3c2CCN(C(=O)CC2CCN(C(=N)N)CC2)[C@H]3C(=O)Nc2ccc(C(=O)O)cc2)C(=O)C1]

Example 19 was prepared in a similar manner as Example 17 substituting 2-(1-(tert-butoxycarbonyl)piperidin-4-yl)acetic acid for 7-(tert-butoxycarbonyl)-7-azaspiro[3.5]nonane-2-carboxylic acid and isolated as the first eluting peak after chiral SFC HPLC separation using Chiralcel OD-H, 20×250 mm ID, 5 nm, using 75/25 CO$_2$/MeOH at 85 mL/min, 150 bar BP, 40° C. followed by deprotection with TFA/DCM, HPLC purification and conversion to the HCl salt by treatment with dilute HCl, followed by freeze-drying, to afford 8 mgs (2.3%) of a white solid. $^1$H NMR (400 MHz, METHANOL-d4) δ: 8.05-7.91 (m, 2H), 7.76-7.59 (m, 3H), 7.46-7.38 (m, 1H), 7.38-7.29 (m, 1H), 6.00-5.79 (m, 1H), 4.33-4.10 (m, 4H), 3.88 (d, J=12.4 Hz, 5H), 3.72 (d, J=12.4 Hz, 1H), 3.24-3.00 (m, 6H), 2.96-2.81 (m, 1H), 2.74-2.61 (m, 1H), 2.47 (dt, J=15.2, 7.6 Hz, 1H), 2.19 (br. s., 1H), 1.90 (d, J=11.9 Hz, 2H), 1.53-1.22 (m, 3H) ppm. MS (ESI) m/z: 576.2 (M+H)$^+$. Analytical HPLC: RT=3.22 min (solvent B started at 5%).

Example 20

(S)-4-(2-(2-(1-carbamimidoylpiperidin-4-yl)acetyl)-5-(4-methyl-2-oxopiperazin-1-yl)-1,2,3,4-tetrahydroisoquinoline-1-carboxamido)benzoic acid, bis-HCl Salt

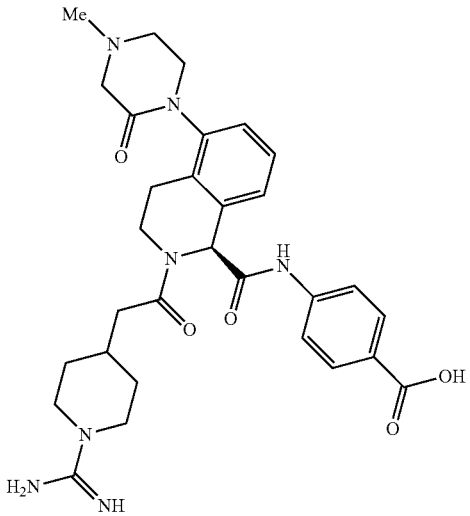 [SMILES: CN1CCN(c2cccc3c2CCN(C(=O)CC2CCN(C(=N)N)CC2)[C@@H]3C(=O)Nc2ccc(C(=O)O)cc2)C(=O)C1]

Example 20 was prepared as described in Example 19 and was isolated as the second eluting peak after chiral SFC HPLC separation using Chiralcel OD-H, 20×250 mm ID, 5 nm, using 75/25 CO$_2$/MeOH at 85 mL/min, 150 bar BP, 40° C. followed by deprotection with TFA/DCM, HPLC purification and conversion to HCl salt to afford 4.7 mgs (1.3%) of a white solid. $^1$H NMR (400 MHz, METHANOL-d4) δ 8.1-7.9 (m, 2H), 7.8-7.6 (m, 3H), 7.5-7.4 (m, 1H), 7.4-7.3 (m, 1H), 6-5.8 (m, 1H), 4.3-4.1 (m, 3H), 4.1-3.8 (m, 6H), 3.8-3.6 (m, 1H), 3.26-3.0 (m, 5H), 3 (d, J=15.2 Hz, 1H), 2.95-2.8 (m, 1H), 2.7-2.6 (m, 1H), 1.6-2.4 (m, 1H), 2.2 (br. s., 1H), 1.9 (t, J=13.5 Hz, 2H), 1.5-1.3 (m, 3H) ppm. MS (ESI) m/z: 576.2 (M+H)$^+$. Analytical HPLC: RT=3.25 min (where solvent B was started at 5%).

Example 21

4-(2-(1-carbamimidoylpiperidine-3-carbonyl)-5-(4-methoxypiperidin-1-yl)-1,2,3,4-tetrahydroisoquinoline-1-carboxamido)benzoic acid, bis-TFA Salt

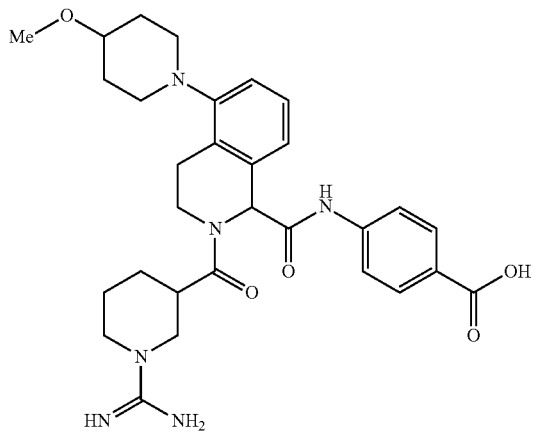 [SMILES: COC1CCN(c2cccc3c2CCN(C(=O)C2CCCN(C(=N)N)C2)C3C(=O)Nc2ccc(C(=O)O)cc2)CC1]

Example 21 was prepared using an Ugi reaction as described in Example 9, substituting 1-(((9H-fluoren-9-yl)methoxy)carbonyl)piperidine-3-carboxylic acid for 7-(tert-butoxycarbonyl)-7-azaspiro[3.5]nonane-2-carboxylic acid, followed by removal of the FMOC group as described in Example 6 and guanilation as in Example 10 which afforded two diastereomers. Diastereomer one was deprotected with TFA and purified by preparative HPLC to give 2.51 mg (82%) of Example 21 as a solid. $^1$H NMR (400 MHz, METHANOL-d$_4$) δ: 10.37 (s, 1H), 7.98-7.93 (m, 2H), 7.64 (dd, J=8.8, 1.5 Hz, 2H), 7.32-7.24 (m, 2H), 7.12 (d, J=8.1 Hz, 1H), 5.72 (s, 1H), 4.20-4.14 (m, 1H), 3.86-3.78 (m, 2H), 3.58-3.49 (m, 1H), 3.41 (s, 3H), 3.47-3.39 (m, 6H), 3.29-3.05 (m, 6H), 2.95 (d, J=10.1 Hz, 1H), 2.75 (br. s., 1H), 2.23 (br. s., 1H), 2.11 (br. s., 2H), 1.90 (br. s., 1H), 1.84-1.69 (m, 4H) ppm. MS (ESI) m/z: 563.0 (M+H)$^+$. Analytical HPLC: RT=4.95 min.

Example 22

4-(2-(1-carbamimidoylpiperidine-3-carbonyl)-5-(4-methoxypiperidin-1-yl)-1,2,3,4-tetrahydroisoquinoline-1-carboxamido)benzoic acid, bis-TFA Salt

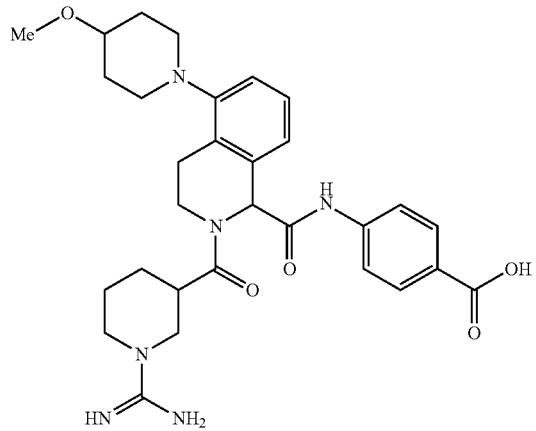 [SMILES: COC1CCN(c2cccc3c2CCN(C(=O)C2CCCN(C(=N)N)C2)C3C(=O)Nc2ccc(C(=O)O)cc2)CC1]

Example 22 was prepared from the second diastereomer intermediate described in Example 21 to give after deprotection with TFA and HPLC purification, 3.29 mg, (72.3%) of Example 22 as a solid. $^1$H NMR (400 MHz, METHANOL-$d_4$) δ: 10.46 (s, 1H), 7.99-7.94 (m, 2H), 7.65 (dd, J=8.8, 1.5 Hz, 2H), 7.34-7.24 (m, 2H), 7.13 (d, J=6.8 Hz, 1H), 5.68 (s, 1H), 4.30-4.22 (m, 1H), 3.93-3.78 (m, 2H), 3.41 (s, 3H), 3.55-3.37 (m, 6H), 3.27-3.11 (m, 6H), 2.95 (d, J=9.3 Hz, 1H), 2.77 (br. s., 1H), 2.18-2.05 (m, 3H), 1.91-1.68 (m, 5H). MS (ESI) m/z: 563.0 (M+H)$^+$. Analytical HPLC: RT=5.14 min.

Example 23

4-(2-(2-(1-carbamimidoylpiperidin-4-yl)acetyl)-5-(4-methoxypiperidin-1-yl)-1,2,3,4-tetrahydroisoquinoline-1-carboxamido)benzoic acid, bis-TFA salt

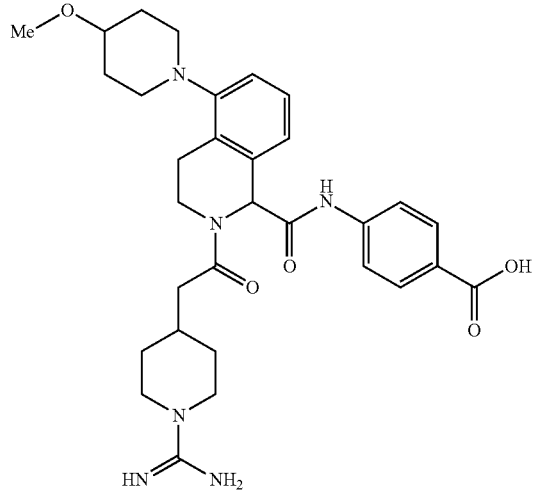 [SMILES: COC1CCN(c2cccc3c2CCN(C(=O)CC2CCN(C(=N)N)CC2)C3C(=O)Nc2ccc(C(=O)O)cc2)CC1]

Example 23 was prepared using an Ugi reaction as described in Example 9, substituting 2-(1-(tert-butoxycarbonyl)piperidin-4-yl)acetic acid for 7-(tert-butoxycarbonyl)-7-azaspiro[3.5]nonane-2-carboxylic acid, followed by guanilation as in Example 10. Purification by preparative HPLC afforded 2.61 mg (61.7%) of Example 23 as a solid. $^1$H NMR (400 MHz, METHANOL-$d_4$) δ: 10.40 (br. s., 1H), 7.98 (d, J=1.5 Hz, 2H), 7.68-7.61 (m, 2H), 7.32-7.22 (m, 2H), 7.10 (d, J=7.3 Hz, 1H), 5.72 (s, 1H), 4.22-4.13 (m, 1H), 3.89 (d, J=12.9 Hz, 2H), 3.51-3.43 (m, 2H), 3.42 (d, J=2.3 Hz, 3H), 3.25-3.07 (m, 6H), 2.91 (t, J=10.7 Hz, 1H), 2.77-2.64 (m, 2H), 2.44 (dd, J=15.7, 7.6 Hz, 1H), 2.26-2.03 (m, 3H), 2.03-1.86 (m, 2H), 1.76 (d, J=11.4 Hz, 2H), 1.45-1.29 (m, 2H). MS (ESI) m/z: 577.0 (M+H)$^+$. Analytical HPLC: RT=4.75 min.

Example 24

4-(2-(1-carbamimidoylpiperidine-4-carbonyl)-5-(4-methoxypiperidin-1-yl)-1,2,3,4-tetrahydroisoquinoline-1-carboxamido)benzoic acid, bis-TFA salt

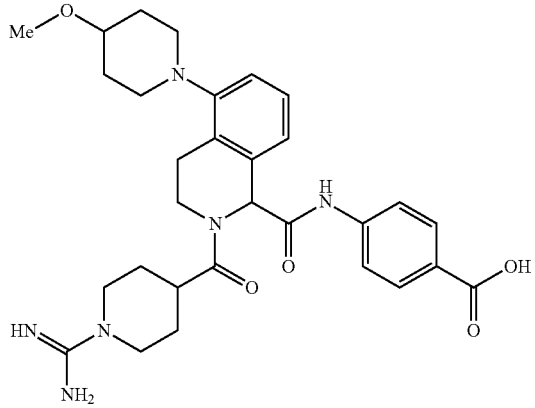 [SMILES: COC1CCN(c2cccc3c2CCN(C(=O)C2CCN(C(=N)N)CC2)C3C(=O)Nc2ccc(C(=O)O)cc2)CC1]

Example 24 was prepared using an Ugi reaction as described in Example 9, substituting 1-(tert-butoxycarbonyl)piperidine-4-carboxylic acid for 7-(tert-butoxycarbonyl)-7-azaspiro[3.5]nonane-2-carboxylic acid, followed by deprotection and guanilation as described in Example 10. Final deprotection and purification by preparative HPLC afforded 1.27 mg (7.63%) of Example 24 as a solid. $^1$H NMR (METHANOL-$d_4$) δ: 10.41 (s, 1H), 7.93-7.98 (m, 2H), 7.63-7.67 (m, 2H), 7.22-7.31 (m, 2H), 7.09 (m, 1H), 5.69 (s, 1H), 4.26 (m, 1H), 3.94 (d, 2H), 3.49-3.61 (m, 1H), 3.39-3.43 (m, 3H), 3.16-3.29 (m, 5H), 3.12 (m, 1H), 2.86-2.94 (m, 1H), 2.72 (m, 1H), 1.98-2.17 (m, 3H), 1.86-1.96 (m, 1H), 1.68-1.85 (m, 4H) ppm. MS (ESI) m/z: 563.1 (M+H)$^+$. Analytical HPLC: RT=4.90 min.

Example 25

4-(2-(1-carbamimidoylpiperidine-4-carbonyl)-5-(4-methyl-2-oxopiperazin-1-yl)-1,2,3,4-tetrahydroisoquinoline-1-carboxamido)benzoic acid, bis-TFA Salt

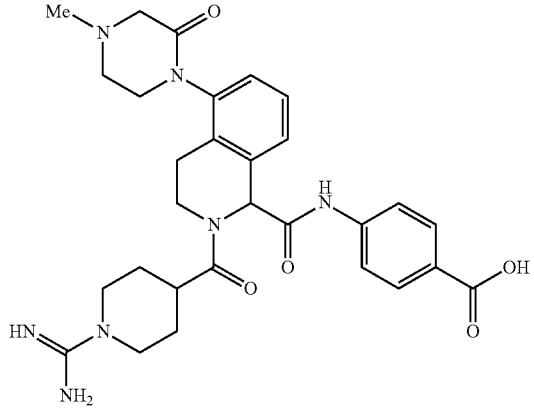 [SMILES: CN1CCN(c2cccc3c2CCN(C(=O)C2CCN(C(=N)N)CC2)C3C(=O)Nc2ccc(C(=O)O)cc2)C(=O)C1]

Example 25 was prepared in a similar manner as Examples 16 and 24 to afford 5 mg (15%) of Example 25 as a colorless solid. $^1$H NMR (400 MHz, METHANOL-D3) δ: 8.08-7.87 (m, 1H), 7.97-7.82 (m, 2H), 7.67-7.60 (m, 2H), 7.45-7.41 (t, 1H), 7.31-7.22 (m, 1H), 5.88 (s, 1H), 5.81 (s, 1H), 4.30-3.75 (cp, 10H), 3.25 (m, 2H), 3.06 (s, 3H), 2.87 (m, 2H), 2.00-1.45 (m, 4H). MS (ESI) m/z: 562.3 (M+H)$^+$. Analytical HPLC: RT=2.92 min.

Example 26

4-(2-(1-aminoisoquinoline-6-carbonyl)-5-bromo-1,2,3,4-tetrahydroisoquinoline-1-carboxamido)benzoic acid

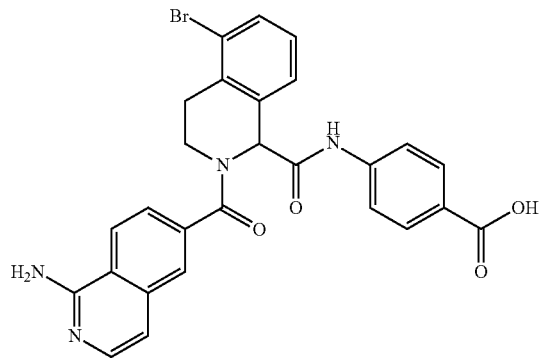 [SMILES: Nc1nccc2cc(C(=O)N3CCc4c(Br)cccc4C3C(=O)Nc3ccc(C(=O)O)cc3)ccc12]

26A. 1-((tert-butoxycarbonyl)amino)isoquinoline-6-carboxylic acid: Lithium hydroxide monohydrate (0.229 g, 5.46 mmol) was added to a solution of methyl 1-((tert-butoxycarbonyl)amino)isoquinoline-6-carboxylate (0.33 g, 1.09 mmol) in THF/MeOH/Water (1:1:1; 15 ml). The mixture stirred at room temperature overnight. The organics were evaporated and the remaining aqueous layer made acidic with 1.0M HCl solution, extracted with EtOAc (3×), washed with water followed by brine, dried over sodium sulfate, filtered, and concentrated. 26A was carried forward to the next step.

26B. tert-butyl 5-bromo-1-((4-(tert-butoxycarbonyl)phenyl)carbamoyl)-3,4-dihydroisoquinoline-2(1H)-carboxylate: Phosphorus oxychloride (1.894 g, 12.35 mmol) was added to Intermediate 4 (4.0 g, 11.23 mmol) and tert-butyl 4-aminobenzoate (2.170 g, 11.23 mmol) in pyridine (44.9 ml) at 0° C. After 2 h, the reaction was quenched with saturated NH$_4$Cl (50 mL) and extracted with EtOAc (3×100 mL). The combined organic layer was washed several times with 1.0N HCl solution, water, brine, dried over sodium sulfate, filtered, and concentrated to give 26B as a tan solid. MS (ESI) m/z: 531/533 (Br isotope) (M+H)$^+$.

26C. tert-butyl 4-(5-bromo-1,2,3,4-tetrahydroisoquinoline-1-carboxamido)benzoate, HCl: To 26B (1.0 g, 1.882 mmol) dissolved in THF (10 mL) was added HCl (4.0M in dioxane) (3.29 ml, 13.17 mmol). After 24 h, 26C (0.514 g, 1.099 mmol, 58.4% yield) was collected by filtration.

MS (ESI) m/z: 432/433 (Br isotope) (M+H)$^+$.

Example 26

4-(2-(1-Aminoisoquinoline-6-carbonyl)-5-bromo-1,2,3,4-tetrahydroisoquinoline-1-carboxamido)benzoic acid: 1-Propanephosphonic acid cyclic anhydride (0.083 ml, 0.139 mmol) was added to a solution of 26C (0.05 g, 0.116 mmol), 26A (0.033 g, 0.116 mmol), DIPEA (0.061 ml, 0.348 mmol) in DMF (3 mL). After 2 h, the reaction mixture was partitioned between water and EtOAc. The organic layer was washed with 1.0M HCl solution, water, brine, dried over sodium sulfate, filtered, and concentrated. The residue was treated with 50% TFA/DCM for 1 h, concentrated, and purified by reverse phase preparative HPLC. $^1$H NMR: (500 MHz, METHANOL-d$_4$) δ: 8.57 (d, J=8.5 Hz, 1H), 8.11 (s, 1H), 8.02 (d, J=8.5 Hz, 2H), 7.92-7.88 (m, 1H), 7.75 (d, J=8.5 Hz, 2H), 7.68-7.60 (m, 3H), 7.33 (d, J=6.9 Hz, 1H), 7.27 (t, J=7.8 Hz, 1H), 6.06 (s, 1H), 4.07 (ddd, J=12.7, 7.8, 4.3 Hz, 1H), 3.80-3.73 (m, 1H), 3.25-3.19 (m, 1H), 3.15-3.06 (m, 1H) ppm. MS (ESI) m/z: 543/545 (Br isotope) (M+H)$^+$. Analytical HPLC: RT=6.46 min.

Numerous modifications and variations of the present invention are possible in light of the above teachings. It is therefore to be understood that within the scope of the appended claims, the invention may be practiced otherwise than as specifically described herein.

What is claimed is:
1. A compound according to formula (I):

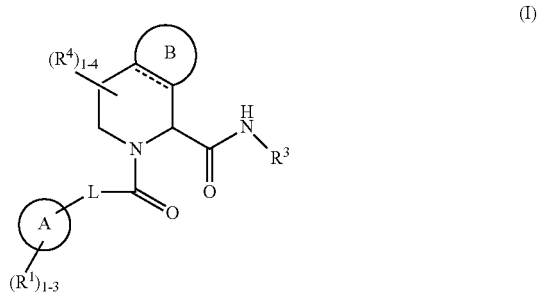

or a stereoisomer, tautomer, pharmaceutically acceptable salt thereof, wherein:
ring A is heterocycle comprising carbon atoms and NR$^2$;
L is selected from a bond, —CHR$^7$—, —CHR$^7$CHR$^7$—, —CR$^7$=CR$^7$—, and —C≡C—;
ring B is phenyl or 5- to 6-membered heterocycle containing carbon atoms and 1-3 heteroatoms selected from the group consisting of N, NR$^6$, O, and S(O)$_p$, wherein said phenyl or heterocycle is substituted with 0-3 R$^5$;
---- is an optional bond;
R$^1$, at each occurrence, is H
R$^2$ is selected from —C(=NH)NH$_2$ and C(=NOR$^6$)NH$_2$;
R$^3$ is selected from C$_{1-6}$ alkyl substituted with 1-3 R$^{3a}$, C$_{3-10}$ carbocycle substituted with 1-3 R$^{3a}$, and 5-10 membered heterocycle comprising carbon atoms and 1-4 heteroatoms selected from N, NR$^a$, O, and S(O)$_p$; wherein said heterocycle is substituted with 1-3 R$^{3a}$;
R$^{3a}$, at each occurrence, is selected from H, halogen, C$_{1-4}$ alkyl, —OH, C$_{1-4}$ alkoxy, —CN, —NH$_2$, —NH(C$_{1-4}$ alkyl), —CO$_2$H, —CH$_2$CO$_2$H, —CO$_2$(C$_{1-4}$ alkyl), —CO$_2$—C$_{1-4}$ alkylene-O(C alkyl), —CO$_2$—C$_{1-4}$ alkylene-N(C$_{1-4}$ alkyl)$_2$, —CONH$_2$, —CONH(C$_{1-6}$ alkyl), —CON(C$_{1-4}$ alkyl)$_2$, —CONHCO$_2$C$_{1-4}$ alkyl, —NHCOC$_{1-4}$ alkyl, —NHCO$_2$(C$_{1-4}$ alkyl), SO$_2$R$^6$, SO$_2$NR$^6$R$^6$, SO$_2$NHC(O)R$^6$, NHSO$_2$NR$^6$, NHSO$_2$R$^6$, R$^c$, —CONHR$^c$, and —CO$_2$R$^c$;
R$^4$, at each occurrence, is selected from H, F, and C$_{1-4}$ alkyl;
R$^5$ is selected from H, halogen, C$_{1-4}$ alkyl, C$_{1-4}$alkoxy, C$_{1-4}$haloalkoxy, OH, CN, NH$_2$, —N(C$_{1-4}$ alkyl)$_2$, $NO_2$, —$OCO(C_{1-4}$ alkyl), —O—$C_{1-4}$ alkylene-O($C_{1-4}$ alkyl), —O—$C_{1-4}$ alkylene-N($C_{1-4}$ alkyl)$_2$, —$CO_2H$, —$CO_2(C_{1-4}$ alkyl), —$(CH_2)_nCONH_2$, $SO_2R^6$, $SO_2NR^6R^6$, $SO_2NHC(O)R^6$, $NHSO_2NR^6$, $NHSO_2R^6$, —$(CH_2)_n$—$C_{3-10}$ carbocycle and —$(CH_2)_n$-5- to 12-membered heterocycle comprising carbon atoms and 1-4 heteroatoms selected from N, $NR^a$, O, and $S(O)_p$; wherein said carbocycle or heterocycle is substituted with 1-3 $R^b$;

$R^6$, at each occurrence, is selected from H and $C_{1-4}$ alkyl;

$R^7$, at each occurrence, is selected from H, halo, OH, and $C_{1-4}$ alkyl;

$R^a$, at each occurrence, is selected from H, $C_{1-4}$ alkyl, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$;

$R^b$, at each occurrence, is selected from H, CN, =O, OH, halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —$NHCO_2(C_{1-4}$ alkyl), $SO_2R^6$, $SO_2NR^6R^6$, $SO_2NHC(O)R^6$, $NHSO_2NR^6$, $NHSO_2R^6$, —$R^c$, $COR^c$, $CO_2R^c$, and $CONHR^c$; optionally, $R^b$ and $R^b$ together with the carbon atom to which they are both attached form a 5-6 membered heterocyclic ring;

$R^c$, at each occurrence, is selected from —$(CH_2)_n$—$C_{3-6}$ cycloalkyl, —$(CH_2)_n$-phenyl, and —$(CH_2)_n$-5- to 6-membered heterocycle comprising carbon atoms and 1-4 heteroatoms selected from N, NH, N($C_{1-4}$ alkyl), O, and $S(O)_p$; wherein each ring moiety is substituted with 0-2 $R^d$;

$R^d$, at each occurrence, is selected from =O, F, —OH, $C_{1-4}$ alkyl, $NH_2$, $NH(C_{1-4}$ alkyl), $N(C_{1-4}$ alkyl)$_2$, $C_{1-4}$ alkoxy, and —$NHCO(C_{1-4}$ alkyl), and heterocycle comprising carbon atoms and 1-4 heteroatoms selected from N, NH, N($C_{1-4}$ alkyl), O, and $S(O)_p$;

n, at each occurrence, is selected from 0, 1, 2, 3, and 4; and p, at each occurrence, is selected from 0, 1, and 2.

2. The compound of claim 1 having formula (II):

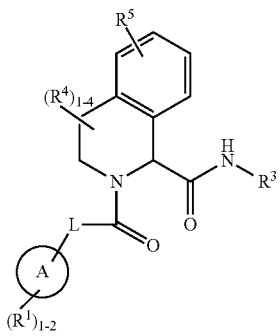

(II)

or a stereoisomer, tautomer, pharmaceutically acceptable salt thereof, wherein:

ring A is 4- to 12-membered monocyclic, bicyclic heterocycle comprising carbon atoms and $NR^2$, wherein said heterocycle may be a spiro;

L is selected from a bond, —$CHR^7$—, and —$CHR^7CHR^7$—;

$R^1$, at each occurrence, is H;

$R^2$ is selected from —C(=NH)$NH_2$ and C(=$NOR^6$)$NH_2$;

$R^3$ is selected from $C_{3-10}$ carbocycle substituted with 1-3 $R^{3a}$, and 5-10 membered heterocycle comprising carbon atoms and 1-4 heteroatoms selected from N, $NR^a$, O, and $S(O)_p$;

wherein said heterocycle is substituted with 1-3 $R^{3a}$;

$R^{3a}$, at each occurrence, is selected from H, halogen, $C_{1-4}$ alkyl, —OH, $C_{1-4}$ alkoxy, —CN, —$NH_2$, —NH($C_{1-4}$ alkyl), —$CO_2H$, $CO_2(C_{1-4}$ alkyl), and —$NHCO_2(C_{1-4}$ alkyl);

$R^4$, at each occurrence, is selected from H, F, and $C_{1-4}$ alkyl;

$R^5$ is selected from H, halogen, $C_{1-4}$alkoxy, $C_{1-4}$haloalkoxy, —$(CH_2)_n$—$C_{3-10}$ carbocycle and —$(CH_2)_n$-5- to 10-membered heterocycle comprising carbon atoms and 1-4 heteroatoms selected from N, $NR^a$, O, and $S(O)_p$; wherein said carbocycle or heterocycle is substituted with 1-3 $R^b$;

$R^6$, at each occurrence, is selected from H and $C_{1-4}$ alkyl;

$R^7$, at each occurrence, is selected from H and $C_{1-4}$ alkyl;

$R^a$ is selected from H, $C_{1-4}$ alkyl, $CO(C_{1-4}$ alkyl), $COCF_3$, $CO_2(C_{1-4}$ alkyl), and —$CONH_2$;

$R^b$ is selected from H, =O, OH, halogen, CN, $C_{1-4}$ alkyl, $C_{1-4}$ alkoxy, $OCF_3$, $NH_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), and —$CON(C_{1-4}$ alkyl)$_2$, $SO_2(C_{1-4}$ alkyl), $SO_2NH(C_{1-4}$ alkyl), $NHSO_2NR^6$, $NHSO_2(C_{1-4}$ alkyl), and $R_c$; optionally, $R^b$ and $R^b$ together with the carbon atom to which they are both attached form a 4-6 membered heterocyclic ring.

3. The compound of claim 2 or a stereoisomer, tautomer, pharmaceutically acceptable salt thereof, wherein:

$R^5$ is selected from H, halogen, phenyl, and —$(CH_2)_n$-5- to 10-membered heterocycle or heteroaryl comprising carbon atoms and 1-4 heteroatoms selected from N, $NR^a$, O, and $S(O)_p$; wherein said phenyl or heterocycle is substituted with 1-3 $R^b$.

4. The compound of claim 3 or a stereoisomer, tautomer, pharmaceutically acceptable salt thereof, wherein:

$R^5$ is selected from H, F,

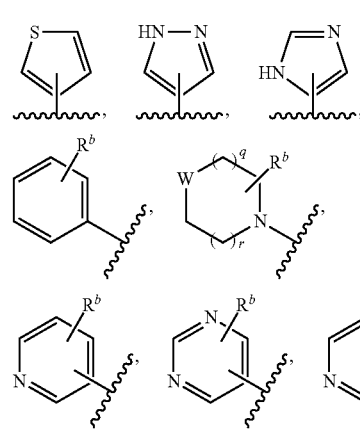

-continued

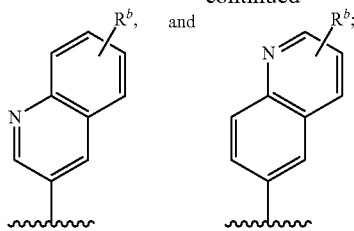

W is selected from $CR^bR^b$, O, $S(O)_p$, and $NR^a$;

$R^a$ is selected from H, $C_{1-4}$ alkyl, $CO(C_{1-4}$ alkyl), and $COCF_3$;

$R^b$ is selected from H, =O, OH, halogen, $C_{1-4}$ alkyl, $C_{1-4}$ alkoxy, $OCF_3$, $NH_2$, $N(C_{1-4}$ alkyl$)_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl$)_2$, phenyl, pyridyl; optionally, $R^b$ and $R^b$ together with the carbon atom to which they are both attached form a 4-6 membered heterocyclic ring;

q, at each occurrence, is selected from 0, 1, and 2; and r, at each occurrence, is selected from 0, 1, and 2.

5. The compound of claim 4 or a stereoisomer, tautomer, pharmaceutically acceptable salt thereof, wherein:
$R^5$ is

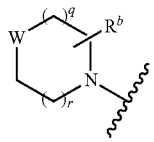

selected from

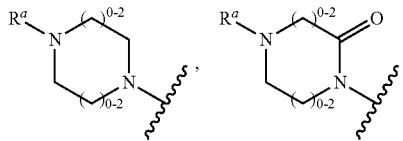

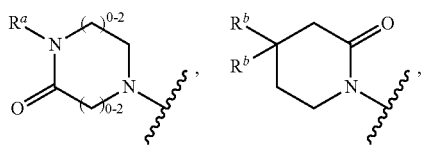

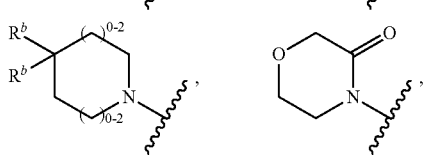

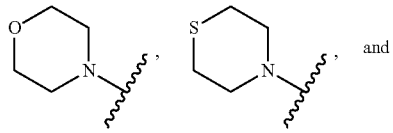

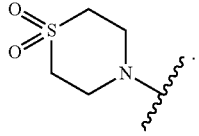

6. The compound of claim 5 or a stereoisomer, tautomer, pharmaceutically acceptable salt thereof, wherein:

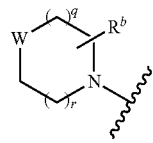

is selected from

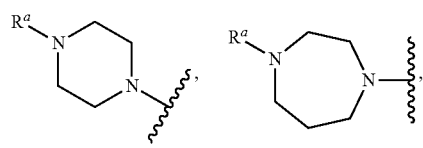

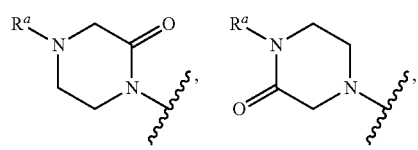

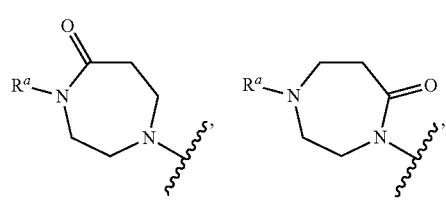

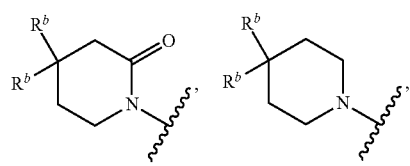

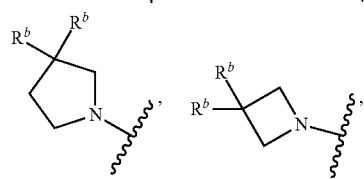

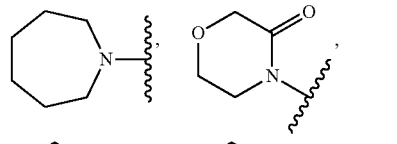

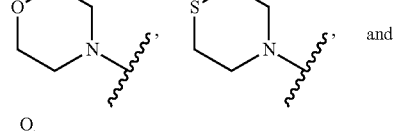

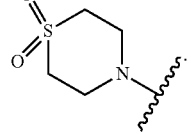

7. The compound of claim 2 or a stereoisomer, tautomer, pharmaceutically acceptable salt thereof, wherein:

ring A is selected from

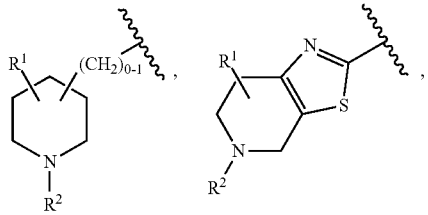

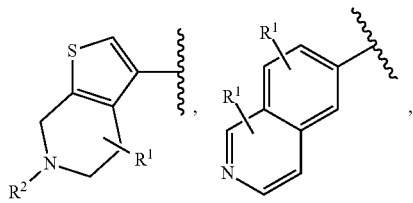

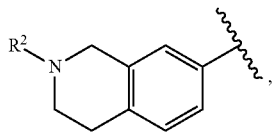, and

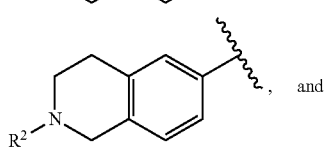

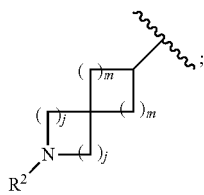;

R[1], at each occurrence, is H;

R[2] is selected from —C(=NH)NH$_2$ and C(=NOR[6])NH$_2$;

R[3] is selected from phenyl substituted with 1-2 R[3a], C$_{3-6}$ cycloalkyl substituted with 1-2 R[3a], heterocycle substituted with 1-2 R[3a]; wherein said heterocycle is selected from piperidinyl, pyridyl, indolyl, and indazolyl;

R[6], at each occurrence, is selected from H and C$_{1-4}$ alkyl;

m, at each occurrence, is selected from 1 and 2; and j, at each occurrence, is selected from 1 and 2.

8. The compound of claim 7 or a stereoisomer, tautomer, pharmaceutically acceptable salt thereof, wherein:

ring A is selected from

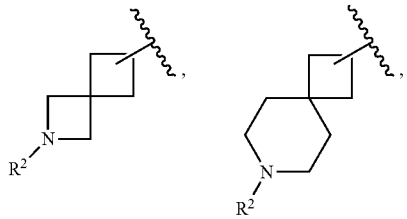

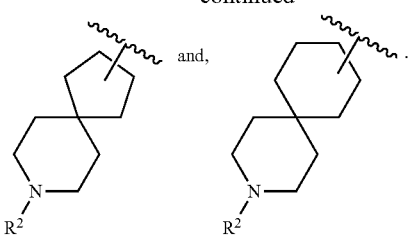 and,

9. The compound of claim 2 having formula (III):

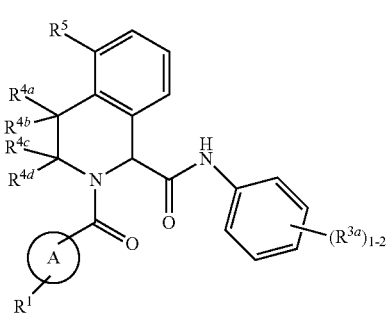

(III)

or a stereoisomer, tautomer, pharmaceutically acceptable salt thereof, wherein:

ring A is selected from

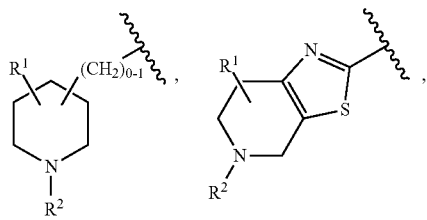

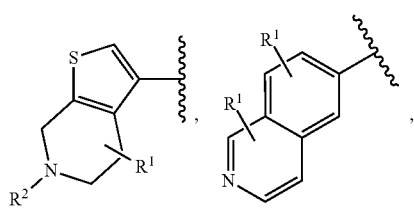

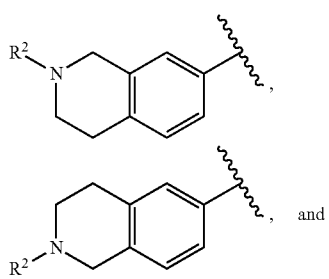, and

-continued

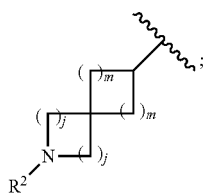

R¹, at each occurrence, is H;

R² is selected from —C(=NH)NH₂ and C(=NOR⁶)NH₂;

$R^{3a}$, at each occurrence, is selected from H, halogen, $C_{1-4}$ alkyl, —OH, $C_{1-4}$ alkoxy, —CN, —NH₂, —NH($C_{1-4}$ alkyl), —N($C_{1-4}$ alkyl)₂, —CO₂H, CO₂($C_{1-4}$ alkyl), and —NHCO₂($C_{1-4}$ alkyl);

$R^{4a}$, $R^{4b}$, $R^{4c}$, and $R^{4d}$ are independently selected from H, F, and $C_{1-4}$ alkyl;

R⁵, at each occurrence, is selected from H, F,

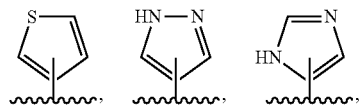

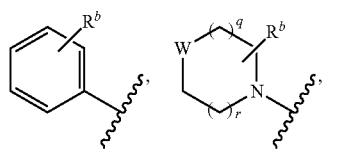

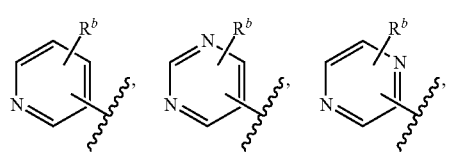

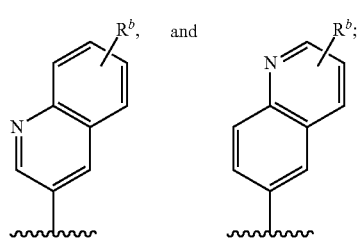

R⁶, at each occurrence, is selected from H and $C_{1-4}$ alkyl;

W is selected from $CR^bR^b$, O, $S(O)_p$, and $NR^a$;

$R^a$ is selected from H and $C_{1-4}$ alkyl; and $R^b$ is selected from H, =O, OH, halogen, $C_{1-4}$ alkyl, $C_{1-4}$ alkoxy, OCF₃, NH₂, N($C_{1-4}$ alkyl)₂, CO($C_{1-4}$ alkyl), CO($C_{1-4}$ haloalkyl), CO₂($C_{1-4}$ alkyl), CONH₂, —CONH($C_{1-4}$ alkyl), and —CON($C_{1-4}$ alkyl)₂.

10. The compound of claim 9 having formula (IV):

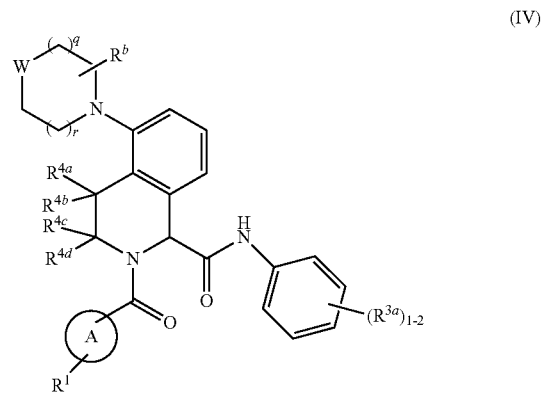

(IV)

or a stereoisomer, tautomer, pharmaceutically acceptable salt thereof, wherein:

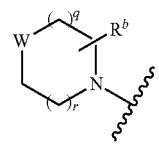

is selected from

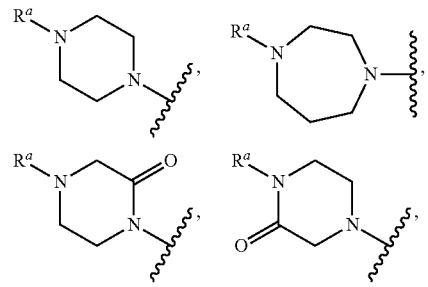

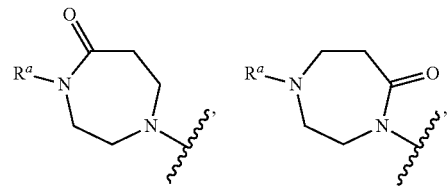

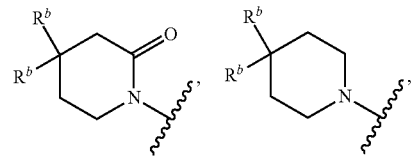

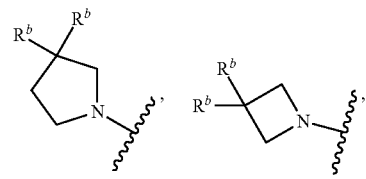

-continued

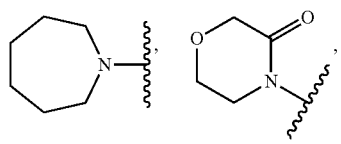

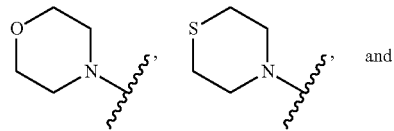 and

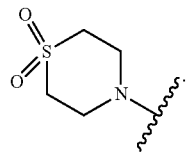

11. The compound of claim 10 having formula (V):

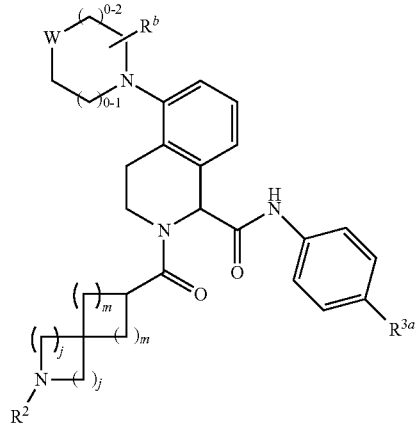

(V)

or a stereoisomer, tautomer, pharmaceutically acceptable salt thereof, wherein:

$R^2$ is —C(=NH)NH$_2$;

$R^{3a}$ is selected from CO$_2$H, CO$_2$(C$_{1-4}$ alkyl), and NHCO$_2$(C$_{1-4}$ alkyl);

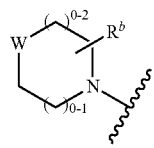

is selected from

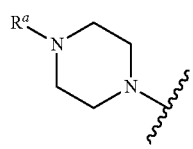

-continued

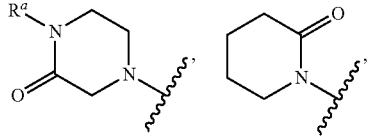

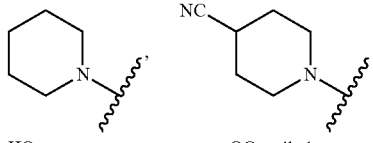

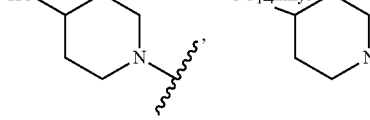

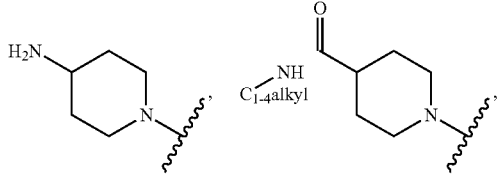

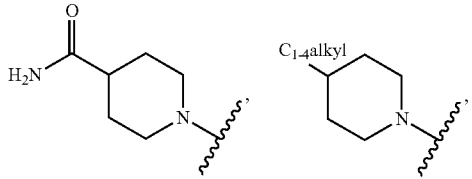

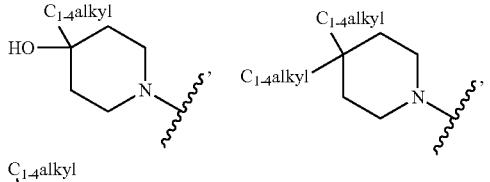

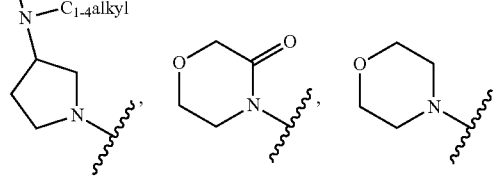

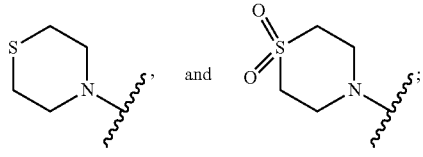

m, at each occurrence, is selected from 1 and 2; and j, at each occurrence, is selected from 1 and 2.

12. The compound of claim 11 or a stereoisomer, tautomer, pharmaceutically acceptable salt thereof, wherein:

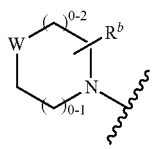

is selected from

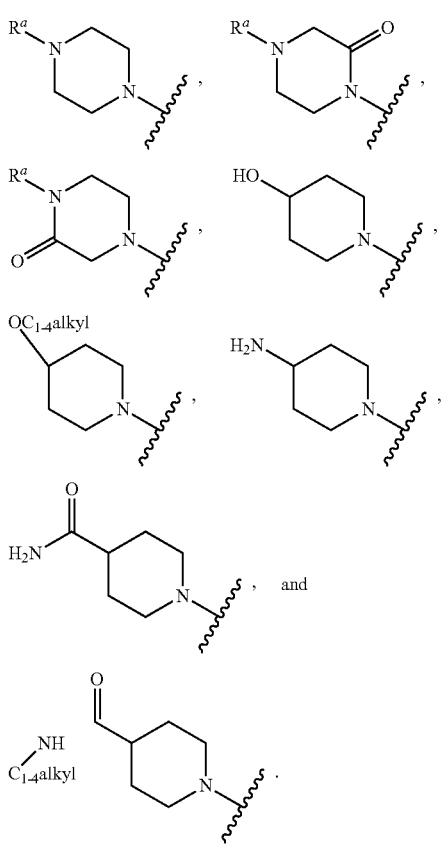
13. The compound of claim 11 having formula (VI):
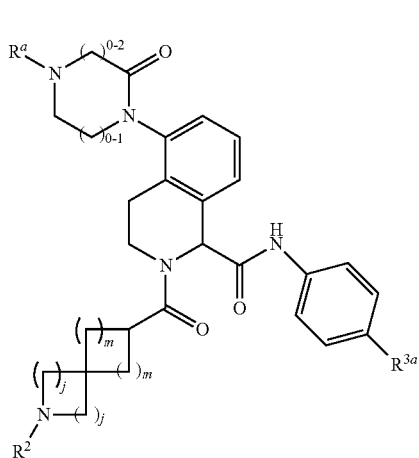
(VI)
or a stereoisomer, tautomer, pharmaceutically acceptable salt thereof, wherein:
$R^2$ is —C(=NH)NH$_2$;
$R^{3a}$ is selected from —CO$_2$H, —CO$_2$Me, and —NHCO$_2$Me;
$R^a$ is selected from H and C$_{1-4}$ alkyl;
j is 1 or 2; and
m is 1 or 2.
14. A compound of claim 1 selected from
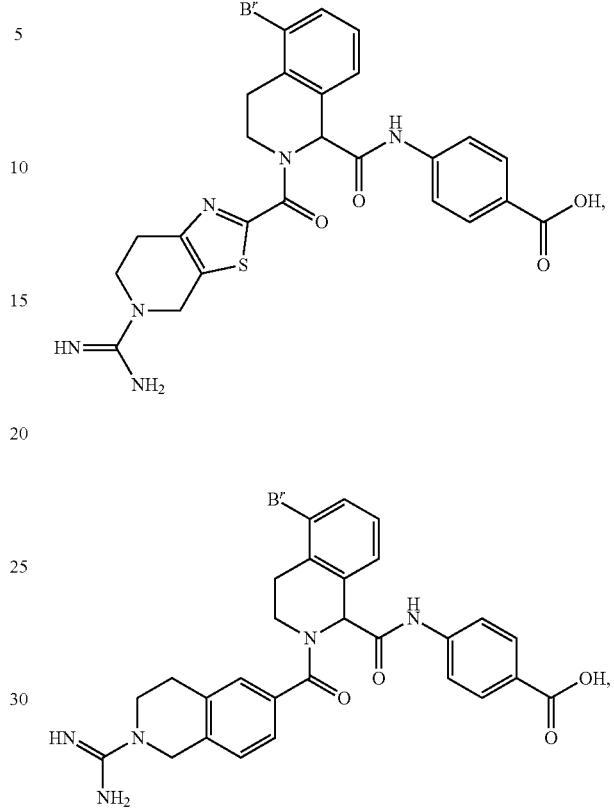
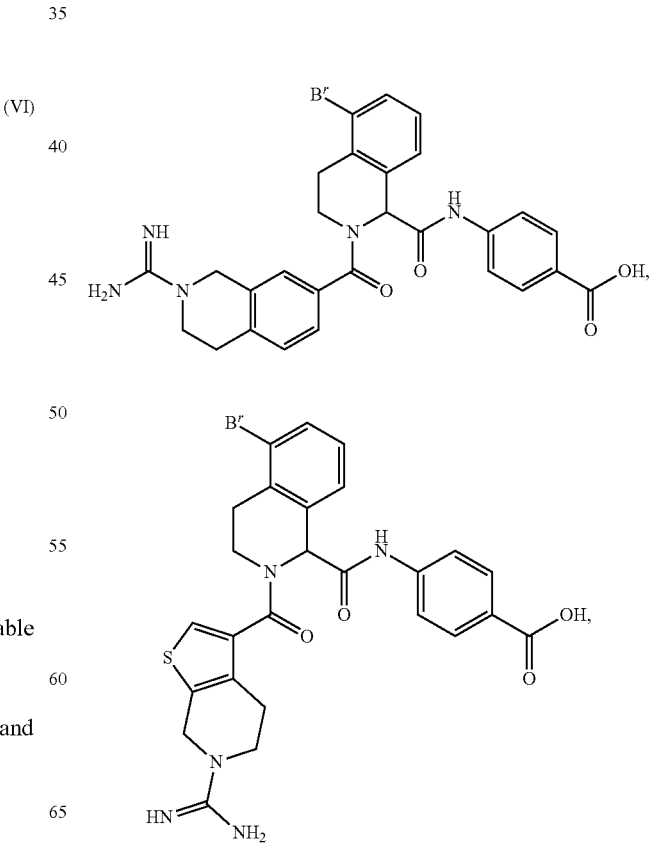

93
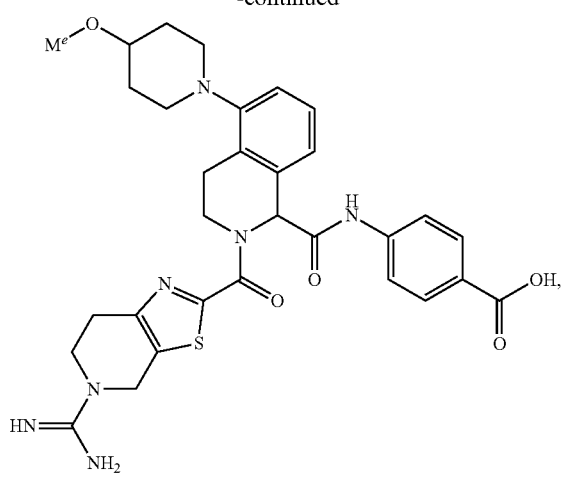
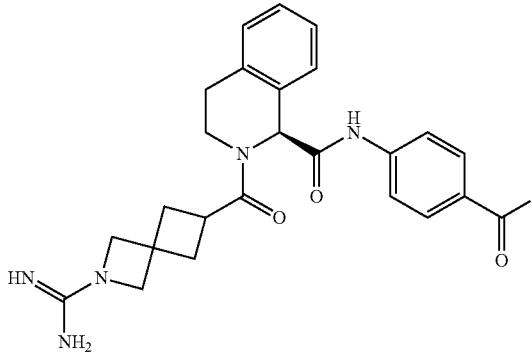
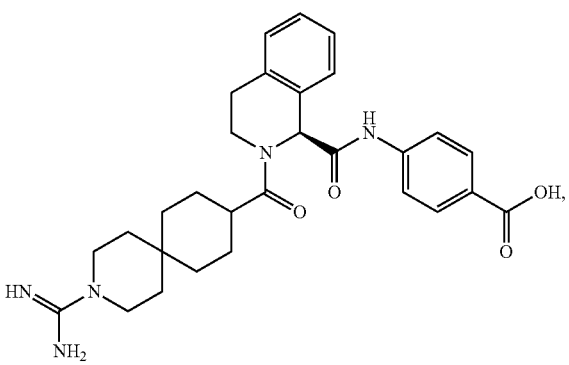
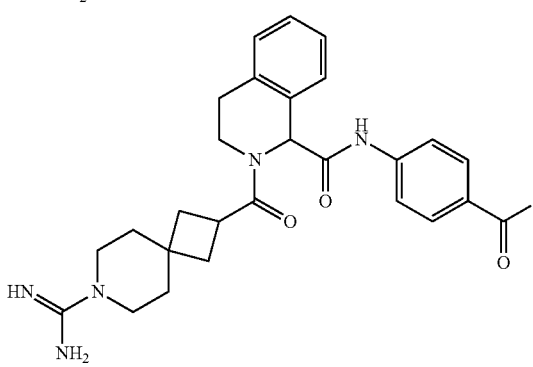
94
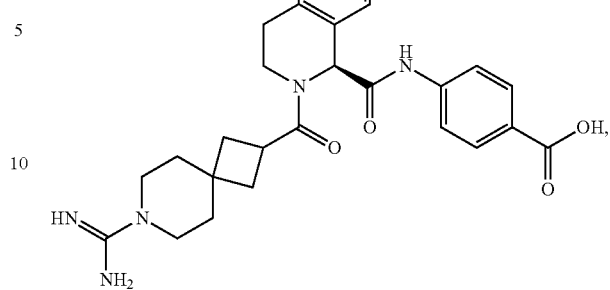
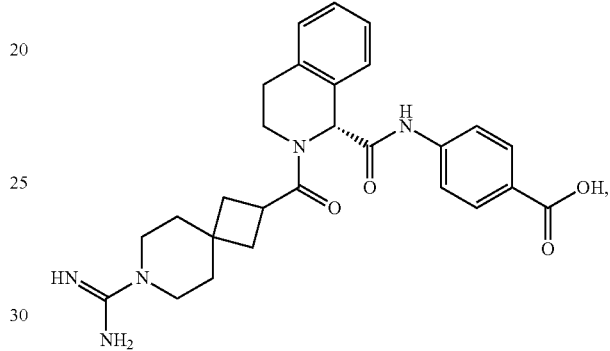
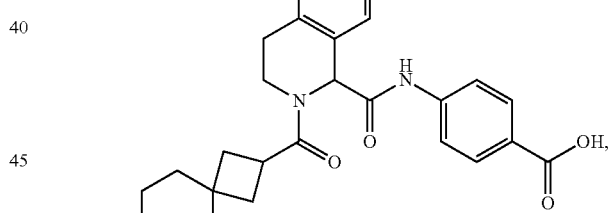
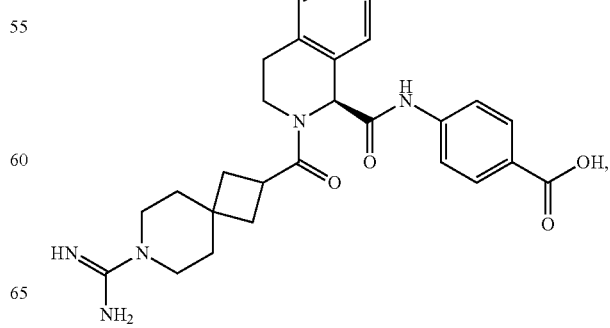

95
-continued
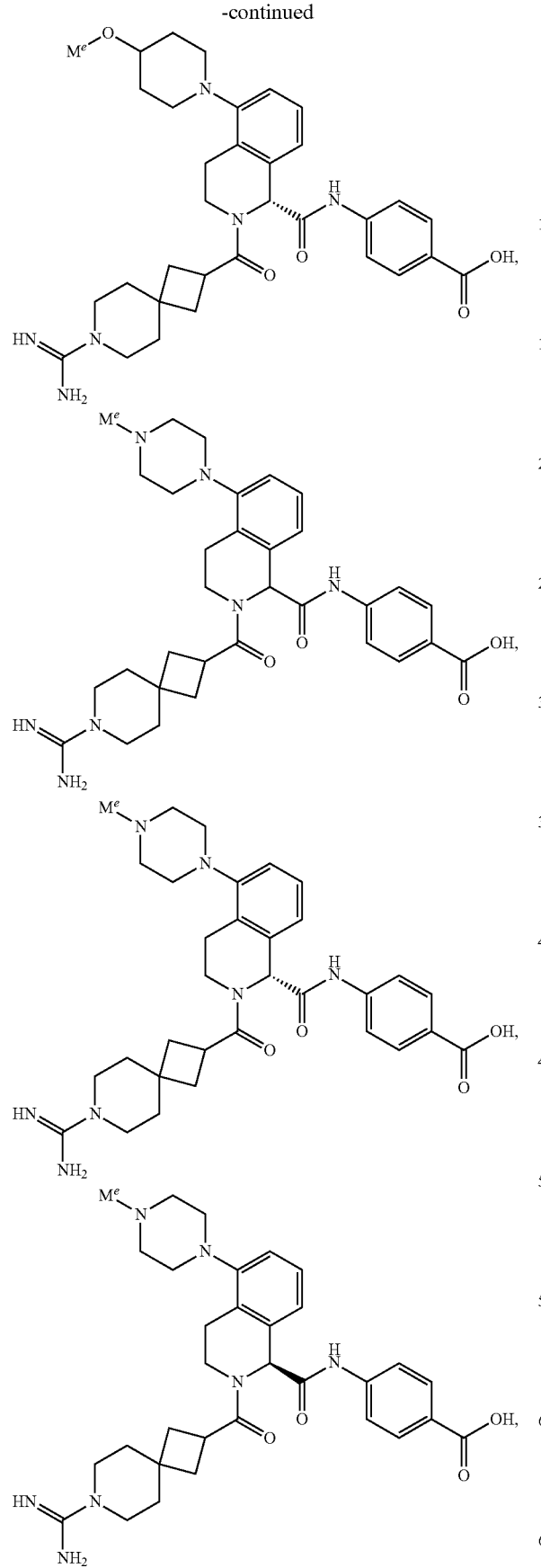
96
-continued
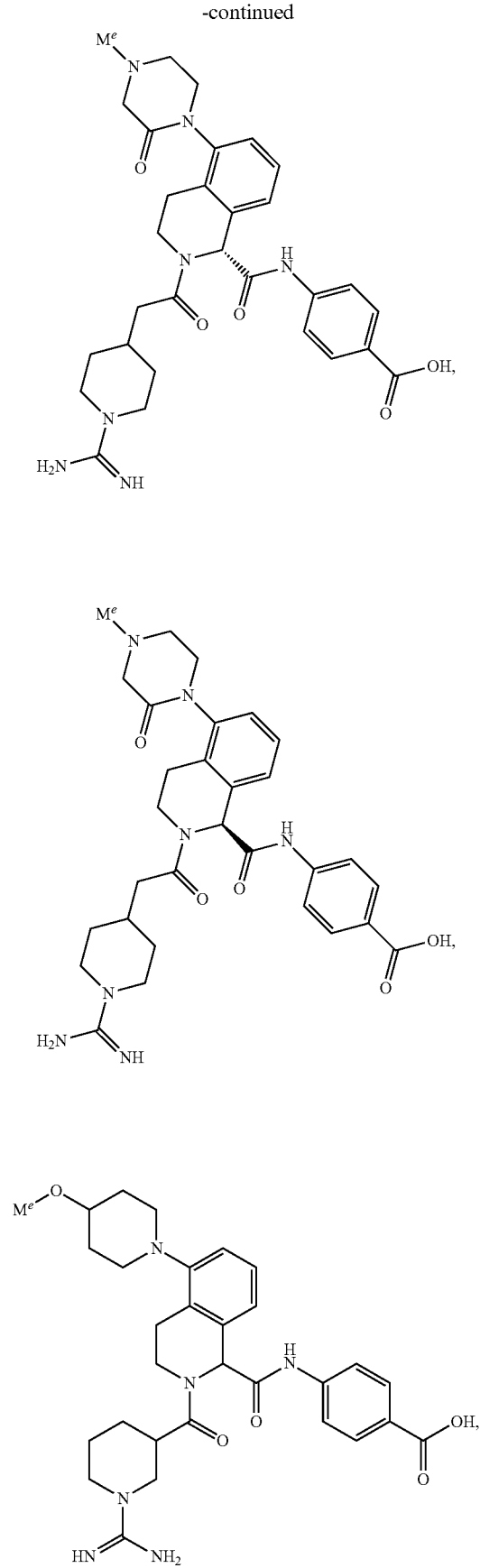

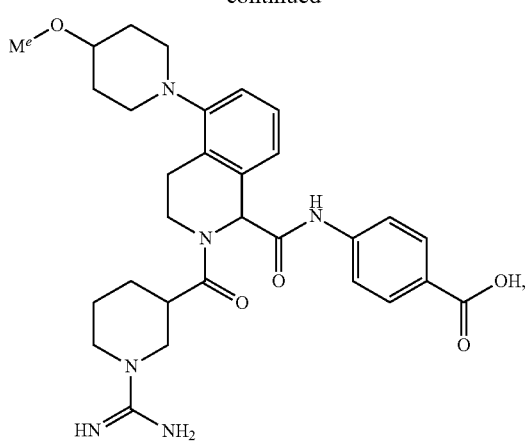

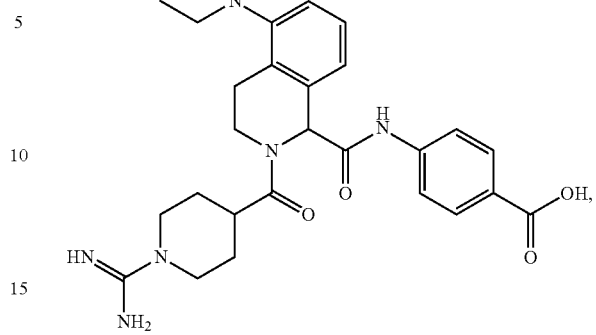

or a stereoisomer, tautomer, pharmaceutically acceptable salt thereof.

15. A compound selected from

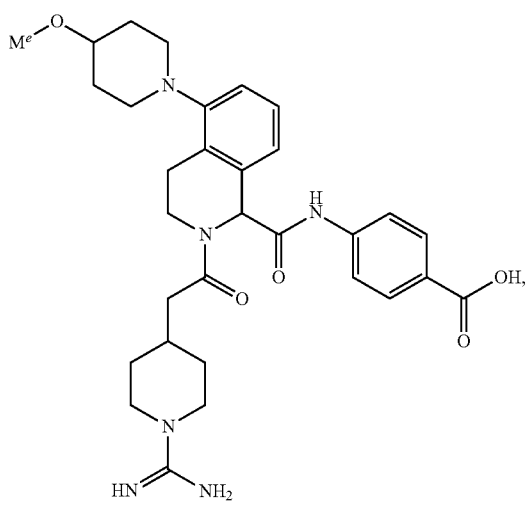

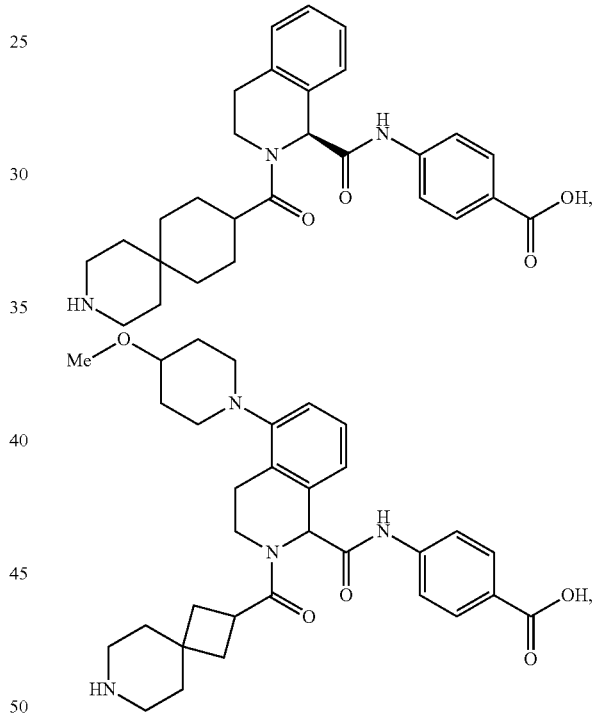

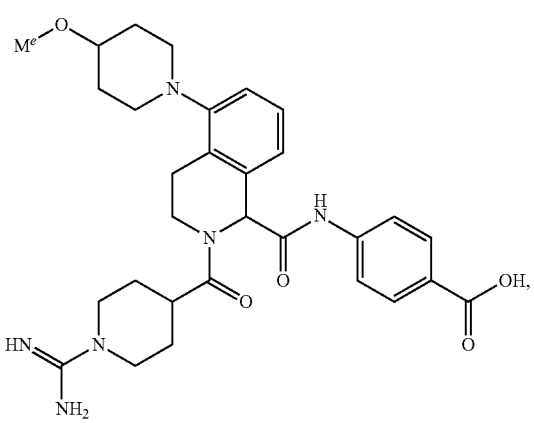

or a stereoisomer, tautomer, pharmaceutically acceptable salt thereof.

16. A pharmaceutical composition, comprising: a pharmaceutically acceptable carrier and a therapeutically effective amount of a compound of claim 1.

17. A method of treating a thromboembolic or an inflammatory disorder, comprising: administering to a patient in need thereof a therapeutically effective amount of a compound of claim 1 or a pharmaceutically acceptable salt or solvate form thereof.

18. A method of treating a thromboembolic disorder according to claim 17, wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

\* \* \* \* \*